(12) United States Patent
Pashley et al.

(10) Patent No.: US 8,951,505 B2
(45) Date of Patent: Feb. 10, 2015

(54) METHODS AND SYSTEMS FOR MINERALIZATION OF DEMINERALIZED TISSUE

(75) Inventors: David Henry Pashley, Augusta, GA (US); Franklin Chi-Meng Tay, Augusta, GA (US)

(73) Assignee: Georgia Health Sciences University Rsearch Institute, Inc., Augusta, GA (US)

( * ) Notice: Subject to any disclaimer, the term of this patent is extended or adjusted under 35 U.S.C. 154(b) by 1107 days.

(21) Appl. No.: 12/576,058

(22) Filed: Oct. 8, 2009

(65) Prior Publication Data

US 2010/0086618 A1    Apr. 8, 2010

Related U.S. Application Data

(60) Provisional application No. 61/195,561, filed on Oct. 8, 2008.

(51) Int. Cl.
| | |
|---|---|
| A61Q 11/00 | (2006.01) |
| A61K 8/02 | (2006.01) |
| A61K 8/24 | (2006.01) |
| A61K 33/06 | (2006.01) |
| A61K 6/033 | (2006.01) |

(52) U.S. Cl.
CPC .................................... A61K 6/033 (2013.01)
USPC ............... 424/49; 424/57; 424/601; 424/602; 424/682; 424/401; 424/693; 433/215; 433/216; 433/217.1

(58) Field of Classification Search
USPC ............. 424/49, 57, 601, 602, 682, 693, 401; 433/215, 216, 217.1
See application file for complete search history.

(56) References Cited

U.S. PATENT DOCUMENTS

| | | | | |
|---|---|---|---|---|
| 4,930,428 | A * | 6/1990 | Schneider et al. | 106/640 |
| 5,693,313 | A * | 12/1997 | Shiraishi et al. | 424/49 |
| 5,858,333 | A | 1/1999 | Winston et al. | |
| 6,010,684 | A | 1/2000 | Wiedemann | |
| 6,398,859 | B1 | 6/2002 | Dickens et al. | |
| 7,204,875 | B2 * | 4/2007 | Jia et al. | 106/35 |
| 2002/0045678 | A1 * | 4/2002 | Lopez et al. | 523/116 |
| 2003/0165440 | A1 * | 9/2003 | Roth et al. | 424/50 |
| 2004/0146466 | A1 * | 7/2004 | Baig et al. | 424/49 |
| 2004/0202621 | A1 * | 10/2004 | Orlowski et al. | 424/53 |
| 2006/0204581 | A1 | 9/2006 | Gower et al. | |

FOREIGN PATENT DOCUMENTS

| | | |
|---|---|---|
| WO | WO 2006/135982 | 12/2006 |
| WO | WO 2008/068149 | 6/2008 |

OTHER PUBLICATIONS

International Search Report and Written Opinion mailed Dec. 6, 2011 for corresponding International Application No. PCT/US2009/060052.

International Preliminary Report on Patentability mailed Dec. 22, 2011 for corresponding International Application No. PCT/US2009/060052.

Traub, W. et al., "Origin of Mineral Crystal Growth in Collagen Fibrils," Matrix, 1992, 12:251-255.

Landis, W. J. et al., "Structural Relations Between Collagen and Mineral in Bone as Determined by High Voltage Electron Microscopic Tomography," Microsc. Res. Tech., 1996, 33:192-202.

Vaidyanathan, T. K. et al., "Recent Advances in the Theory and Mechanism of Adhesive Resin Bonding to Dentin: A Critical Review," J. Biomed. Mater. Res. Part B Appl. Biomater., 2009, 88B:558-578.

Bernardo, M. et al., "Survival and reasons for failure of amalgam versus composite posterior restorations placed in a randomized clinical trial," J. Am. Dent. Assoc., 2007, 138:775-783.

De Munck, J. et al., "A Critical Review of the Durability of Adhesion to Tooth Tissue: Methods and Results," J. Dent. Res., 2005, 84:118-132.

Ito, S. et al., "Effects of resin hydrophilicity on water sorption and changes in modulus of elasticity," Biomaterials, 2005, 26:6449-6459.

Pashley, D.H. et al., "Collagen Degradation by Host-derived Enzymes during Aging," J. Dent. Res., 2004, 83:216-221.

Breschi, L. et al., "Dental adhesion review: Aging and stability of the bonded interface," Dent. Mater., 2008, 24:90-101.

Kinney, J.H., et al., "The Importance of Intrafibrillar Mineralization of Collagen on the Mechanical Properties of Dentin," J. Dent. Res., 2003, 82:957-961.

Jäger, I. et al., "Mineralized Collagen Fibrils: A Mechanical Model with a Staggered Arrangement of Mineral Particles," Biophy. J., 2000, 79:1737-1746.

Maciel, K. et al., "The Effects of Acetone, Ethanol, HEMA, and Air on the Stiffness of Human Decalcified Dentin Matrix," J. Dent. Res., 1996, 75:1851-1858.

Balooch, M. et al., "Viscoelastic properties of demineralized human dentin measured in water with atomic force microscope (AFM)-based indentation," J. Biomed. Mater Res.,1998, 40:539-544.

Wagner, H. et al., "On the Relationship Between the Microstructure of Bone and its Mechanical Stiffness," J. Biomech., 1992, 25:1311-1320.

Beniash, E. et al., "A Transmission Electron Microscope Study Using Vitrified Ice Sections of Predentin: Structural Changes in the Dentin Collagenous Matrix prior to Mineralization," J. Struct. Biol., 2000, 132:212-225.

George, A. et al., "Phosphorylated Proteins and Control over Apatite Nucleation, Crystal Growth, and Inhibition," Chem. Rev., 2008, 108:4670-4693.

He, G. et al., "Spatially and temporally controlled biomineralization is facilitated by interaction between self-assembled dentin matrix protein 1 and calcium phosphate nuclei in solution," Biochemistry, 2005, 44:16140-16148.

Olszta, M. J. et al., "A New Paradigm for Biomineral Formation: Mineralization via an Amorphous Liquid-Phase Precursor," Connect Tissue Res., 2003, 44 (Suppl 1):326-334.

(Continued)

*Primary Examiner* — Lezah Roberts

(74) *Attorney, Agent, or Firm* — Kilpatrick Townsend & Stockton LLP

(57) ABSTRACT

Disclosed are systems, methods, compositions and kits for mineralizing tissue, particularly dental tissue. The methods, compositions and kits may be used to strengthen and prevent weakening of the tissue. For example, the methods, compositions and kits may be used for treating and filling cavities in teeth caused by tooth decay.

5 Claims, 31 Drawing Sheets

(56) References Cited

OTHER PUBLICATIONS

He, G. et al., "Phosphorylation of Phosphophoryn is Crucial for Its Function as a Mediator of Biomineralization," J. Biol. Chem., 2005, 280:33109-33114.

Bingöl, B. et al., "Synthesis, Microstructure, and Acidity of Poly(vinylphosphonic acid)," Macromol. Rapid Commun., 2006, 27:1719-1724.

Li, X. et al., "Preparation of bone-like apatite-collagen nanocomposites by a biomimetic process with phosphorylated collagen," J. Biomed. Mater. Res. A., 2008, 85A:293-300.

Mai, S. et al, "Phosphoric acid esters cannot replace polyvinylphosphonic acid as phosphoprotein analogs in biomimetic remineralization of resin-bonded dentin," Dent. Mater., 2009, 25:1230-1239.

Sarkar, N. K. et al., "Physicochemical Basis of the Biologic Properties of Mineral Trioxide Aggregate," J. Endod . . . , 2005, 31:97-100.

Ford, T.R. et al., "Using mineral trioxide aggregate as a pulp-capping material," J. Am. Dent. Assoc., 1996, 127:1491-1494.

Kawasaki, K. et al., "Evolutionary Genetics of Vertebrate Tissue Mineralization: The Origin and Evolution of the Secretory Calcium-Binding Phosphoprotein Family," J. Exp. Zool. (Mol. Dev. Evol.), 2006, 306B:295-316.

Veis, A., "Mineral-Matrix Interactions in Bone and Dentin," J. Bone Miner. Res., 1993, 8:S493-S497.

Gajjeraman, S. et al., "Matrix Macromolecules in Hard Tissues Control the Nucleation and Hierarchical Assembly of Hydroxyapatite," J. Biol. Chem., 2007, 282:1193-1204.

Qin, C. et al., "Dentin Matrix 1 (DMP1): New and Important Roles for Biomineralization and Phosphate Homeostasis," J. Dent. Res., 2007, 86:1134-1141.

George, A. et al., "Characterization of a Novel Dentin Matrix Acidic Phosphoprotein," J. Biol. Chem., 1993, 268:12624-12630.

Banks, E. et al., "Fibrous Apatite Grown on Modified Collagen," Science, 1977, 198:1164-1166.

Tanahashi, M. et al., "Surface functional group dependence on apatite formation on self-assembled monolayers in a simulated body fluid," J. Biomed. Mater. Res., 1997, 34:305-315.

He, G. et al., "Dentin Matrix Protein 1 Immobilized on Type I Collagen Fibrils Facilitates Apatite Deposition in Vitro," J. Biol. Chem., 2004, 279:11649-11656.

Huq, N.L. et al., "Association of bovine dentine phosphophoryn with collagen fragments," Arch. Oral Biol., 2005, 50:807-819.

Landis, W., "The Strength of a Calcified Tissue Depends in Part on the Molecular Structure and Organization of its Constituent Mineral Crystals in their Organic Matrix," Bone, 1995, 16:533-544.

Arsenault, A., "Crystal-Collagen Relationships in Calcified Turkey Leg Tendons Visualized by Selected-Area Dark Field Electron Microscopy," Calcif. Tissue Int., 1988, 43:202-212.

Liou, S.C. et al., "Manipulation of Nanoneedle and Nanosphere Apatite/Poly(Acrylic Acid) Nanocomposites," J. Biomed. Mater. Res. B: Appl. Biomater., 2005, 73B:117-122.

Oaki, Y. et al., "Bridged Nanocrystals in Biominerals and Their Biomimetics: Classical Yet Modern Crystal Growth on the Nanoscale," Adv. Func. Mater., 2006, 16:1633-1639.

Stupp, S. I. et al., "Supramolecular Materials: Self-Organized Nanostructures," Science, 1997, 276:384-389.

Girija, E.K. et al., "Apatite formation on collagen fibrils in the presence of polyacrylic acid," J. Mater. Sci.: Mater. Med., 2004, 15:593-599.

Ye, Q. et al., "In vitro Performance of Nano-heterogeneous Dentin Adhesive," J. Dent. Res., 2008, 87:829-833.

Miguez, P. et al., "Collagen Cross-linking and Ultimate Tensile Strength in Dentin," J. Dent. Res., 2004, 83:807-810.

Nishitani, Y. et al., "Tensile Strength of Mineralized/Demineralized Human Normal and Carious Dentin," J. Dent. Res., 2005, 84:1075-1078.

Tay, F.R. et al., "Calcium Phosphate Phase Transformation Produced by the Interaction of the Portland Cement Component of White Mineral Trioxide Aggregate with a Phosphate-containing Fluid," J. Endod., 2007, 33:1347-1351.

Tay, F.R. et al., "Aging Affects Two Modes of Nanoleakage Expression in Bonded Dentin," J. Dent. Res., 2003, 82:537-541.

Nakabayashi, N. et al., "Dentin adhesion of 'modified' 4-META/MMA-TBB resin: function of HEMA," Dent. Mater., 1992, 8:259-264.

Bradt, J. H. et al., "Biomimetic Mineralization of Collagen by Combined Fibril Assembly and Calcium Phosphate Formation," Chem. Mater., 1999, 11:2694-2701.

Bozec, L. et al., "Collagen Fibrils: Nanoscale Ropes," Biophys. J., 2007, 92:70-75.

Klont, B. et al., "Release of Organic Matrix Components from Bovine Incisor Roots during in vitro Lesion Formation," J. Dent. Res., 1990, 69:896-900.

Kokubo, T. et al., "Solutions able to reproduce in vivo surface-structure changes in bioactive glass-ceramic A-W," J. Biomed. Mater. Res., 1990, 24:721-734.

Munisamy, S. et al., "A Bone-Like Precoating Strategy for Implants: Collagen Immobilization and Its Mineralization on Pure Titanium Implant Surface," J. Oral Implantol., 2008, 34:67-75.

Tay, F. R. et al., "Guided tissue remineralisation of partially demineralised human dentine," Biomaterials, 2008, 29:1127-1137.

Tay, F.R. et al., "Distribution of Nanofillers from a Simplified-Step Adhesive in Acid-Conditioned Dentin," J. Adhes. Dent, 1999, 1:103-117.

Tay, F.R. et al., "Two Modes of Nanoleakage Expression in Single-step Adhesives," J. Dent. Res., 2002, 81:472-476.

Tay, F.R. et al., "Water Treeing in Simplified Dentin Adhesives—Déjà vu?" Oper. Dent, 2005, 30:561-579.

Niederberger, M. et al., "Oriented attachment and mesocrystals: Non-classical crystallization mechanisms based on nanoparticle assembly," Phys. Chem. Chem. Phys., 2006, 8:3271-3287.

Xu, A-W. et al., "Biomimetic mineralization," J. Mater. Chem., 2007, 17:415-449.

Mishima, H. et al., "Demonstration of Structural Variation in Rat Incisor Dentin as Determined by the X-ray Laue Method," J. Dent. Res., 1986, 65:932-934.

Müller, F.A. et al., "Preferred growth orientation of biomimetic apatite crystals," J. Crystal Growth, 2007, 304:464-471.

Soncini, J.A., et al., "The longevity of amalgam versus compomer/composite restorations in posterior primary and permanent teeth: Findings From the New England Children's Amalgam Trial," J. Am. Dent. Assoc., 2007, 138:763-772.

Markovic, M. et al., "Preparation and Comprehensive Characterization of a Calcium Hydroxyapatite Reference Material," J. Res. Natl. Inst. Stand. Technol., 2004, 109:553-568.

Liou , S-C. et al., "Manipulation of Nanoneedle and Nanosphere Apatite/Poly(Acrylic Acid) Nanocomposites", J. Biomed. Mater. Res. Part B: Appl. Biomater., 2005, 73B:117-22.

* cited by examiner

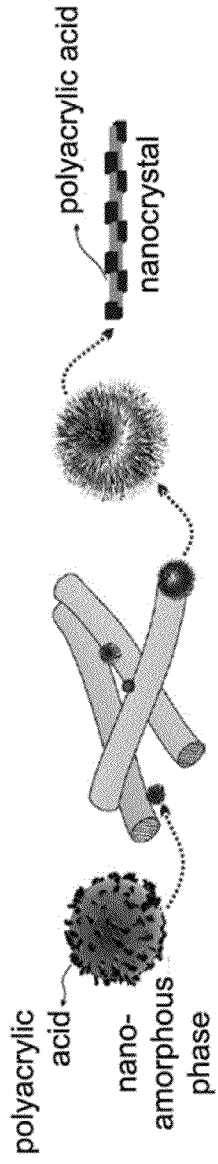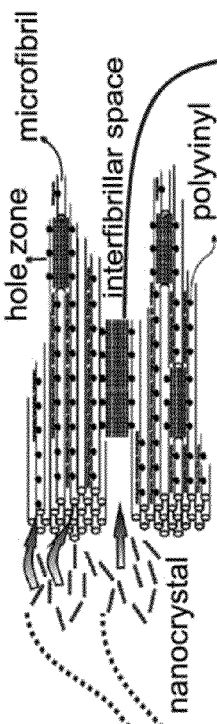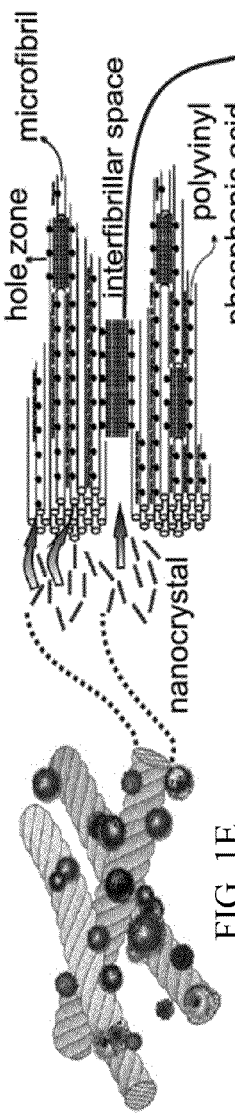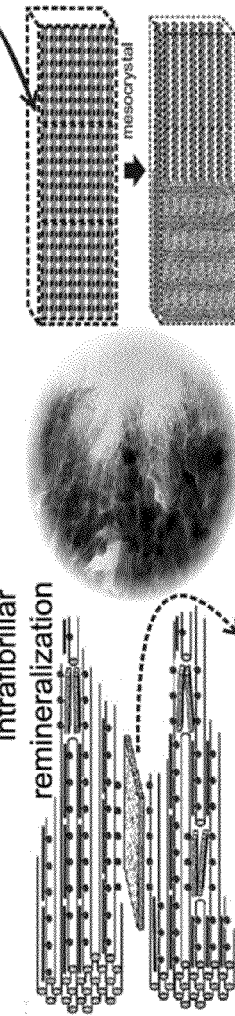

FIG. 5A
FIG. 5B
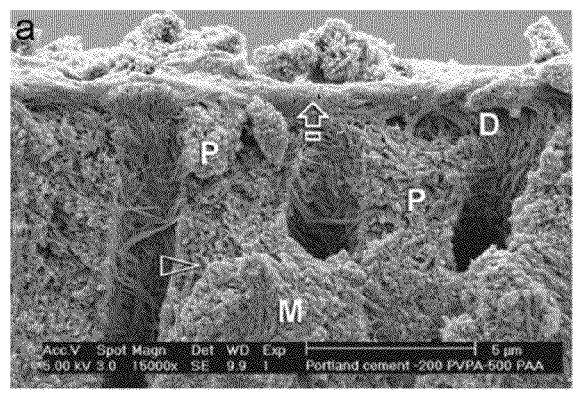
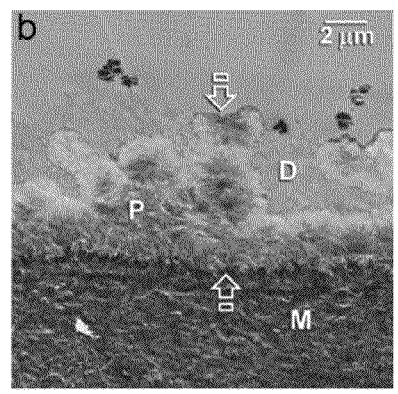
FIG. 5C
FIG. 5D
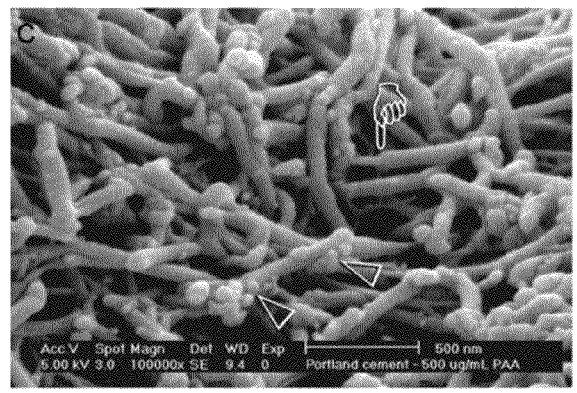
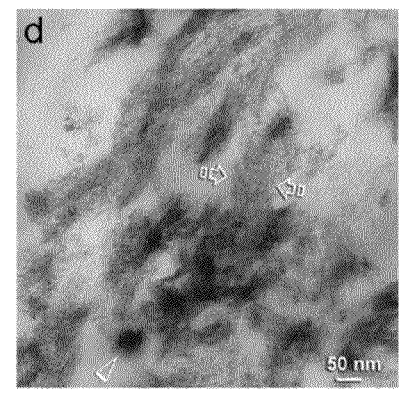

FIG. 5E
FIG. 5F
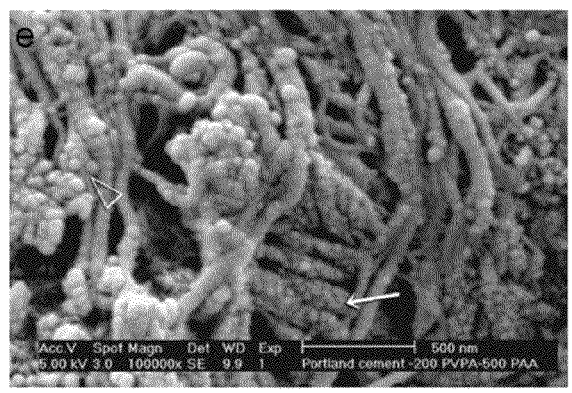 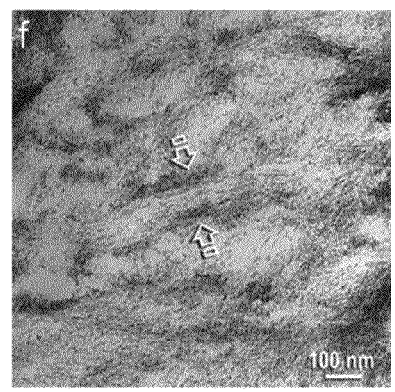
FIG. 5G
FIG. 5H
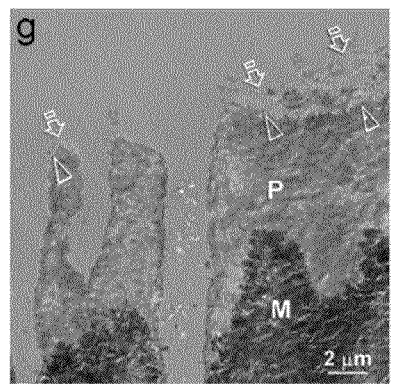 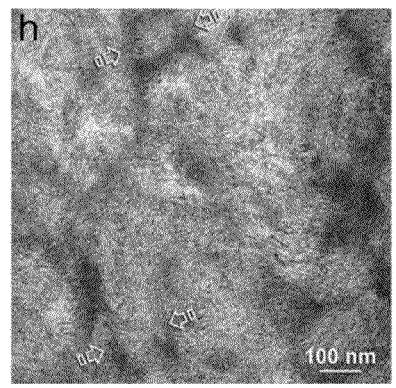

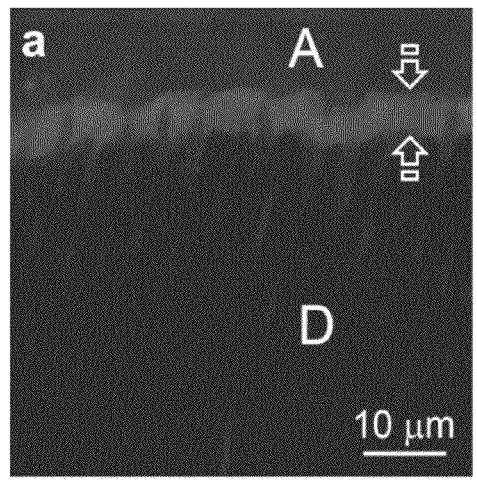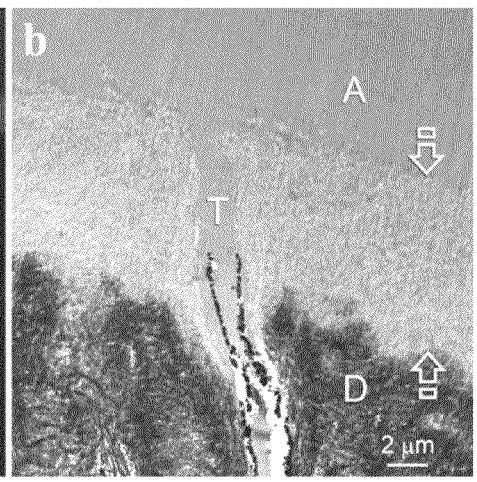
FIG. 15A  FIG. 15B
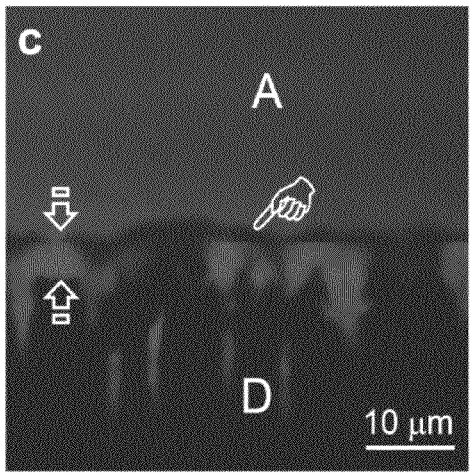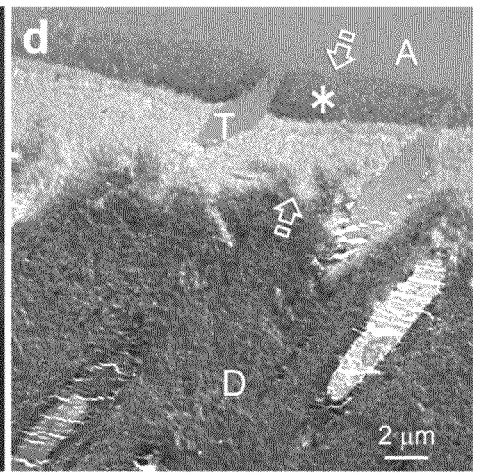
FIG. 15C  FIG. 15D

METHODS AND SYSTEMS FOR MINERALIZATION OF DEMINERALIZED TISSUE

CROSS-REFERENCE TO RELATED APPLICATION

This application claims the benefit of provisional U.S. Provisional Patent Application Ser. No. 61/195,561, filed Oct. 8, 2008, the entirety of which is herein incorporated by reference.

STATEMENT REGARDING FEDERALLY SPONSORED RESEARCH OR DEVELOPMENT

Some aspects of the invention described in this application were sponsored by 1R21 DE019213-01A1 from the National Institute of Dental and Craniofacial Research. Accordingly, the Federal Government has rights in this application.

FIELD OF THE INVENTION

The present invention relates to methods and systems for mineralization of demineralized tissue. In some cases, the tissue is dental tissue.

BACKGROUND

Teeth are one of the tissues in the body that undergo biomineralization, the process by which living organisms secrete inorganic minerals in the form of biominerals within body tissue and/or structures. Teeth have four major components: enamel, dentin (or dentine), cementum and pulp. The enamel of a tooth is the intensely hard calcareous (i.e., calcium based) substance that forms a thin layer which caps or partly covers the teeth of most mammals, including humans and other vertebrates. Dentin also comprises calcareous material. It is usually covered by enamel on the crown and cementum on the root and surrounds the entire pulp (i.e., the living tissue of the tooth). Dentin is a living tissue comprised of a mineralized matrix p minute tubules which enter into the inner cavity of the tooth where the pulp is housed. The major organic component of dentin is type I collagen. Type I collagen forms a three-dimensional network within which deposition of non-collagenous proteins and the nucleation of hydroxyapatite crystals occur. The cementum is a thin, fairly hard bone tissue covering the root of the tooth.

Dental caries, also known as tooth decay or cavity, is one of the most ubiquitous bacterial infections in world. Dental caries is a disease wherein bacterial processes damage hard tooth structure (enamel, dentin and cementum). Remineralization of structurally intact dentin matrix previously demineralized by dental caries and the treatment of dental caries by the creation of dental fillings is of imminent concern from public health and research perspectives. Similar to bone, the apatite phase in mineralized dentin is classified as either intrafibrillar, referring to the hole zones and pore spaces within the collagen fibrils, and interfibrillar, referring to the interstitial spaces separating the individual collagen fibrils. (US 2006-0204581; Traub, W. et al., *Matrix,* 1992, 12:251-255; Landis, W. J. et al., *Microsc. Res. Tech.,* 1996, 33:192-202).

To date, the treatment of dental caries is focused mainly on a surgical model of removing the carious tooth structure followed by replacement with an inert restorative material. Once dental caries is found in a tooth, the typical therapy is to remove the caries. Therapy for cavities formed by decay is typically referred to as a "filling" or resin bonding. Dentin bonding is a unique form of tissue engineering in which a demineralized collagen matrix continuous with the underlying mineralized dentin is created via acid-etching or acidic self-etching adhesives and used as the scaffold for resin infiltration. In accordance with this procedure, a dentist or other authorized practitioner may use a drill or a laser to remove the carious dental tissue and may also form undercuts in order to secure the filling material. The cut surface of the tooth is acid etched and the dentist then fills the cavity with a restorative material to replace the portion of the tooth lost to decay, the restorative material becoming bonded to the tooth tissue. This filling material is placed downward into the tooth from the upper or crown regions of the tooth. Alternatively, the carious dental tissue itself may be acid etched without invasive removal of carious dental tissue prior to application of the restorative material. Restorative material may be adhered to teeth using dental adhesives, which rely on micromechanical entanglement of resin polymers within partially or completely demineralized collagen matrices for retention of the resin composite fillings. (Vaidyanathan and Vaidyanathan, *J. Biomed. Mater. Res. B Appl. Biomater.* 2009, 82:558-578) Infiltration of resins into the demineralized dentin creates a so-called interdiffusion zone or hybrid layer.

Despite significant improvements in contemporary resin composites and their bonding to tooth structures via the use of dentin adhesives, it is estimated that half of all resin composite restorations fail within 10 years. Replacement of failed composite restorations accounts for 50-70% of all restorations and replacing them consumes 60% of the dentist's practice time. Secondary caries at the tooth-restoration margins is a major reason for the replacement of existing restorations. Composite-dentin bonds are continuously challenged by the harsh mechanical and chemical environment of the oral cavity, with the risk of secondary caries being 3.5 times higher in resin composite than in amalgam restorations (Bernardo et al., *J. Am. Dent. Assoc.,* 2007, 138:775-783). As replacement dentistry costs about 5 billion dollars annually in the United States alone, there is a compelling need to pursue alternative methods to preserve resin-dentin bond integrity and extend the longevity of resin-based restorations.

Unstable bonding of resin-based fillings to teeth is partly due to the proteinaceous nature of dentin, which can result in incomplete infiltration of the resin into the tooth structure. The most compelling problem associated with resin-dentin bonds is limited durability (De Munck, J. et al., *J. Dent. Res.,* 2005, 84:118-132), which can be caused partially by water sorption-induced hydrolysis of the hydrophilic resin components present in these adhesives (Ito, S. et al., *Biomaterials,* 2005, 26:6449-6459), and partially by degeneration of collagen fibrils via endogenous matrix metalloproteinases (MMPs) derived from the demineralized dentin (Pashley, D. H. et al., *J. Dent. Res.,* 2004, 83:216-221). While hydrophilic resin monomers are conventionally thought to be important for bonding of resins to dentin, their inclusion in restorative materials may cause the resulting resin-dentin bonds to be susceptible to degradation via water sorption, hydrolysis of resin ester linkages and activation of endogenous collagen degrading enzymes (Breschi et al. *Dent. Mater.,* 2008, 24:90-101).

When tooth dentin becomes demineralized, especially from the caries process, the dentin loses its mechanical properties and becomes softer, weaker and less stiff. Such dentin often loses half its mineral phase that is replaced by water. This weakened dentin provides a poor foundation for crowns, bridges and restorative materials. Thus, mineralization of dental tissue weakened by dental caries and/or acid-etching-demineralization is desirable to strengthen tooth structure.

Heterogeneous deposition of calcium phosphate minerals in interfibrillar collagen spaces alone does not result in a highly mineralized collagen matrix and, in the absence of intrafibrillar dentin mineralization, the hardness and modulus of elasticity in carious dentin is inferior to those of sound dentin (Kinney, J. H., et al., *J. Dent. Res.*, 2003, 82:957-961); Jäger, I. et al., *Biophy. J.*, 2000, 79:1737-1746. Therefore, in order to produce remineralized dentin comparable to that of sound dentin, both interfibrillar and intrafibrillar remineralization may be required.

Thus, development of remineralization approaches for dental caries, as well as improvement of resin-dentin bonding (i.e., for fillings) is highly desirable. In the case of caries, apatite crystals that are present within and surrounding the enamel, dentin and cementum tissues can serve as the nuclei for apatite crystal deposition. However, in the case of resin-dentin bonds, there are zones of completely demineralized dentin adjacent to the resin surface within which apatite crystal deposition must be initiated de novo.

SUMMARY

Embodiments of the present invention relate to biomimetic remineralization of demineralized dental hard tissues. The present invention may be embodied in a variety of ways.

In one embodiment, the invention comprises methods of producing mineralized dental tissue. In one embodiment, the method comprises incubating a site on the dental tissue with a remineralizing restorative material, wherein the remineralizing restorative material comprises a calcium ion source and a hydroxide ion source, wherein the calcium ions and the hydroxide ions are provided at the site of mineralization at a rate suitable to promote the formation of interfibrillar and intrafibrillar apatite crystals within collagen at the site of mineralization. In certain embodiments, the calcium ions and the hydroxyl ions may form calcium hydroxide. In other embodiments, the calcium hydroxide source may be the source of both the calcium ions and the hydroxyl ions. For example, the present invention may comprise a method of producing mineralized enamel, dentin or cementum. The invention may comprise the inclusion of acidic polymers and/or chemical phosphorylation agents as collagen-binding nucleation factors and calcium phosphate-binding apatite stabilizers in a mineralizing solution or gel or direct application of the acidic polymers and/or chemical phosphorylation agents to demineralized dentin to induce an amorphous calcium phosphate nanoprecursor phase that transforms into apatite mineral nanocrystallites within and around the collagen fibrils within these matrices. Also, in certain embodiments, the invention may comprise the use of a slow releasing calcium hydroxide and phosphate source to insure sufficient calcium phosphate production to introduce apatite mineral deposition into collagen matrices and enamel prisms, thereby improving or restoring the physical and mechanical properties of said collagen matrices and enamel prisms.

In other embodiments, the invention may comprise methods of producing mineralized dental tissue where the dental tissue has dental caries and/or been bonded to a restorative material. In one embodiment, the method comprises incubating a site on the dental tissue with a remineralizing restorative material, wherein the remineralizing restorative material comprises a calcium ion source and a hydroxide ion source, wherein the calcium ions and the hydroxide ions are provided at the site of mineralization at a rate suitable to promote the formation of interfibrillar and intrafibrillar apatite crystals within collagen at the site of mineralization. For example, in one embodiment, the restorative material may comprise a polymer resin and/or a cement. In another embodiment, the invention may comprise a method of treating demineralized and/or carious dentin or resin-bonded dentin by applying biomimetic remineralizing restorative materials to damaged hard tissues.

In other embodiments, the present invention comprises methods of treating dental caries in an individual. In one embodiment, the method may comprise incubating a carious site on the dental tissue with a remineralizing restorative material, wherein the remineralizing restorative material comprises a calcium ion source and a hydroxide ion source, wherein the calcium ions and the hydroxide ions are provided at the site of mineralization at a rate suitable to promote the formation of interfibrillar and intrafibrillar apatite crystals within collagen at the site of mineralization. The method may comprise incubating at least one dental tissue with a calcium hydroxide source, a phosphate source, polyphosphate and an acidic polyelectrolyte.

Yet other embodiments of the invention comprise compositions used in the methods of the invention and/or systems (e.g., kits) comprising compositions used in the methods of the invention. For example, in one embodiment, the invention comprises a composition comprising a remineralizing restorative material for producing a mineralized dental tissue, the remineralizing restorative material comprising a calcium ion source and a hydroxide ion source, wherein the calcium ions and hydroxide ions are provided at the site of mineralization at a rate suitable to promote the formation of interfibrillar and intrafibrillar apatite crystals within collagen at the site of mineralization. Other embodiments of the kit of the present invention may comprise a remineralizing restorative material for producing a mineralized dental tissue comprising a calcium ion source and a hydroxide ion source, wherein the calcium and hydroxide are provided at the site of mineralization at a rate suitable to promote the formation of interfibrillar and intrafibrillar apatite crystals within collagen at the site of mineralization, and wherein the remineralizing restorative material is provided in a sealed container with an opening suitable for delivery of the remineralizing restorative material to the site of mineralization, and instructions for use. In some embodiments, the composition may further comprise a collagen-binding nucleation factor, wherein the collagen-binding nucleation factor promotes interaction of the apatite crystals with collagen at the site of mineralization. Also, in some embodiments, the composition may comprise a calcium phosphate-binding apatite stabilizer, wherein the calcium phosphate-binding apatite stabilizer maintains the apatite crystals at a size suitable to form intrafibrillar and interfibrillar crystals at the site of mineralization. In yet other embodiments, the composition may also comprise a phosphate source.

BRIEF DESCRIPTION OF THE DRAWINGS

FIG. 1 shows in accordance with alternate embodiments of the present invention, a schematic illustration of mineralization of dentin tissue in accordance with one embodiment of the present invention.

FIG. 5 shows in accordance with alternate embodiments of the present invention, initial intrafibrillar and interfibrillar remineralization occurring at 2 weeks after phosphoric acid-etched dentin was immersed in the Portland cement-PCF system containing 500 µg/mL of polyacrylic acid and 200 µg/mL of PVPA in accordance with one embodiment of the present invention; Abbreviations: D, demineralized dentin; M, underlying unetched mineralized dentin; $P_r$: partially remineralized dentin.

DETAILED DESCRIPTION

Figure 2A:
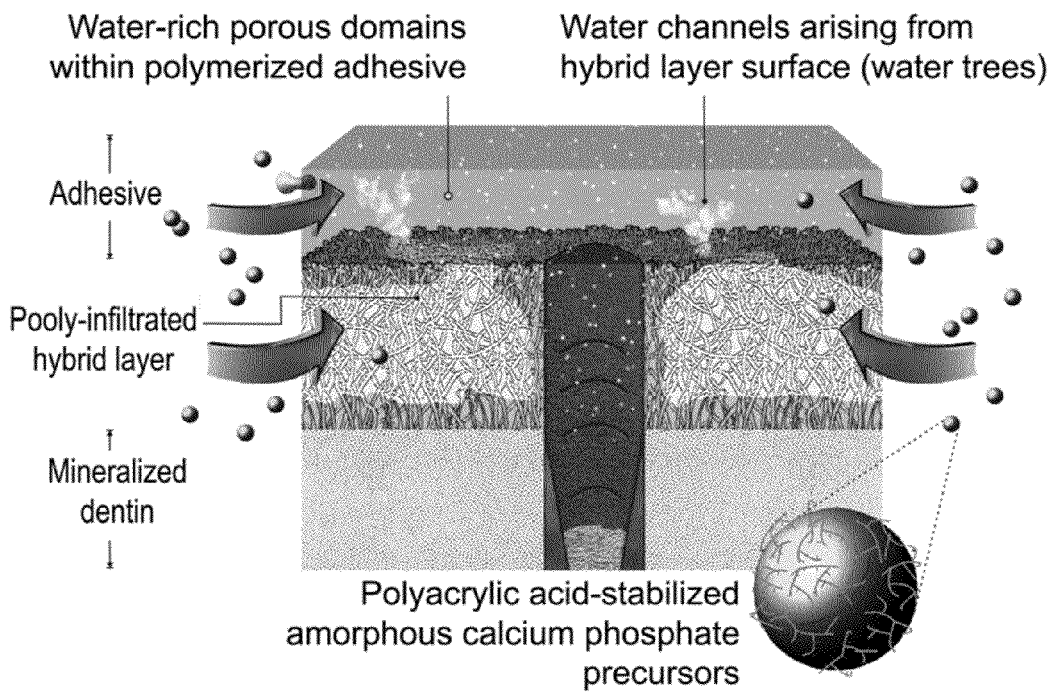
FIG. 2 shows in accordance with alternate embodiments of the present invention, an illustration of biomimetic remineralization of incompletely resin-infiltrated, acid-etched dentin in accordance with alternate embodiments of the present invention, wherein Panel A depicts penetration of polyacrylic acid-stabilized fluidic amorphous calcium phosphate precursors into hybrid layers; Panel B depicts coalescence of the fluidic amorphous nanoprecursors within interfibrillar spaces and voids within the adhesive; Panel C depicts interfibrillar remineralization of resin-bonded dentin; and panel D depicts intrafibrillar remineralization.
Figure 2B:
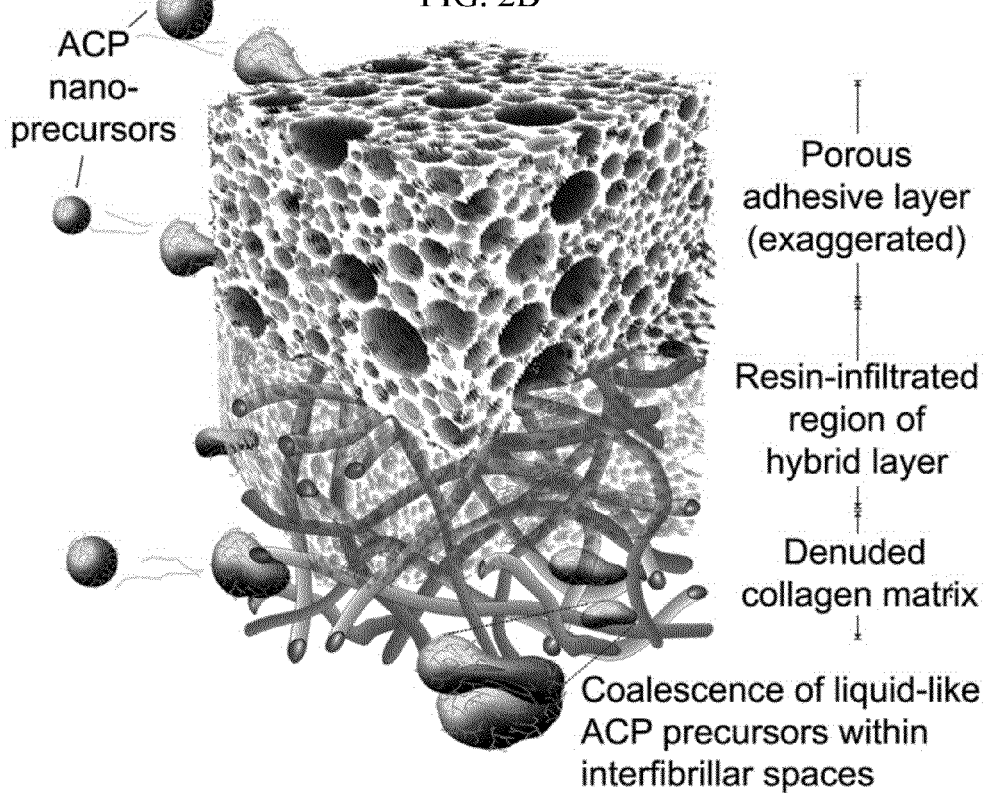

Embodiments of the present invention provide methods of mineralizing dental tissue. Numerous modifications and adaptations are apparent to those skilled in the art without departing from the scope of this disclosure. As set forth above, there is a need for the development of a method of producing mineralized dental tissues where dental caries and treatment of such has resulted in demineralization of dental tissue so as to improve tooth structural integrity and health.

Unless indicated to the contrary, the numerical parameters set forth in the following specification are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

Also, where ranges are provided, it is understood that other embodiments within the specified ranges are to be included.

The following descriptions are meant to clarify, but not limit, the terms defined. If a particular term used herein is not specifically defined, such term should not be considered indefinite. Rather, terms are used within their ordinary meanings.

As used herein, a "subject" or an "individual" may be an animal. For example, the subject or individual may be a mammal. Also, the subject or individual may be a human. The subject or individual may be either a male or a female. The subject or individual may also be a patient, where a patient is an individual who is under dental or medical care and/or actively seeking medical care for a disorder or disease.

As used herein, "dental tissue" is tissue that is derived from, or part of, a tooth. For example, dental tissue may be enamel, dentin or cementum. Enamel is comprised largely of the mineral hydroxylapatite. Dentin generally comprises water, organic and inorganic matter, the latter comprising primarily hydroxylapatite. As defined herein, the organic matter of dentin refers to of type I collagen and non-collagenous proteins. Dentin is a hard structure because its collagenous matrix is generally impregnated with calcium-deficient, carbonate-containing nanometer-sized apatite crystallites [$Ca_{10}(PO_4)_6(OH)_2$]. Calcium and phosphate may account for about 70 wt % of the dry weight of dentin. Type I collagen fibrils account for about 90 wt % of the extracellular matrix of dentin and account for up to 30% of the dry weight of dentin. The collagen fibrils give dentin its flexibility and tensile strength, while the inorganic material gives dentin its compressive strength and rigidity.

As used herein, "hydroxylapatite" or "hydroxyapatite" or "calcium apatite" or "apatites" or "apatite crystals" refers to an inorganic compound that include calcium, hydroxyl residues and phosphate ester residues in a defined stoichiometry. The hydroxylapatite may have the chemical formula $Ca_5(PO_4)_3(OH)$, which is alternatively written $Ca_{10}(PO_4)_6(OH)_2$ to denote that the crystal unit cell comprises two entities. The hydroxylapatite or hydroxyapatite or calcium apatite or apatites may be mammalian in origin. For example, mammalian hydroxylapatite may be a calcium-deficient carbonated apatite with the chemical formula $Ca_5(PO_4CO_3)_6(OH)_2$.

As used herein, "type I collagen" is a long, fibrous structural protein that is present in several different tissues including, but not limited to, dentin, tendon, bone, lung, skin, heart valves, fascia, scar tissue, cornea, and liver. Bundles of collagen fibrils are called collagen fibers. "Tropocollagen" or a "collagen molecule" is a subunit of larger collagen aggregates such as fibrils. Collagen fibrils are composed of individual collagen peptides that self-assemble into triple helical collagen molecules that, in turn, aggregate to form collagen fibrils. The molecules may aggregate with a ¼ overlap to create distinct gaps, sometimes called hole zones.

As defined herein, "type I collagen collagen matrix" or "collagen matrix" refers to native or reconstituted aggregations of type I collagen molecules. The collagen matrix is a fluid-filled (about 70 wt % fluid/30 wt % organic) fibrillar scaffold which is intrinsically soft and generally exhibits a modulus of elasticity of 1 MPa (Maciel et al., *J. Dent. Res.*, 1996, 75:1851-1858; Balooch et al., *J. Biomed. Mater Res.*, 1998, 40:539-544). In dentin, hydroxylapatite may form within the interfibrillar and intrafibrillar spaces of collagen fibrils, which mechanically stiffens the collagen matrix because the apatite crystals have a modulus of elasticity of about 100,000 MPa (Wagner and Weiner, *J. Biomech.*, 1992, 25:1311-1320). The hole zones in collagen fibers may be the location where intrafibrillar mineral crystals initially form, serving as sites of nucleation for further intrafibrillar crystal growth. Type I collagen interfibrillar spaces are approximately 20 nm in width and are very long, while intrafibrillar spaces are approximately 3-4 nm wide and approximately 100 nm long. A number of noncollagenous extracellular matrix proteins are bound to collagen fibrils, including highly phosphorylated anionic proteins such as phosphophoryn and dentin matrix protein 1 (DMP1) that bind to collagen close to the gap zones (Beniash et al., *J. Struct. Biol.*, 2000, 132:212-225; Gajjeraman et al., *J. Biol. Chem.*, 2007, 282:1193-1204; George and Veis, *Chem. Rev.*, 2008, 108:4670-4693).

As used herein, the dental tissue may be mineralized tissue such as, for example, calcified tissue. As used herein, "mineralized tissue" refers to soft, organic extracellular tissues that have been enriched, supported and strengthened by the deposition of inorganic mineral salts that are laid down in a definite hierarchical order within the tissue matrix, resulting in increase in mechanical properties of the tissue. As used herein, "calcified tissue" refers to the accumulation of calcium salts such as calcium carbonate or calcium phosphate within a soft tissue matrix. For example, the term "calcified tissue" or "mineralized tissue" as used herein includes cortical bone, cancellous or medullary bone, tooth enamel, cementum, dentin, and pulp.

As used herein, "demineralized dental tissue" refers to dental tissue that has a diminished amount of hydroxylapatite within the tissue compared to normal dental tissue. For example, demineralized dentin has diminished amounts of hydroxylapatite within the type I collagen matrix. Demineralized dental tissue may be carious dental tissue. Demineralized dental tissue may also be acid-etched dental tissue that has been treated with acid in preparation of creating a filling to treat dental caries.

As used herein, "mineralization" or "remineralization" refers to methods that result in growth of apatite crystallites in and around collagen fibrils in a specific orientation that causes increased stiffness of the collagen matrix comparable to that of sound dentin. The apatite crystals may be about 10-200 nm, 20-100 nm, 30-80 nm or 40-50 nm in length. Methods that cause precipitation of larger crystals of calcium phosphate in dentinal tubules or on dentin surfaces and not in intrafibrillar spaces is not mineralization or remineralization according to the present invention.

As used herein, the term "acid-etched" or "acid etching" refers to the preparation of a tooth prior to dental restorations such as dental fillings and repair of damaged dental tissue using an acidic solution. Acid etching may improve adherence of restorative materials such as, but not limited to, dental resin and dental cement to dental tissue by slightly roughening the tooth surface so as to promote an effective bonding of the applied restorative material or materials. The surface to which the dental restorative is to be applied may be etched with an acidic etching solution for approximately 15-60 seconds, after which the etching solution may be rinsed thoroughly from the dental tissue with water and the surface of the tooth is then dried. Conventional acid etch solutions may contain phosphoric acid at a concentration of approximately 37% to 50% (w/v) in a solution or in a gel compound but may contain a phosphoric acid concentration as low as approximately 0.51% to approximately 5.40% and still achieve appropriate bond strength between the dental tissue and the restorative material. Acid etching may result in demineralization of dental tissue such that a 5-8 μm thick layer of mineral-free collagen matrix is produced on the surface of the mineralized dentin base.

As used herein, the term "restorative material" is used to refer to a material that is adhered to dental tissue to create dental fillings and/or other restorative dental work. Restorative material may be a resin or a cement.

Also, as used herein, a resin-based cement or adhesive is a composition that can be transformed from a non-solid (e.g., liquid or gel) to a solid. The cement or adhesive may include a mixture of comonomers, volatile solvents and fillers. For example, a resin-based adhesive or cement may be a polymer resin, such as an acrylic dental resin cement. For example, a dental cement may be dispensed as a powder and a liquid that is mixed where the powder may be polymethyl methacrylate, a filler, plasticizer, and polymerization initiator, and the liquid monomer may be methyl methacrylate with an inhibitor and/or an activator to control polymerization. Or, other polymers may be used. Polymerization may occur by chemical initiation or light-activation (for example, blue light activation). The resin-based cement or adhesive may have a cement mixture incorporated into it.

As used herein, "cement mixture" refers to a mixture that, when mixed with water, forms a paste that then sets or hardens into a solid cement structure. In certain embodiments, the cement mixture is a calcium silicate and/or calcium phosphate-containing resin cement such that when the cement hardens it releases calcium hydroxide ($Ca(OH)_2$). For example, the cement mixture may be Portland cement. The cement mixture may be incorporated into a resin or filler composition to form a Portland cement-containing resin cement. On hydration, the tricalcium silicate [Eq. (1)] and dicalcium silicate [Eq. (2)] formed during the setting of Portland cement form a porous solid (called, for example, a rigid gel) and release an amorphous calcium silicate hydrate phase ($CaO.2SiO_2.3H_2O$) and calcium hydroxide, thereby providing the calcium ions ($Ca^{2++}$) and the hydroxyl ions ($OH^-$) for calcium phosphate precipitation [Eq. 3] as described in the present invention. Calcium ions and hydroxyl ions released into solution may form calcium hydroxide.

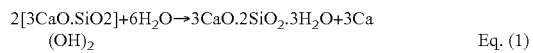 Eq. (1)

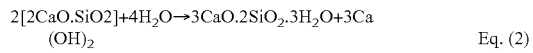 Eq. (2)

 Eq. (3)

As used herein, "bonded" or "bonded to" refers to the interaction of the resin or cement with the dental tissue so as to create a long term adherence. "Bonded" or "bonded to" can therefore refer to the infiltration of resin or cement into the dentin type I collagen matrix and/or the enamel hydroxylapatite structure.

As used herein, a "calcium hydroxide source" refers to a compound that can produce calcium hydroxide and calcium ions and hydroxyl ions over a sufficient period of time and with a slow enough release rate to allow mineralization of demineralized tissue. The calcium hydroxide source may be, but is not limited to, a calcium silicate, a calcium oxalate or a calcium sulfate. Calcium hydroxide cements, polycarboxylate cements, glass ionomer cements and phosphoric acid cements are alternative calcium hydroxide sources. The calcium hydroxide source may be a calcium silicate-containing cement. For example, the calcium hydroxide source may be a cement, where the interaction of the cement with a phosphate-containing solution causes the production of calcium hydroxide, which in turn may result in the production of amorphous calcium phosphate as described in the present invention. The calcium hydroxide source may release calcium hydroxide for a period of at least hours, days, weeks or months. For example, the calcium hydroxide source may produce calcium hydroxide for about 1 hr to about 180 hrs, or about 1 to about 7 days, or about 1 week to about 4 weeks, or about 1 month to about 6 months. The calcium hydroxide source may produce calcium hydroxide at ambient and/or physiological temperatures.

As used herein, "phosphate source" refers to a compound that can produce phosphate ions over a sufficient period of time to allow mineralization of demineralized tissue may. The phosphate source may be a remineralizing cement or phosphate-releasing resin composite that is used to isolate the remineralizing environment from oral fluids and bacteria Alternatively, the phosphate source may be a therapeutic primer or a phosphate-containing buffer.

As used herein, "calcium phosphate-binding apatite stabilizer" is used to refer to a molecule capable of interacting with calcium phosphate in solution and facilitating the formation of apatite nanoprecursors. Further, the calcium phosphate-binding apatite stabilizer may also facilitate recruitment of apatite nanoprecursors to collagen fibrils. The calcium phosphate-binding apatite stabilizer may mimic the function of non-collagenous phosphoproteins that bind to type I collagen in vivo (i.e., act as biomimetic analog). The calcium phosphate-binding apatite stabilizer may act to stabilize formation of apatite nanoprecursors and prevent the formation of large apatite crystals that are too large to enter the collagen fibrillar matrix. The calcium phosphate-binding apatite stabilizer may be a poly(amino) acid polyelectrolyte(or polyanion), including carboxylic acid-containing polyelectrolytes such as, for example, polyacrylic acid (PAA), substituted polymethacrylates (PMA), polysulfonates, phosphorylated proteins, peptides, polymers, sulfated glycoprotein, polyglutamic acid, polyaspartic acid, polyvinyl phosphates, polyvinyl phosphonates, acrylophosphonic acid, polyvinylphosphonic acid, polystrenephosphonic acid, diisopropyl vinyl phosphonate, 1-hydroxyethylidene-1,1-diphosphonic acid, 2-phosphonobutane-1,2,4-tricarboxylic acid and mixtures thereof. Both poly(aspartic) acid and polyacrylic acid have been employed as biomimetic analogs of acidic non-collagenous proteins such as dentin matrix protein 1 (DMP1) (He, G. et al., *Biochemistry*, 2005, 44:16140-16148). for stabilizing and controlling the dimensions of amorphous phases in calcium carbonate and calcium phosphate precipitation systems (Olszta, M. J. et al., *Connect Tissue Res.*, 2003, 44 (Suppl 1):326-334; US Patent Application 2006/0204581).

As used herein, "apatite nanoprecursors" refers to a metastable amorphous hyrdroxylapatite precursor (i.e., amorphous calcium phosphate) that may be involved in the natural mineralization process of dental tissues.

As used herein, "collagen-binding nucleation factor" is used to refer to a molecule capable of both interacting with type I collagen and facilitating apatite crystal formation within the collagen matrix. The collagen-binding nucleation factor may mimic the function of non-collagenous phosphoproteins that bind to type I collagen in vivo (i.e., act as biomimetic analog). The collagen-binding nucleation factor may facilitate recruitment of calcium-phosphate nanoprecursors and associated calcium phosphate-binding apatite stabilizers to collagen fibrils. The collagen-binding nucleation factor may be a phosphorylating agent. For example, the collagen-binding nucleation factor may be a polyelectrolyte, including, for example, polyphosphates such as polyvinylphosphonic acid (PVPA). PVPA is a polyelectrolyte that has been employed as a biomimetic analog for phosphoproteins such as DMP-1 and dentin phosphoprotein (He, J. et al., *J. Biol. Chem.*, 2005, 280:33109-33114; Olszta, M. J. et al., *Connet. Tissue Res.*, 2003, 44 (Suppl. 1):326-334; U.S. Pa. Appl. No. 2006/0204581; He, G. et al., *Biochem.*, 2005, 44:16140-16148). PVPA is a water-soluble polymer with a molecular weight of 24,000 g/mole (Bingöl et al., 2006). Unlike natural phosphorylated NCPs, where the phosphate group is esterified to amino acids and hence is susceptible to phosphatases in body fluids, polyphosphonic acid is long lasting because the P—C—P bond it is not susceptible to esterases. PVPA may act as a biomimetic equivalent to phosphorphoryn, DMP-1, osteopontin, osteonectin and dentin sialoprotein. In an alternate embodiment, the collagen-binding nucleation factor may be casein phosphopeptide, a polyphosphate (e.g., sodium tetrametaphosphate, sodium trimetaphosphate, sodium tripolyphosphate, tetrasodium pyrophosphate and sodium hexametaphosphate), phosphoric anhydride, phosphorous oxychloride, L-ascorbic acid 2-phosphate trisodium salt and phosphoramidites. Sodium trimetaphosphate may be used for remineralization (Li, X. and Chang, J., *J. Biomed. Mater. Res. A.*, 2008, 85:293-300). In preferred embodiments, collagen-binding nucleation factor may be PVPA or sodium trimetaphosphate. In other embodiments, the collagen-binding nucleation factor may be an anion-rich biomolecule, such as phosphophoryn, phosvitin or casein phosphopeptide, Collagen-binding nucleation factors, however, generally do not include phosphoric acid esters (Mai, S. et al, *Dent. Mater.*, 2009, 25:1230-1239).

As used herein, the terms "chemical phosphorylation" and "phosphate derivatization" shall be understood to refer to the grafting of a phosphate group to the amino acid moieties of a collagen molecule via the formation of a covalent bond so that the resultant phosphate group is not reversibly displaced by the introduction of an ionic salt such as sodium chloride.

As used herein, graft diblock and amphiphilic triblock copolymers are molecules that can function as both a collagen-binding nucleation factor and a calcium-phosphate-binding apatite stabilizer. For example, such molecules may include, but are not limited to, poly(acrylic acid-co-vinyl phosphonic acid), poly(aspartic acid-co-vinyl phosphonic acid), poly(methacrylic acid-co-vinyl phosphonic acid), poly(acrylic acid-co-vinyl aminomethylene phosphonic acid), poly[acrylic acid-co-bis(2-chloroethyl) vinylphosphonate], poly[acrylic acid-co-1-hydroxyethylidene-1,1-diphosphonic acid], and poly[aspartic acid-co-bis(2-chloroethyl) vinylphosphonate.

As used herein, the term "interact" refers to a condition of proximity between one molecule, or portions or fragments thereof, and another molecule, or portions thereof. The interaction may be non-covalent, for example, as a result of hydrogen-bonding, van der Waals interactions, or electrostatic or hydrophobic interactions. For example, molecules that may interact in the present invention are the calcium phosphate-binding apatite stabilizer with the apatite nanoprecursors; the collagen-binding nucleation factor with the type I collagen molecules in dental tissue; the calcium phosphate-binding apatite stabilizer-bound apatite nanoprecursors with the collagen-binding nucleation factor; and the calcium phosphate-binding apatite stabilizer-bound apatite nanoprecursors with the type I collagen molecules in dental tissue.

As used herein, the term "remineralizing restorative material" refers to a composition comprising compounds that allow for the formation of intrafibrillar and interfibrillar deposition of apatite crystals within the collagen matrix of dentin as the demineralized tissue substrate. In an embodiment, the restorative material may comprise a source of calcium ions, hydroxyl ions and/or calcium hydroxide. In some embodiments, the remineralizing restorative material may also comprise a collagen-binding nucleation factor, a calcium phosphate-binding apatite stabilizer and/or a phosphate source. The remineralizing restorative material may also comprise a resin and/or cement. The "remineralizing restorative material" may be used for the delivery of biologically active agents (i.e., biomimetic analogs) incorporated as an additive to the remineralizing restorative material. In an embodiment of the present invention, the resin comprises a calcium hydroxide source, a phosphate source, a calcium phosphate-binding apatite stabilizer and a collagen-binding nucleation figure. In certain embodiments, the remineralizing restorative material may comprise a liquid, a gel or a paste containing bioactive filler particles that seal a caries in a tooth from saliva and bacteria in the oral environment after polymerization of the resin component. This provides a controlled microenvironment in the tooth.

As used herein, biologically active agents may include, but are not limited to, matrix metalloproteinase (MMP) inhibitors, antimicrobial agents, growth factors, angiogenic factors, and other healing agents. Examples of growth agents include, but are not limited to, bone growth factor (BMP)/osteogenic protein-1 (OP-1), basic or acidic fibroblast growth factor (bFGF, aFGF), nerve growth factor (NG-F), epidermal growth factor (EGF), insulin-like growth factors 1 and 2 (IGF-1, IGF-2), platelet-derived growth factor (PDGF), vascular endothelial growth factor (VEGF), transforming growth factors alpha and beta ($\mu$GF-a, $\mu$GF-13) and interleukins.

Biomineralization of Dental Tissue

The methods of the present invention are described herein with primary reference to the dental industry but may be used for mineralization and/or remineralization of other types of tissue.

In an embodiment, the present invention comprises compositions for producing a mineralized (or remineralized) tissue. In one embodiment, the composition may comprise a remineralizing restorative material for producing a mineralized dental tissue, the remineralizing restorative material comprising a calcium ion source and a hydroxide ion source. In an embodiment, the calcium ions and the hydroxide ions are provided at the site of mineralization at a rate suitable to promote the formation of interfibrillar and intrafibrillar apatite crystals within collagen at the site of mineralization.

In certain embodiments, the compositions of the present invention are provided as kits. For example, in certain embodiments, the present invention comprises a kit comprising: a remineralizing restorative material for producing a mineralized dental tissue comprising a calcium ion source and a hydroxide ion source, wherein the calcium ions and the hydroxide ions are provided at the site of mineralization at a rate suitable to promote the formation of interfibrillar and intrafibrillar apatite crystals within collagen at the site of mineralization, and wherein the remineralizing restorative material is provided in a sealed container with an opening suitable for delivery of the remineralizing restorative composition to the site of mineralization; and instructions for use.

In yet other embodiments, the present invention comprises methods of producing a mineralized dental tissue. The methods may comprise incubation of a site on the dental tissue with a remineralizing restorative material, wherein the remineralizing restorative material comprises a calcium ion source and a hydroxide ion source, wherein the calcium ions and the hydroxide ions are provided at the site of mineralization at a rate suitable to promote the formation of interfibrillar and intrafibrillar apatite crystals within collagen at the site of mineralization. For example, in certain embodiments, the present invention comprises methods of treating dental caries in an individual comprising incubation of a carious site on the dental tissue with a remineralizing restorative material, wherein the remineralizing restorative material comprises a calcium ion source and a hydroxide ion source, wherein the calcium ions and the hydroxide ions are provided at the site of mineralization at a rate suitable to promote the formation of interfibrillar and intrafibrillar apatite crystals within collagen at the site of mineralization.

The following non-limiting description applies to each of the compositions, kits and methods of the present invention.

As described in detail herein, to form apatite crystals, calcium ions, hydroxide ions, and phosphate must be present at the site of mineralization. In certain embodiments, the remineralizing restorative material further comprises a phosphate source. Or, phosphate may be provided to the site of mineralization as an additional component. For example, the phosphate source may be provided by saliva or other body fluids, by a physiologically acceptable phosphate-containing solution (e.g., a phosphate-containing buffer or saline-like wash), or by a cement or resin that may be included as part of the remineralizing restorative material. For example, in alternate embodiments, the phosphate source may comprise a remineralizing cement, phosphate-releasing resin composite, a phosphate-containing buffer or a therapeutic primer.

As described in more detail herein, deposition of apatite crystals at the site of mineralization may be controlled such that the crystals form within and around collagen fibrils. Thus, in certain embodiments, the remineralizing restorative material may further comprise a collagen-binding nucleation factor, wherein the collagen-binding nucleation factor promotes interaction of the apatite crystals with collagen at the site of mineralization. The collagen-binding nucleation factor may comprise a polyanion. For example, in alternate embodiments, the collagen-binding nucleation factor may comprise at least one of polyvinylphosphonic acid, sodium tetrametaphosphate, sodium trimetaphosphate, sodium tripolyphosphate, tetrasodium pyrophosphate, sodium hexametaphosphate, or phosvitin. Or, combinations of these compounds may be used. Or, other components may be included as described herein.

As described in more detail herein, deposition of apatite crystals at the site of mineralization may be controlled such that the crystals are limited to a size that is small enough to form within and around collagen fibrils. Thus, in certain embodiments, the remineralizing restorative material further comprises a calcium phosphate-binding apatite stabilizer, wherein the calcium phosphate-binding apatite stabilizer maintains the apatite crystals at a size suitable to form intrafibrillar and interfibrillar apatite crystals at the site of mineralization. The calcium phosphate-binding apatite stabilizer may, in certain embodiments, comprise a polyanion. In certain embodiments, the calcium phosphate-binding apatite stabilizer may comprise at least one of polyacrylic acid, a substituted polymethacrylate, a phosphorylated protein, a peptide, a polymer, a sulfated glycoprotein, a polyglutamic acid, a polyaspartic acid, a polyvinyl phosphate, a polyvinyl phosphonate, an acrylophosphonic acid, a polyvinylphosphonic acid, a polystrenephosphonic acid, a diisopropyl vinyl phosphonate, 1-hydroxyethylidene-1,1-diphosphonic acid, 2-phosphonobutane-1,2,4-tricarboxylic acid. Or, combinations of these compounds may be used. Or, other components may be included as described herein.

In certain embodiments, the calcium phosphate-binding apatite stabilizer and a collagen-binding nucleation factor are provided as a single biomimetic entity. In this embodiment, the single biomimetic entity comprises poly(acrylic acid-co-vinyl phosphonic acid), poly(aspartic acid-co-vinyl phosphonic acid), poly(methacrylic acid-co-vinyl phosphonic acid), poly(acrylic acid-co-vinyl aminomethylene phosphonic acid), poly[acrylic acid-co-bis(2-chloroethyl) vinylphosphonate], poly[acrylic acid-co-1-hydroxyethylidene-1,1-diphosphonic acid] or poly[aspartic acid-co-bis(2-chloroethyl) vinylphosphonate. Or, combinations of these compounds may be used. Or, other components may be included as described herein.

In some embodiments, the remineralizing restorative material may comprise a resin. Suitable resins may comprise resins that are employed as filling material for repairing regions of tooth decay such as those described herein and/or otherwise known in the art. In certain embodiments, the resin may function at least in part to isolate the site of remineralization from the surrounding environment.

In some embodiments, the source of at least one of the calcium ions, hydroxide ions and phosphate is a cement. For example, a cement that comprises at least one of calcium silicate, calcium oxalate, calcium sulfate, calcium hydroxide, a polycarboxylate, a glass ionomer, or phosphoric acid may be used. In one embodiment, a cement such as Portland Cement may be used.

In certain embodiments, the remineralizing restorative material may comprise a first component comprising the source of calcium ions and hydroxide ions and a second component containing at least one of a collagen-binding nucleation factor or a calcium phosphate-binding apatite stabilizer. For example, in some cases the site of mineralization is first exposed to at least one of a collagen-binding nucleation factor or a calcium phosphate-binding apatite stabilizer, wherein the collagen-binding nucleation factor promotes interaction of apatite crystals with collagen at the site of mineralization, wherein the calcium phosphate-binding apatite stabilizer maintains the apatite crystals at a size suitable to form as intrafibrillar and interfibrillar crystals at the site of mineralization, followed by incubation with the source of at least one of calcium ions, hydroxide ions or phosphate. This may allow the at least one of a collagen-binding nucleation factor or a calcium phosphate-binding apatite stabilizer to interact with the collagen fibrils at the site of mineralization. In this embodiment, the source of phosphate is included in either the first component, or the second component, or as a third (e.g., separate) component.

The remineralizing restorative material may be formulated so as to be easily applied to a tooth in a subject's mouth. In alternate embodiments, the remineralizing restorative material may be formulated as a gel or paste that can be applied to a tooth that has been prepared for mineralization or remineralization. Or, the remineralizing restorative material may be applied as a liquid that subsequently gels or solidifies in situ.

Or, the remineralizing restorative material may be applied in any form (e.g., liquid, gel, paste or solid) and then the site of remineralization protected from the environment by a physical protective element (e.g., a plastic cap or the like).

In certain embodiments, the site of mineralization is maintained within a defined pH range. In alternate embodiments, the site of remineralization is maintained at a pH ranging from about 8.0 to 11.5, or 8.5 to 11.0, or 9.0 to 10.5, or 9.0 to 10.0 or 9.0 to 9.5. Or, ranges within these ranges (e.g., 9.0 to 11.5) may be used.

In certain embodiments, the dental tissue comprises demineralized dentin. Or, the dental tissue may comprise enamel or cementum. Also in certain embodiments, mineralization is performed to repair the carious tissue at the site of mineralization. In certain embodiments, the carious tissue is acid-etched. For example, in certain embodiments, the present invention comprises methods of treating dental caries in an individual comprising incubation of a carious site on the dental tissue with a remineralizing restorative material, wherein the remineralizing restorative material comprises a calcium ion source and a hydroxide ion source, wherein the calcium and hydroxide are provided at the site of mineralization at a rate suitable to promote the formation of interfibrillar and intrafibrillar apatite crystals within collagen at the site of mineralization.

Thus, in one embodiment, the invention comprises methods of producing mineralized dental tissue. The method may comprise incubating at least one tissue with a calcium hydroxide source, a phosphate source, a collagen-binding nucleation factor and a phosphate-binding apatite stabilizer.

In other embodiments, the invention also may comprise methods of treating dental caries in an individual. The method may comprise incubating at least one dental tissue with a calcium hydroxide source, a phosphate source, a collagen-binding nucleation factor and a phosphate-binding apatite stabilizer.

In other embodiments, the invention may comprise methods of producing mineralized dental tissue where the dental tissue has dental caries and/or has been bonded to a restorative material. For example, in one embodiment, the restorative material may comprise a calcium hydroxide source and a phosphate source with biomimetic analogs such as at least one collagen-binding nucleation factor and at least one calcium phosphate-binding apatite stabilizer to promote intrafibrillar and interfibrillar deposition of apatite crystals.

Each of the various embodiments described herein may apply to the methods, compositions and systems of the present invention.

In some embodiments, the collagen-binding nucleation factor may comprise a polyphosphate. In an embodiment, the phosphate-binding apatite stabilizer may be an acidic polyelectrolyte.

In some embodiments, the tissue is a dental tissue. For example, the dental tissue may comprise, in alternate embodiments, at least one of enamel, dentin or cementum. In some embodiments, the dental tissue comprises at least partially demineralized dental tissue. For example, the dental tissue may comprise carious dental tissue. In other embodiments, the dental tissue may comprise acid-etched dental tissue, including, for example, dental tissue that has been bonded to a resin, such as, but not limited to, a polymer resin.

As described in more detail below, in many applications the dental tissue will comprise dentin. However, the methods, compositions, and systems of the present invention may also be used for mineralization or remineralization of enamel. In some cases, mineralization of dental caries in enamel can often be more easily achieved because enamel is found on the surface of teeth in a relatively thin layer. Also, enamel lacks a collagen fibril matrix. Still, current approaches may not allow for the deposition of small crystals on the enamel surface so as to achieve the appearance of normal enamel. Using the methods, compositions and systems of the present invention, such smaller crystals can be achieved. Enamel has a different protein matrix scaffold than the dentin collagenous matrix. If that scaffold is not destroyed and if crystallites are not completely dissolved, apatite deposition over existing crystallites may be achieved through the process of epitaxial deposition (i.e., heterogeneous crystallization. Epitaxial deposition of mineral uses the existing crystalline lattice as a pattern or model. A layer of calcium and phosphate ions line up on the lattice and are converted from the liquid phase to a solid crystal phase. This may be repeated thousands of times to grow the crystalline solid thicker and thicker. No scaffold is required inepitaxial mineralization. Epitaxial growth of crystals is generally more dependent on the ion products of calcium and phosphate exceeding the solubility product constant (Ksp) of apatite. However, it is not possible to processes known in the art for homogeneous crystallization (i.e., without the use of seed hydroxyapatite crystallites). Thus, the methods, compositions and systems of the present invention may permit homogenous remineralization of enamel whereas other known systems may not.

In some embodiments, the calcium hydroxide source may produce calcium hydroxide or calcium ions or hydroxyl ions at a predetermined level. For example, in alternate embodiments, the amount of calcium hydroxide produced may comprise a concentration of at least $5 \times 10^{-5}$ moles/L for a period of at least days, weeks or several months. In other embodiments, the calcium hydroxide produced by the calcium hydroxide source interacts with phosphate present at the site of remineralization and NCP analogs (e.g., collagen-binding nucleation factor and calcium phosphate-binding apatite stabilizer) to produce amorphous calcium phosphate. In some embodiments, the ratio of the phosphate-containing solution and NCP analogs to the calcium hydroxide source may provide sufficient phosphate ions and NCP analogs to maintain amorphous calcium phosphate at nanoscopic dimensions. In some embodiments, the phosphate source and NCP analogs are provided as part of the remineralizing restorative material. In alternate embodiments, the ratio of the remineralization medium to cement mixture may be between 3:1 to 10:1.

In an embodiment, the calcium hydroxide source may comprise a cement mixture. The cement mixture may contain calcium silicate, such that upon hydration the cement hardens as an amorphous calcium silicate hydrate and calcium hydroxide is released. For example, the calcium hydroxide source may comprise Portland cement. Portland cement is the active ingredient of Mineral Trioxide Aggregate (Dentsply Tulsa, Tulsa, Okla., USA), and is a bioactive cement that has been used extensively in dentistry for stimulating dentinogenesis and cementogenesis (Sarkar, N. K. et al., *J. Endod.*, 2005, 31:97-100; Ford, T. R. et al., *J. Am. Dent. Assoc.*, 1996, 127:1491-1494. X-ray diffraction and Fourier transform infrared spectroscopy experiments have shown that set (hardened) Portland cement releases calcium hydroxide that interacts with the remineralization medium (i.e., phosphate-containing fluid (PCF) or simulated body fluid (SBF)) to produce calcium-deficient apatites via an amorphous calcium phosphate phase (Tay, F. R. et al., *J. Endod.*, 2007, 33:1347-1351).

In an alternate embodiment, the calcium hydroxide source may comprise a calcium phosphate-containing resin cement. A number of calcium phosphate-containing resins are contemplated within the scope of this invention, for example, including, but not limited to, those described in U.S. Pat. No. 6,398,859, which is incorporated herein by reference.

In certain embodiments, the calcium hydroxide source comprises a remineralizing restorative material composite, wherein the composite comprises a resin matrix and at least one filler. For example, the filler may comprise a Portland cement powder filler particle and a tricalcium phosphate filler.

In various embodiments, the methods, compositions and kits used in the method comprise a phosphate source. The phosphate may be present in amounts so as to interact with the calcium provided by the calcium hydroxide source to form calcium phosphate nanoprecursors as described in more detail below. The phosphate source may comprise a phosphate-containing solution or resin paste. In alternate embodiments, the phosphate source provides phosphate at a concentration of about at least 1 µM, or 10 µM, or 100 µM, or 1 mM or 10 mM at the site of remineralization. Or, other concentrations may be used, depending upon the nature of the remineralization desired. In alternate embodiments, the calcium hydroxide source provides calcium ions and/or hydroxyl ions at a concentration of about at least 1 µM, or 10 µM, or 100 µM, or 1 mM or 10 mM at the site of remineralization. Or, other concentrations may be used, depending upon the nature of the remineralization desired.

In some embodiments, and as described below, it may be important to control the pH at the site of mineralization or remineralization. In certain embodiments, mineralization of dentin proceeds most rapidly at pH 9.0-9.5. In a preferred embodiment, the pH is at least 9.5). The bicarbonate buffer system of saliva generally has a functional pKa of 6.8 (i.e., its major buffering capacity spans plus or minus 1 pH unit around the pKa, or 5.8-7.8). In some embodiments, remineralizing restorative material may be used to create a microenvironment maintaining a pH of at least 9.5 for a period of at least 6 months. In some embodiments, when applied to demineralized dentin, the remineralizing restorative material may isolate/sequester the demineralized dentin from the oral environment, sealing the sites of dentin remineralization from oral fluids that would dilute and buffer the high pH (>pH 9.0) required for rapid remineralization. For example, the sealing of the sites of dentin remineralization using remineralizing restorative material may cause the concentrations of calcium and hydroxyl ions and phosphate to be maintained as constants for several months. In some embodiments, the remineralizing restorative material sequesters the sites of dentin remineralization by bonding to surrounding normal mineralized dental tissues. In certain embodiments, the portion of the remineralizing restorative material exposed to the demineralized dentin releases calcium ions and hydroxyl ions, either with or without also releasing phosphate ions, into the demineralized microenvironment that exists between the remineralizing restorative material and the normal underlying mineralized tissue.

In various embodiments of the present invention, the collagen-binding nucleation factor may comprise a polyphosphate. For example, the polyphosphate may comprise polyvinyl phosphonic acid. In alternate embodiments, the polyphosphate concentration may comprise a concentration at the site of mineralization or remineralization of about 20-2,000 µg/mL, or 50-1,000 µg/mL, or 100-500 µg/mL, or about 200 µg/mL.

In other embodiments, the collagen-binding nucleation factor may comprise a chemical phosphorylation agent. For example, the chemical phosphorylation agent may comprise sodium trimetaphosphate, sodium tetrametaphosphate, sodium trimetaphosphate, sodium tripolyphosphate, tetrasodium pyrophosphate and sodium hexametaphosphate. In at least certain embodiments, polymerized phosphoric acid esters, such as those found, for example, in XP Bond and Adper Prompt L-Pop resins, are not effective as the polyphosphate nucleation factors (unpublished results). In a preferred embodiment, the chemical phosphorylation agent comprises sodium trimetaphosphate. In alternate embodiments, the chemical phosphorylation agent concentration may comprise a concentration at the site of mineralization or remineralization of about 0.1-10% or 0.5-5% or 1-3%. Or other concentrations may be used.

In alternate embodiments, the collagen-binding nucleation factor may comprise an anion-rich biomolecule. For example, the anion-rich biomolecule may comprise a biomolecule selected from the group consisting of phosphophoryn, phosvitin and casein phosphopeptide.

In other embodiments, the collagen-binding nucleation factor and the calcium phosphate-binding apatite stabilizer may comprise a single biomimetic entity. In some embodiments, the collagen-binding nucleation factor and the calcium phosphate-binding apatite stabilizer may comprise two separate chemical entities linked together into a single biomimetic entity via a spacer. For example, the collagen-binding nucleation factor and the calcium phosphate-binding apatite stabilizer may comprise poly(acrylic acid-co-vinyl phosphonic acid), poly(aspartic acid-co-vinyl phosphonic acid), poly(methacrylic acid-co-vinyl phosphonic acid), poly(acrylic acid-co-vinyl aminomethylene phosphonic acid), poly[acrylic acid-co-bis(2-chloroethyl) vinylphosphonate], poly[acrylic acid-co-1-hydroxyethylidene-1,1-diphosphonic acid] or poly[aspartic acid-co-bis(2-chloroethyl) vinylphosphonate.

In one embodiment, the calcium phosphate-binding apatite stabilizer may comprise a carboxylic acid-containing polyelectrolyte. In some embodiments, the carboxylic acid-containing polyelectrolyte may comprises a polyelectrolyte selected from the group consisting of polyacrylic acid, poly(aspartic) acid, poly(acrylic acid-co-vinyl phosphonic acid), poly(aspartic acid-co-vinyl phosphonic acid), poly(methacrylic acid-co-vinyl phosphonic acid), poly(acrylic acid-co-vinyl aminomethylene phosphonic acid), poly[acrylic acid-co-bis(2-chloroethyl) vinylphosphonate], poly[acrylic acid-co-1-hydroxyethylidene-1,1-diphosphonic acid], and poly[aspartic acid-co-bis(2-chloroethyl) vinylphosphonate. In some embodiments, the calcium phosphate-binding apatite stabilizer may be an amino acid, such as, for example, glycine or glutamic acid. In some embodiments, polyelectrolyte comprises polyacrylic acid or poly(aspartic) acid. For example, in some embodiments, the polyelectrolyte may comprise polyacrylic acid. In an embodiment, the polyacrylic acid may comprise a molecular weight of 1000-6000 Daltons (Da). For example, in one embodiment, polyacrylic acid may comprise a molecular weight of 1800 Da.

In certain embodiments, the concentration of the calcium phosphate-binding apatite stabilizer is provided at a defined concentration at the site of mineralization or remineralization. For example, in various embodiments, the concentration of the calcium phosphate-binding apatite stabilizer ranges from about 50-5,000 µg/mL, or 75-1,000 µg/mL, or 100-750 µg/mL, or about 100-500 µg/mL, or about 100-200 µg/mL. In one embodiment, polyacrylic acid is used at a concentration comprising 500-1000 µg/mL. In other embodiments, polyacrylic acid is used at a lower concentration (e.g., about 100-200 µg/mL)

In certain embodiments, the mineralization (or remineralization) comprises the deposition of apatite crystals in the intrafibrillar and interfibrillar spaces of type I collagen fibrils present within dental tissue. In one aspect, the apatite crystals initially formed during mineralization may comprise apatite crystals small enough to fit in the intrafibrillar and interfibrillar spaces of type I collagen fibrils present within the dental tissue. In some embodiments, the apatite crystals initially formed during the mineralization process may comprise apatite crystals that are about 5-500 nm, or 20-200, or about 40-75 nm in length and width and about 1-100 nm, or 5-20 nm in thickness. Or, ranges within these ranges may be used. In other embodiments, the apatite crystals may comprise apatite crystals whose c-axis aligns along the longitudinal axis of the type I collagen fibrils within the dental tissue.

The remineralization may provide a predefined amount of mineralization of the tissue. In alternate embodiments, mineralization of the dental tissues may comprise about at least 30%, or at least 40%, or at least 50%, or at least 60%, or at least 70%, or at least 80%, where 100% is defined as the level stiffness or mineralization of the tissue prior to demineralization (e.g., by cavities or acid etching or both). In one embodiment, mineralization of the dental tissue is about 80-100%. Or, ranges within these ranges may be used.

In some embodiments, remineralization of resin-bonded dentin may comprise the deposition of apatite crystals in the water-filled voids and channels that may be present in the hybrid layer of the resin-bonded dentin due to incomplete infiltration of the resin into the demineralized dentin. For example, in some embodiments, during the acid-etching phase of resin bonding, the surface 5-10 µm of mineralized dentin may be completely demineralize, leaving about 30 vol % collagen fibril matrix floating in about 70 vol % water. In certain embodiments, during the resin infiltration phase of dentin bonding, solvated liquid comonomers of dental resins/adhesives may diffuse into the 70 vol % water in an attempt to replace all of the water with solvated comonomers where, after evaporation of the volatile solvent, the comonomers are light-cured into polymers. In some embodiments, the resins may have displaced most of the water but about 2-3% residual water-filled voids and channels may remain unsealed by resin and provide diffusion pathways for water uptake and outward elution of unpolymerized monomers. Thus, in certain embodiments, remineralization of demineralized dentin that is unsealed by resin may be remineralized by deposition of apatite crystals in the water-filled voids and channels, thereby creating a perfect seal between the resin and the dentin. In some embodiments, the mineralization of these water-filled voids and channels to about 80-100% may improve long-term durability of resin-dentin bonds.

The mineralization and/or remineralization may be occur over a defined temperature range. In alternate embodiments, the mineralization and/or remineralization may be occur within a temperature range of about 10-40° C., or 20-37° C., or 25-37° C. Or, ranges within these ranges may be used. In a preferred embodiment, the temperature used may be between about 33° C. and 37° C.

The mineralization and/or remineralization may occur over a defined period of time. In alternate embodiments, the mineralization and/or remineralization may be occur over 1 hr to about 6 months, or about 3 hours to about 2 months, or about 5 hours to about 2 months, or about 12 hours to about 1.5 months, or about 1 day to about 1 month, or about 1 week to about 4 weeks, or about 2 to 3 weeks. Or, ranges within these ranges may be used.

In some embodiments, the remineralizing restorative material may comprise a resin-based composite containing at least one filler. For example, the resin of the composite may be a hydrophilic resin. In certain embodiments, the hydrophilic resin absorbs water and swells, which increases the permeability of the resin-based composite matrix so that water-induced calcium and phosphate ions from Portland cement fillers can diffuse out of the resin composite into the underlying demineralized dentin. In certain embodiments, the filler may comprise at least one calcium phosphate powder with unpolymerized resin comonomer blends in varying proportions as fillers. Calcium phosphate powders may include, for example, dicalcium phosphate dehydrate, tricalcium phosphate, tetracalcium phosphate, octacalcium phosphate. For example, in some embodiments, remineralizing restorative material comprising at least one calcium phosphate powder as a filler may slowly release calcium and phosphate ions from the resin composite into the underlying demineralized dentin after the resin composite has polymerized and water sorption has occurred. In one embodiment, the remineralizing restorative material comprises a tricalcium phosphate-containing resin composite releases calcium and phosphate ions into the remineralization site of the dentin and is capable of raising the pH of the remineralization site to at least 9.5.

Thus, embodiments of the present invention comprise methods, compositions, and systems for biomineralization of tissue. FIG. 1 shows an example of a method of producing mineralized dental tissue in accordance with an embodiment of the present invention. As illustrated in FIG. 1, the method may use a combination of a calcium hydroxide source, a phosphate source, a collagen-binding nucleation factor and a phosphate-binding apatite stabilizer and may comprise the steps of nanoprecursor induction (Phase I: panels A-D), controlled nanoprecursor recruitment (Phase II: panels E-F) and mescoscopic assembly of apatite crystals within the collagen matrix of dentin (Phase III: panels G-H). In one embodiment, the collagen-binding nucleation factor may be polyvinylphosphonic acid and the phosphate-binding apatite stabilizer may be polyacrylic acid.

For example, in one embodiment, nanoprecursor induction may occur with the addition of the calcium hydroxide source to the phosphate source in the presence of the calcium phosphate-binding apatite stabilizer to produce metastable amorphous calcium phosphate nanoprecursors (FIG. 1A) that are small enough to penetrate a demineralized collagen matrix (FIG. 1B). These metastable amorphous calcium phosphate nanoprecursors may have the potential to be transformed into apatite nanocrystals (FIG. 1C), which can be stabilized by the phosphate-binding apatite stabilizer (FIG. 1D). The calcium phosphate-binding apatite stabilizer interacts with metastable amorphous calcium phosphate nanoprecursors in solution, stabilizing their formation and restricting the size of the apatite nanocrystals formed. This step may occur irrespective of whether collagen-binding nucleation factor is present but, in the absence of collagen-binding nucleation factor, there may very limited attraction of these nanoprecursors into the demineralized collagen matrix.

Controlled nanoprecursor recruitment may occur with the further addition of the collagen-binding nucleation factor. The collagen-binding nucleation factor functions to promote apatite nanoprecursor attraction and recruitment within the collagen matrix. The collagen-binding nucleation factor is immobilized along the collagen microfibrils as well as on the surface of the collagen fibrils in a manner that is analogous to the interaction between natural dentin non-collagenous proteins (NCP) and collagen (FIG. 1E). As apatite nanocrystals are deposited within the collagen fibrils, they may appear corrugated, revealing the periodicity of the fibril. Thus, in one embodiment, apatite nanocrystals are directed by the immobilized collagen-binding nucleation factor to orientate along the microfibrils (intrafibrillar remineralization) and the surface of the collagen fibrils (interfibrillar remineralization)

(FIG. 1F). The nanocrystals that are initially deposited may be much smaller than the apatite platelets found in natural intact human dentin and may act as the primary building units in dentin remineralization.

Mesoscopic assembly of apatite crystals within the collagen matrix of dentin may then result from the PVPA-anchored nanocrystals guiding other apatite nanocrystals to orientate by self-assembly, resulting in large polymer-stabilized mesocrystals. These mesocrystals may eventually transform via a particle-mediated, "non-classical crystallization mechanism" (FIG. 1G) into larger apatite platelets within and along the surface of the collagen fibrils (FIG. 1H). These large apatite platelets may closely resemble those found in human enamel and hypermineralized dentin, and exhibit definitive evidence of mesoscopic assembly from apatite nanocrystals (TEM insert, FIG. 1H).

FIG. 2 shows an alternate embodiment of the present invention, wherein the method of producing mineralized dental tissue is used to remineralize incompletely resin-infiltrated, acid-etched dental tissue. As illustrated in FIG. 2, the method may use a combination of a calcium hydroxide source, a phosphate source, a collagen-binding nucleation factor and a phosphate-binding apatite stabilizer and comprise the steps of: (1) penetration of polyacrylic-acid-stabilized amorphous calcium phosphate precursors into hybrid layers via the resin-sparse, collagen-rich regions, as well as potentially porous regions within the adhesive layer (FIG. 2A); (2) coalescence of the fluidic amorphous nanoprecursors within interfibrillar spaces and voids within the adhesive (FIG. 2B); (3) interfibrillar remineralization with diffusion of polyvinylphosphonic acid molecules into the denuded collagen matrix where they attach to binding sites along the surfaces of the collagen fibrils, facilitating auto-transformation of the amorphous calcium phosphate nanoprecursors and the deposition of apatite crystallites along the interfibrillar spaces (FIG. 2C); and (4) intrafibrillar remineralization wherein, as more polyvinylphosphonic acid molecules diffuse into the collagen fibrils and bind to specific sites along the tropocollagen molecules, intrafibrillar remineralization occurs within the gap zones of the collagen fibrils (FIG. 2D). In one embodiment, the collagen-binding nucleation factor may be polyvinylphosphonic acid and the phosphate-binding apatite stabilizer may be polyacrylic acid.

Figure 2C:
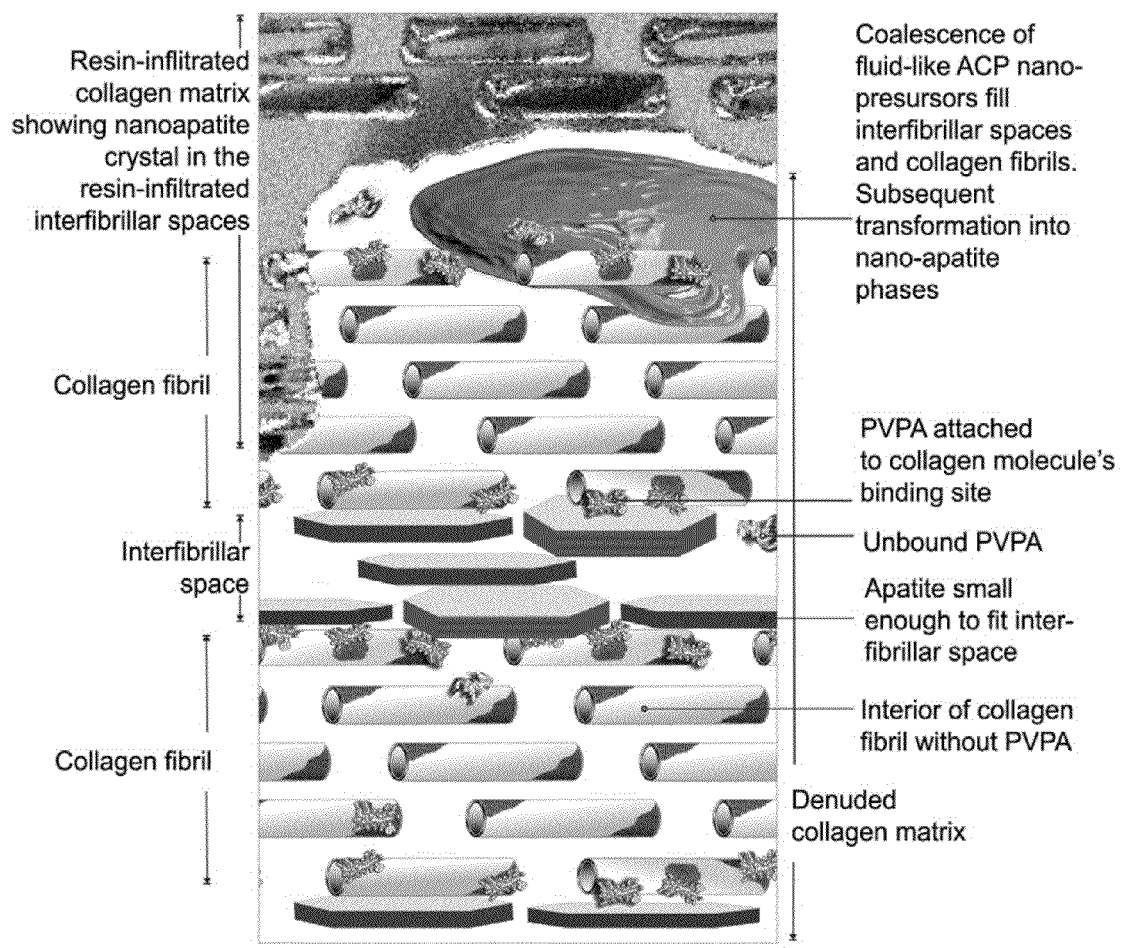
Figure 2D:
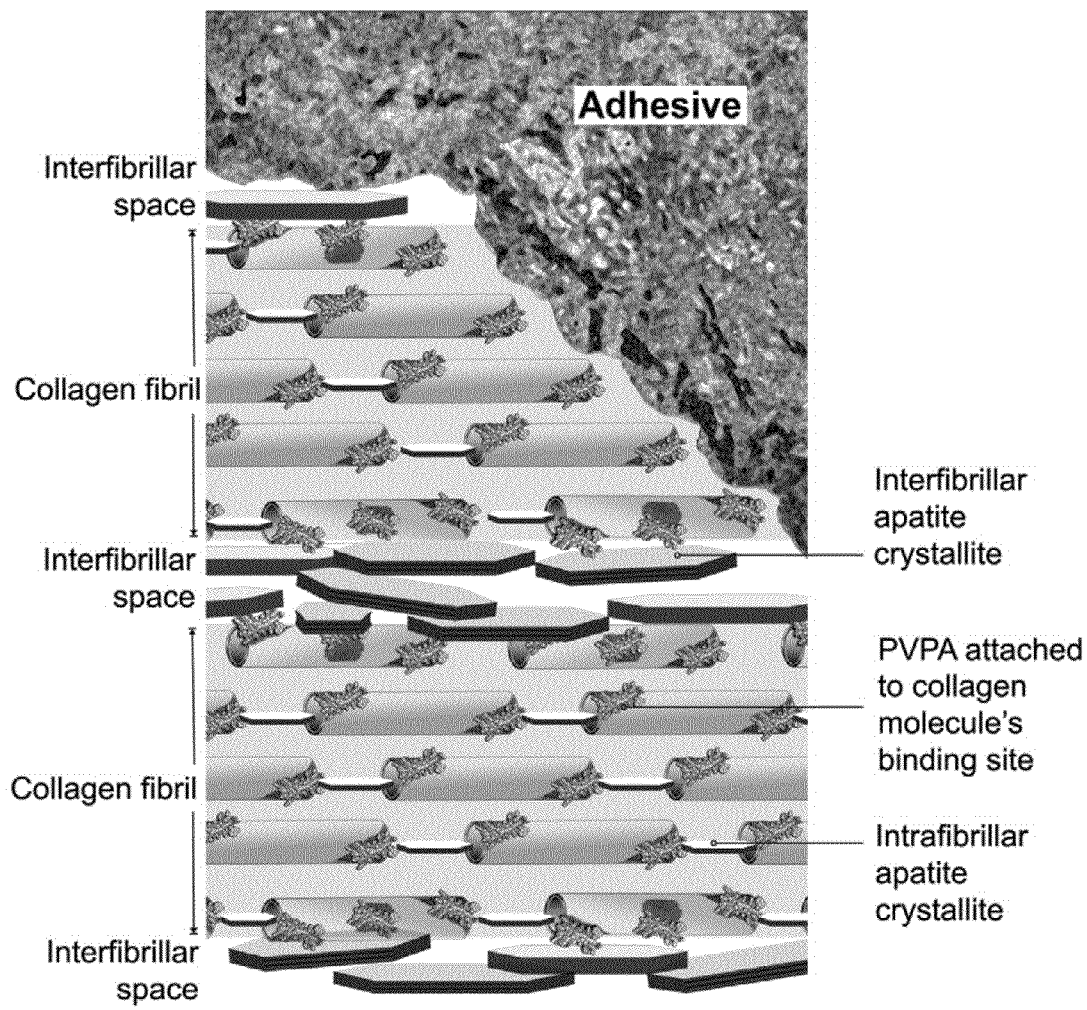

In one embodiment, PVPA or an analogous collagen-binding nucleation factor may diffuse into the denuded collagen matrix and bind initially to specific sites along the surfaces of the collagen fibrils. For example, FIG. 2C shows that, in certain embodiments, auto-transformation of the coalesced amorphous calcium phosphate nanoprecursors into apatite may result in their deposition within the interfibrillar spaces. FIG. 2D shows that, in certain embodiments, PVPA or an analogous collagen-binding nucleation factor may also diffuse into the collagen fibrils and attach to the specific locations along the tropocollagen molecules, thereby guiding mineral deposition within the gap regions of the collagen fibrils.

In certain embodiments of the invention, the apatite platelets may be the end-products of mesoscopic transformation of multiple, orderly arranged, and closely approximated polyacrylic-acid-stabilized mesocrystalline intermediates. In one embodiment, this modular assembly strategy through a particle-mediated approach may proceed via the formation of nanoscopic mineral bridges across the surfaces of the mesocrystals. In another embodiment, the method of the present invention may permit hierarchical crystalline order (i.e., intrafibrillar and interfibrillar minerals) to be re-established in incompletely resin-infiltrated type-I collagen fibrils under ambient temperature.

In another embodiment, transformation of an amorphous calcium phosphate precursor may involve kinetically-driven metastable intermediate stages involving the formation of prenucleation clusters, liquid-like polyanionic molecule-stabilized amorphous precursor phase, and penultimate mesocrystalline phases that eventually fuse to produce the ultimate crystal structure (Pouget, E. M. et al., *Science,* 2009, 323: 1455-1458; Olszta, M. J. et al., *Mat. Sci. Eng. R.,* 2007, 58:77-116; Cölfen, H. and Mann, S., *Angew. Chem. Int. Ed.,* 2003, 42:2350-2365). In some embodiments, effective remineralization of completely demineralized dentin collagen matrices may require a biomimetic system comprising dual biomimetic analogs, one for the purpose of sequestration of amorphous calcium phosphate nanoprecursors phase and the other for templating of the transformed crystalline apatite phase along specific sites within the collagen fibrils. For example, effective remineralization of completely demineralized dentin collagen matrices may comprise a first step of initiating mineralization in the hole zones of the collagen fibrils to begin intrafibrillar mineralization, and a second step of completing the mineralization by growing similar sized crystals in the 20 nm wide interfibrillar spaces. The remineralization process may result in stiffening and strengthening demineralized dentin.

In certain embodiments, the biomineralization may exhibit a high level of spatial and hierarchical control as mineralization may take place in a confined reaction environment under ambient temperature and pressure conditions. Also, in certain embodiments, metastable amorphous mineral precursors may be involved in natural mineralization processes. In certain embodiments, as type I collagen matrix in dental tissue does not have the capacity to induce matrix-specific mineral formation from metastable calcium phosphate solutions (Kawasaki, K. et al., *J. Exp. Zool. B. Mol. Dev. Evol.,* 2006, 306:295-316; Veis, A., *J. Bone Miner. Res.,* 1993, 8:S493-7), non-collagenous proteins (NCPs) are generally required as templates for regulating bone and dentin mineralization and for controlling the dimension, order and hierarchy of apatite deposition within mineralized hard dental tissues. (Gajjeraman, S. et al., *J. Biol. Chem.,* 2007, 282:1193-204; Qin, C. et al., *J. Dent. Res.,* 2007, 86:1134-41.) NCPs include proteins containing aspartic acid and glutamic acid-rich domains, as well as phosphoproteins, which may act as nucleators or inhibitors, growth modifiers, anchoring molecules, or as scaffolds for mineral deposition during tooth development (George, A. et al., *J. Biol. Chem.,* 1993, 268:12624-12630; He, G. et al., *J. Biol. Chem.,* 2005, 280:33109-33114). NCPs possess carboxylic acid and phosphate functional groups that act as preferential sites for apatite nucleation (Banks, E. et al., *Science,* 1977, 198:1164-6; Tanahashi, M. et al., *J. Biomed. Mater. Res.,* 1997, 34:305-15).

For example, dentin matrix protein-1 (DMP-1) is a member of the highly acidic NCPs (George, A. et al., *J. Biol. Chem.,* 1993, 268:12624-30) and as such, may be utilized as part of the remineralization process once the initial crystallization has occurred in certain embodiments of the present invention. The N-terminal domain of DMP-1 is rich in aspartic acid and is thought to participate in stabilizing the amorphous calcium phosphate phase and inhibits apatite formation (Gajjeraman, S. et al., *J. Biol. Chem.,* 2007, 282:1193-204). Also, the C-terminal of DMP-1 is a glutamic acid- and serine-rich domain which has been proposed as a site that facilitates apatite nucleation. In addition to its potent calcium binding capacity, DMP-1 has a high affinity to fibrillar collagen (He, G. et al., *J. Biol. Chem.*, 2004, 279:11649-56).

Also, phosphophoryn, another NCP phosphoprotein rich in aspartyl (Asp) and O-phosphoseryl (Ser(P)) residues (Huq, N. L. et al., *Arch. Oral Biol.*, 2005, 50:807-19), may also involved in matrix-mediated biomineralization of dentin once the initial crystallization has occurred in certain embodiments of the present invention.

Thus, in some embodiments, biomineralization of dentin type I collagen may comprise the use of non-collagenous proteins (NCPs) or NCP analogs that function to sequester the mineral phase into nanoscopic compartmental spaces (i.e., act as a calcium phosphate-binding apatite stabilizer) and then nucleate apatite crystallites via templating within the collagen fibrils (i.e., act as a collagen-binding nucleation factor). The mineral phase may comprise amorphous calcium phosphate. The nanoscopic compartmental spaces may have dimensions that approximate the dimensions of the hole zones and microfibrillar spaces within the collagen fibrils. In some embodiments, the calcium phosphate-binding apatite stabilizer may comprise repeating glutamic or aspartic acid sequences that contain multiple carboxylic acid groups that function as crystal growth modulators by attaching to specific crystalline planes and stabilizers of amorphous calcium phosphate precursors. In certain embodiments, the calcium phosphate-binding apatite stabilizer may comprise polyanionic molecules containing multiple carboxylic groups that may reduce the size of the stabilized amorphous calcium phosphate precursors. For example, the polyanionic molecules may comprise polyacrylic acid, poly(aspartic) acid, poly (acrylic acid-co-vinyl phosphonic acid), poly(aspartic acid-co-vinyl phosphonic acid), poly(methacrylic acid-co-vinyl phosphonic acid), poly(acrylic acid-co-vinyl aminomethylene phosphonic acid), poly[acrylic acid-co-bis(2-chloroethyl) vinylphosphonate], poly[acrylic acid-co-1-hydroxyethylidene-1,1-diphosphonic acid] or poly[aspartic acid-co-bis (2-chloroethyl) vinylphosphonate. In alternative embodiments, casein phosphopeptides may stabilize amorphous calcium phosphate for the purpose of remineralizing enamel. In certain embodiments, the collagen-binding nucleation factor may bind to the collagen fibrils at specific sites such as the collagen bands adjacent to the hole zones of the collagen fibril. For example, the collagen-binding nucleation factor may present anionic charged sites for attraction of the stabilized amorphous calcium phosphate complexes, facilitating the transformation of amorphous precursor phase calcium phosphate into crystalline apatite phases at both intrafibrillar and extrafibrillar locations. In preferred embodiments, the collagen-binding nucleation factor may comprise PVPA or sodium trimetaphosphate.

In certain embodiments, intrafibrillar remineralization may impose requirements on both the collagen fibrils and the dimension and order of apatite crystals within the fibril (Pashley, D. H. et al., *J. Dent. Res.*, 2004, 83:216-221; Landis, W., *Bone*, 1995, 16:533-544; Arsenault, A. et al., *Calcif. Tissue Int.*, 1988, 43:202-212). First, the collagen fibrils may need to be structurally intact and not degraded by endogenous matrix metalloproteinases released by the partially demineralized dentin. Also, the apatite phase may need to be small enough to fit within the intrafibrillar (~30-40 nm wide and ~100 nm long) and interfibrillar (~20 nm wide and very long) spaces of the collagen matrix. Thus, in at least certain embodiments, the apatite crystals may need to be less than 100 nm along their c-axes in order to be small enough to fit into the holes and overlap zones of the collagen fibril. Furthermore, the apatite crystals may need to be crystallographically oriented with their c-axes parallel to the axes of the microfibrils.

In certain embodiments, metastable amorphous mineral precursors may be involved in natural mineralization processes. With the advent of nanotechnology, acidic macromolecules may be used to reduce these amorphous phases to a nanoscale (Liou, S. C. et al., *J. Biomed. Mater. Res. B. Appl. Biomater.*, 2005, 73:117-122; Oaki, Y. et al., *Adv. Func. Mater.*, 2006, 16:1633-1639). Also, biomimetic polyelectrolyte and poly(amino) acid macromolecules that mimic the functional domains of natural NCPs can be employed in certain embodiments of the present invention (Stupp, S. I. et al., *Science*, 1997, 277:1242-1248; Girija, E. K. et al., *J. Mater. Sci.: Mater. Med.*, 2004, 15:593-599). Thus, in one embodiment of the invention, inorganic nanocrystals coated with organic molecules may undergo self-assembly and crystallographic alignment, possibly via the formation of mineral bridges, to produce larger mesocrystals that function as intermediates for the formation of single microscopic or macroscopic crystals.

In some embodiments, the present invention may comprise the use of a remineralizing restorative material capable of remineralizing demineralized dentin, wherein the restorative material comprises a resin-based composite, a phosphate source and a calcium hydroxide source. In some embodiments, the remineralizing restorative material may also comprise a collagen-binding nucleation factor and/or a calcium phosphate-binding apatite stabilizer.

FIGS. 3-7 illustrate additional embodiments of the present invention as used to remineralize demineralized acid-etched dentin. FIGS. 8-12 illustrate additional embodiments of the present invention as used to remineralize demineralized acid-etched dentin that has been bonded to restorative material.

In certain embodiments, and as illustrated in FIGS. 3-7, dentin may be prepared from human teeth. For example, human molars may be collected and a the dentin tissue harvested as disks. In a preferred embodiment, the dentin is present in a live tooth in a patient's mouth. For example, the dentin may be acid-etched with 37% (w/v) phosphoric acid for 15 sec and rinsed with deionized water to create a 5-8 μm thick layer of demineralized collagen matrix on the surface of the dentin tissue.

In an embodiment, the method may use a phosphate-containing buffer as the phosphate source. In one non-limiting embodiment, the phosphate is a calcium and magnesium-free buffer containing 136.8 mM NaCl, 4.2 mM $NaHCO_3$, 3.0 mM KCl, 1.0 mM $K_2HPO_4.3H_2O$, 1.5 mM $MgCl_2.6H_2O$, 2.5 mM $CaCl_2$, and 0.5 mM $Na_2SO_4$ in deionized water that is filtered before use. In one embodiment, the phosphate-containing buffer may further contain 0.1M Tris Base and 0.1 M HCl. In alternate embodiments, the pH of the phosphate-containing buffer may be physiological or nonphysiological. For example, in some embodiments, the pH of the phosphate-containing buffer may be 7.3 or 7.4. In another embodiment, the pH of the phosphate-containing buffer may be at least 9.5 after the release of hydroxyl ions from the calcium hydroxide source.

Also, as exemplified in FIGS. 3-12, a calcium donor may be added. In one embodiment, Portland cement that has been allowed to set (harden) may be added to the phosphate-containing buffer at a ratio of 15 mL buffer/g of cement. In another embodiment, demineralized dentin is incubated in the phosphate-containing buffer in which Portland cement or another suitable calcium hydroxide source is also present and incubated at 37° C. The incubation may take place for 2, 4, 6 and/or 8 weeks or a shorter suitable period of time.

Also, a collagen-binding nucleation factor, for example, polyvinylphosphonic acid, and a phosphate-binding apatite stabilizer may also be added to the phosphate-containing buffer to induce mineralization of the demineralized dentin.

For example, use of polyacrylic acid (PAA) in the phosphate-containing buffer as the phosphate-binding apatite stabilizer to induce apatite crystal formation is shown in FIG. 3. FIG. 3A shows that as Portland cement is incubated in the phosphate-containing buffer in the presence of various concentrations of PAA, the pH of the solution increases over time due to the release of the calcium and hydroxide ions from the cement. As these ions are incorporated into the apatite crystal formed, the pH of the solution stabilizes. Thus, as shown in FIG. 3A, higher concentrations of PAA can reduce the overall maximum pH obtained due to the molecule's acidic nature. For example, in one embodiment, FIG. 3A shows that the inclusion of 100 µg/mL PAA caused the pH of the buffer to stabilize at approximately 9.4. This is in contrast to buffer containing 500-5000 µg/mL PAA, in which the pH stabilized at or below pH 9, or in the absence of PAA, in which the pH stabilized at approximately 11.

Figure 3A:
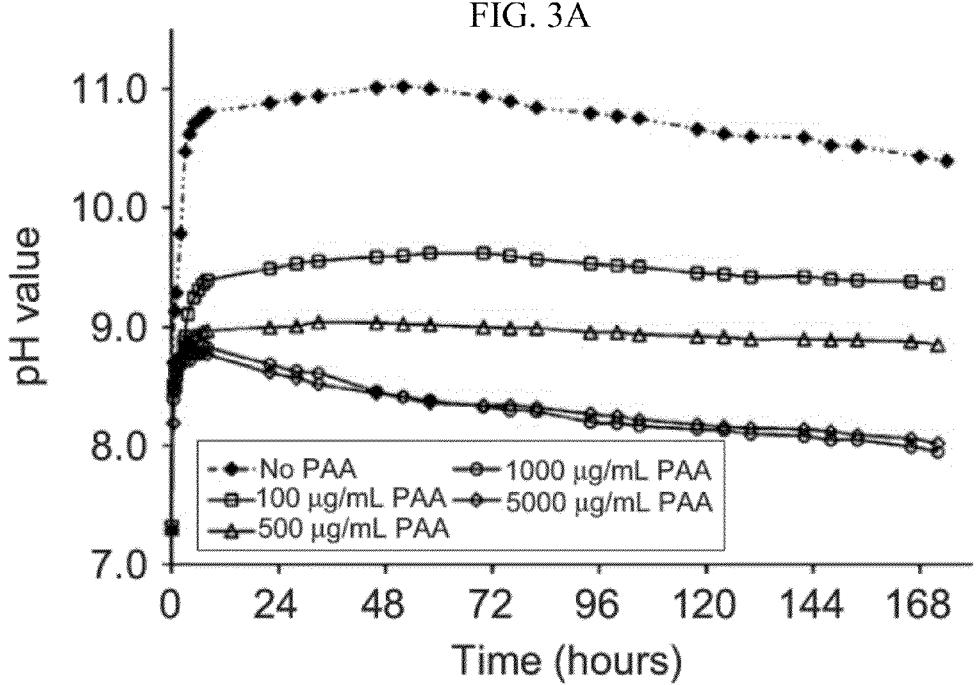
FIG. 3 shows in accordance with alternate embodiments of the present invention, the effects of the addition of different concentrations of polyacrylic acid (MW 1800) to a phosphate-containing fluid (PCF; pH adjusted to 7.3) on apatite precipitation by hardened white Portland cement in accordance with alternate embodiments of the present invention; where Panel A depicts pH profiles of the PCF solutions containing 0, 100, 500, 1000 and 5000 µg/mL of polyacrylic acid; Panel B depicts optical density profiles of the PCF solutions containing 0, 100, 500, 1000 and 5000 µg/mL of polyacrylic acid; and Panels C-F depict TEM images of calcium phosphate precipitates retrieved from the PCF solutions with different polyacrylic acid concentrations.
Figure 3B:
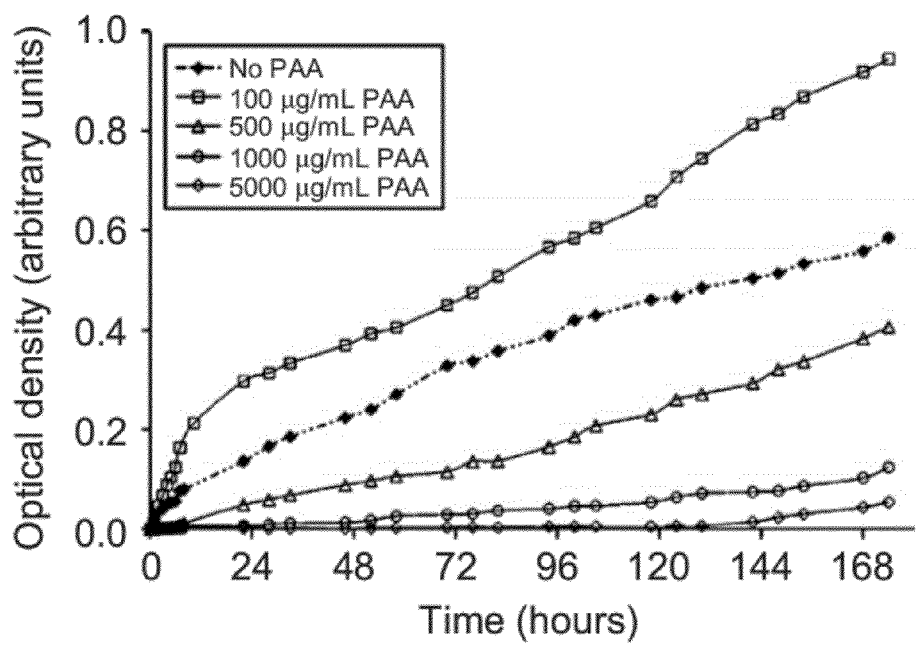
Figure 3C:
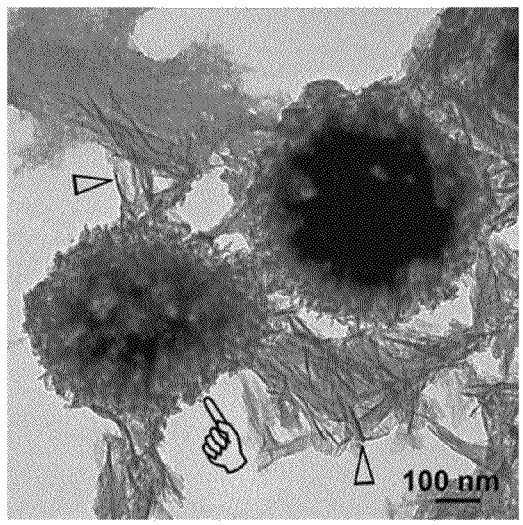
Figure 3D:
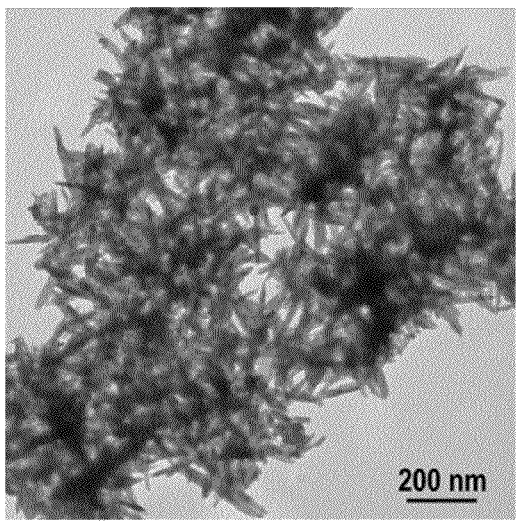
Figure 3E:
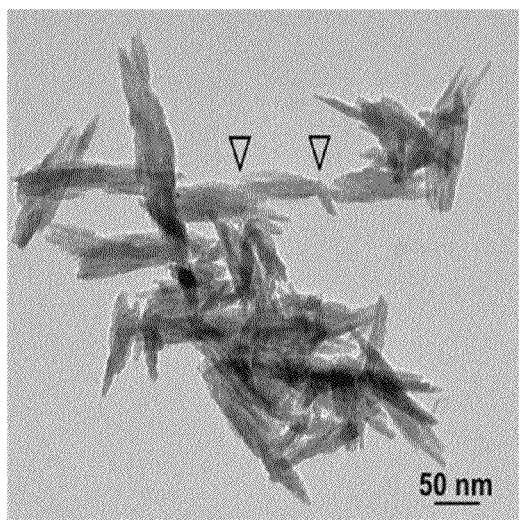

FIG. 3B shows that, in one embodiment, PAA may be used stimulate apatite crystal formation. In FIG. 3B, crystal formation is reflected as an increased turbidity of the phosphate-containing solution over time. PAA may be added to the buffer at a concentration that is within about 0 to 5000 µg/mL, or about 100 to 1000 µg/mL or about 100 to 200 µg/mL. For example, in one embodiment, addition of 100 µg/mL PAA may result in an approximately two-fold increase in apatite crystal formation compared to the amount formed in the absence of PAA, indicating that at this concentration PAA may act as a promoter of apatite nucleation/crystal growth. Further, as shown in FIG. 3E, 100 µg/mL PAA may result in the formation of apatite crystals that are 75-100 nm along the c-axis, which is of a desirable small size for mineralization of dentin.

Figure 3F:
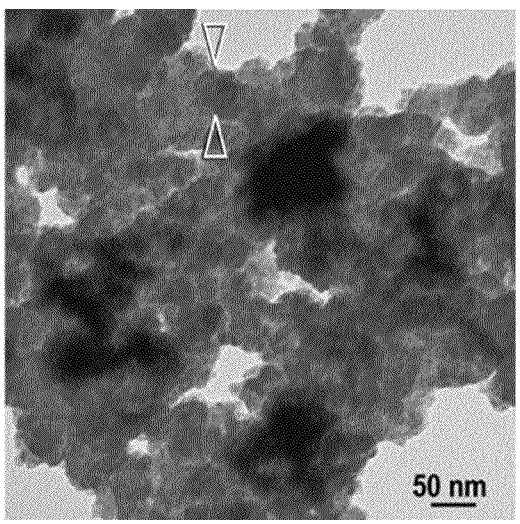

This is in contrast to conditions of no PAA (FIG. 3C) and very high PAA concentrations (FIG. 3F). FIG. 3B shows that, if the PAA concentration is too high (e.g., 500, 1000, 5000 µg/mL), PAA may inhibit apatite nucleation/crystal growth (e.g., decreased turbidity compared to no PAA sample indicates less apatite crystal formation). FIG. 3C shows that after a short incubation (2 hrs), prior to maximum pH levels, formation of amorphous calcium phosphate spheres that are only partially transformed into apatites may occur. FIG. 3D shows that, after allowing the incubation to proceed for 180 hrs (maximum pH achieved), complete transformation of amorphous calcium phosphate spheres into apatites may occur but these apatites are 200-250 nm along their c-axis, which is larger than is desirable for biomimetic mineralization of dentin.

In addition, FIG. 3F shows that, at high concentration of PAA (500-5000 µg/mL), formation of amorphous calcium phosphate nonspheres with a diameter smaller than 50 nm is achieved and no apatites are formed.

Consistent with the embodiments illustrated by FIG. 3, FIG. 4 shows that, in another embodiment, in the absence of either PVPA, or PVPA and PAA, remineralization was not achieved. For example, FIGS. 4A-D show that in the absence of PAA and PVPA, only surface deposition of amorphous calcium phosphate-derived apatite clusters was apparent, the clusters exhibiting a SAED (selected area electron diffraction) pattern indicative of the absence of minerals. In addition, FIG. 4B also shows lack of remineralization in the presence of PAA but the absence of PVPA, though PAA-stabilized amorphous calcium phosphate nanospheres were occasionally seen within the demineralized collagen matrix (FIGS. 4F and 4G) that has been partially transformed into apatite nanocrysals (5-10 nm long) (FIG. 4H).

In one embodiment, polyvinylphosphonic acid (PVPA) is included with PAA in the phosphate-containing buffer to act as the collagen-binding nucleation factor, wherein the PVPA causes intrafibrillar deposition of apatites in demineralized dentin in addition to interfibrillar deposition as shown in FIG. 5. As shown in FIG. 5A, in one embodiment, initial intrafibrillar and interfibrillar remineralization of demineralized dentin may begin as early as after 2 weeks of incubation in the presence of 500 µg/mL PAA and 200 µg/mL PVPA. FIG. 5B shows that remineralization may begin at the base of the intact mineralized dentin, with deposition of amorphous calcium phosphate nanospheres along the surface of the collagen fibrils as shown in FIG. 5B. FIGS. 5D-5F also show that intrafibrillar remineralization may occur in an embodiment. FIG. 5C and FIG. 5E show by high magnification FESEM that the collagen fibrils have discontinuous regions of periodicity that resisted dehydration shrinkage and that the collagen fibrils in the more highly remineralized regions of dentin exhibited a "corn-on-the-cob" appearance, respectively, both of which are characteristic of intrafibrillar mineralization. Further, FIG. 5D and FIG. 5F (as well as FIG. 5G), respectively, confirmed the presence of intrafibrillar mineralization with apatite crystals in these remineralized regions.

FIG. 6 shows that, in another embodiment, continuous intrafibrillar and interfibrillar remineralization may be achieved after 4 weeks of incubation in the presence of 500 µg/mL PAA and 200 µg/mL PVPA. FIG. 6A and FIG. 6C show that the remineralized dentin may have many of the same physiological characteristic as mineralized dentin. In some embodiments, however, and as shown in FIGS. 6A and 6C, the remineralized dentin may be less mineral dense and lack peritubular dentin around the dentinal tubule orifices. FIG. 6B shows that the majority of collagen fibrils may exhibit the "corn-on-the-cob" appearance consistent with interfibrillar mineralization. Also, FIG. 6D shows that collagen fibrils may be filled with apatite nanocrystals that are oriented along the longitudinal axis of the microfibril, enabling discernment of a rope-like subfibrillar architecture, where the fibril corrugation pattern with regular intervals (ca. 70 nm) may correspond with the fibril banding characteristics shown in FIG. 6C. FIG. 6E shows that transition of apatite nanocrystals to larger crystals with plate-like morphology was more evident in more electron-dense regions of partially remineralized dentin.

FIG. 7 shows that, in another embodiment, complete remineralization of acid-etched demineralized dentin may be achieved as early as after 6 weeks of incubation, and consistently after 8 weeks incubation, in the presence of 500 µg/mL PAA and 200 µg/mL PVPA. FIG. 7A and FIG. 7B show, for example, that complete remineralization may be observed after 8 weeks incubation. FIG. 7C shows that the superficial 8-10 µm of the dentinal tubule orifice may be devoid of peritubular dentin. In comparison to intact mineralized dentin, as shown in FIG. 7E and FIG. 7F, the embodiment exemplified in FIG. 7D shows that remineralized dentin may have both intrafibrillar and interfibrillar apatite crystal in the collagen fibrils. Both FIGS. 7D and 7F show that crystals in the demineralized dentin may be less organized as compared to intact mineralized dentin.

In one embodiment, the demineralized dental tissue may comprise acid-etched demineralized dentin that has been bonded to restorative material. Methods of applying restorative materials to teeth are well known in the art. For example, the restorative materials may be etch-and-rinse resins, for example, One-Step or Single Bond Plus dental resins. The dental tissue may be acid-etched by applying a 32% phosphoric acid gel for 15 sec to the dentin prior to application of a restorative material.

Figure 8A:
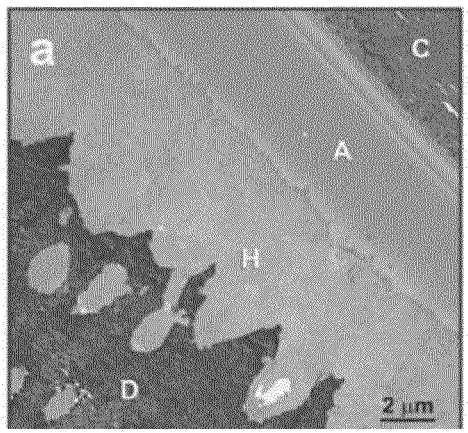
FIG. 8 shows in accordance with alternate embodiments of the present invention, transmission electron micrographs depicting the ultrastructure and silver nanoleakage of control specimens stored in simulated body fluid (containing Portland cement blocks but without biomimetic analogs) for 4 mos in accordance with one embodiment of the present invention; Abbreviations: C, composite; A, unfilled adhesive; FA, filled adhesive; H, hybrid layer; D, mineralized dentin; P, polyalkenoic acid copolymer component of the filled adhesive.
Figure 8B:
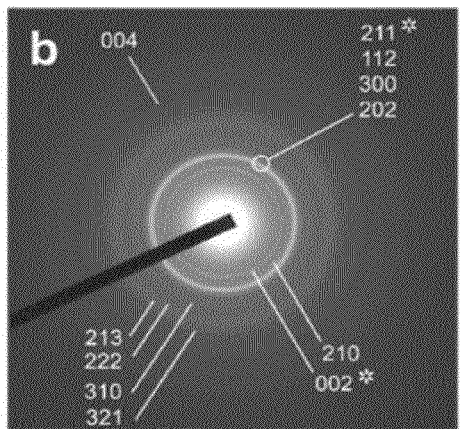
Figure 8C:
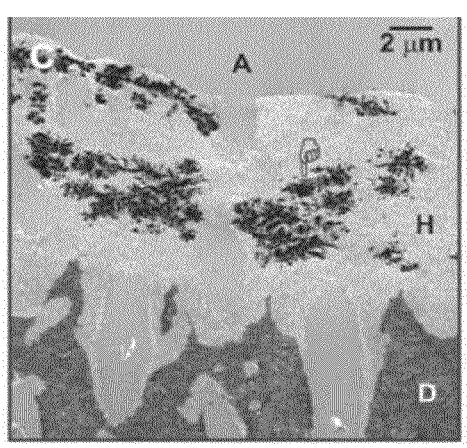
Figure 8D:
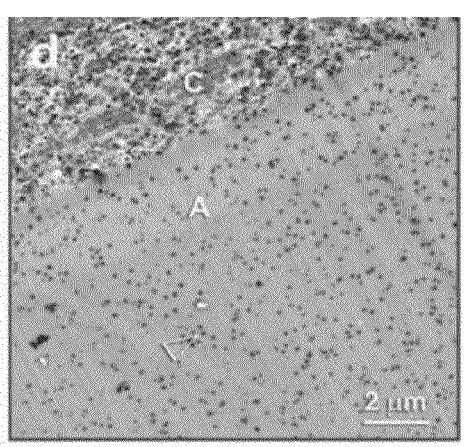
Figure 8E:
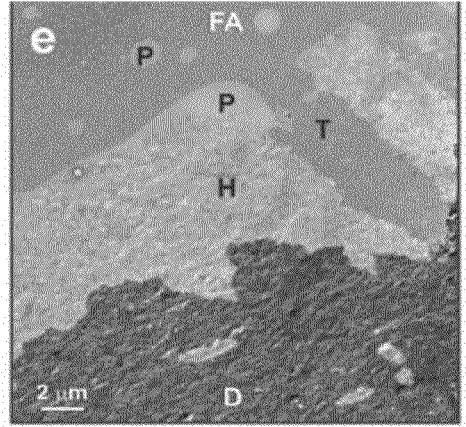
Figure 8F:
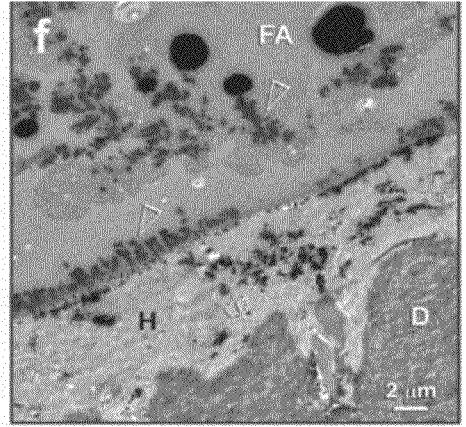

FIG. 8A, FIG. 8B and FIG. 8E illustrate that acid-etching may produce a 5-8 μm thick completely demineralized dentin layer located between the hybrid layer, where the restorative material has infiltrated the demineralized dental tissue, and the underlying mineralized dentin base. FIG. 8C, FIG. 8D and FIG. 8F show that where there has been incomplete infiltration of the restorative material into the hybrid layer, water-rich zones may exist beneath the restorative material in the interfibrillar spaces of the hybrid layer, and that fluidic movement may occur through these spaces beneath the restorative material. In some cases, the presence of the demineralized hybrid layer may result in further demineralization of surrounding mineralized dental tissue.

In one embodiment, acid-etched demineralized dentin bonded to restorative materials may be remineralized by incubation with a calcium hydroxide source, a phosphate source, a collagen-binding nucleation factor and a calcium phosphate-binding apatite stabilizer. For example, the acid-etched demineralized dentin bonded to restorative materials may be incubated with Portland cement in a phosphate-containing buffer containing 500 μg/mL PAA and 200 μg/mL PVPA. Remineralization of acid-etched demineralized dentin bonded to restorative materials may result in eliminating water-rich areas in the hybrid and adhesive layers thereby reducing demineralization of surrounding dental tissue.

FIG. 9 shows that, in one embodiment, interfibrillar remineralization of the hybrid layer in acid-etched demineralized dentin bonded to restorative materials may occur after 1 month of incubation. For example, as shown in FIGS. 9A-9C, in one embodiment, that electron-dense amorphous structures representing amorphous calcium phosphate nanoprecursors may penetrate the regions of the hybrid layer that are poorly infiltrated by restorative materials. FIG. 9D shows that nanocrystals may be observed after 1 month in the interfibrillar spaces of the hybrid layer. FIG. 9E shows that these nanocrystals are finer that the apatite platelets present in the underlying mineralized dentin base but that, as shown by FIG. 9F, they may transform into larger needle-shaped crystallites (ca. 20 nm long) within the interfibrillar spaces of the hybrid layer.

FIG. 10 shows that, in one embodiment, both interfibrillar and intrafibrillar remineralization of the hybrid layer in acid-etched demineralized dentin bonded to restorative materials may occur after 2-3 months of incubation. FIGS. 10A-10C show that an order alignment of nanocrystals may be deposited in the intrafibrillar spaces of the collagen fibril that co-exist with adjacent interfibrillar spaces. FIG. 10D shows that, after 3 months incubation, larger crystallite platelets (ca. 20 nm long) may be stacked in a repeating and orderly sequence within the collagen fibrils (ca. 100 nm diameter) of the hybrid layer acid-etched demineralized dentin bonded to restorative materials. FIG. 10E shows, in one embodiment, that these electron-dense platelets may be well-aligned with the longitudinal axis of the collagen fibrils, and FIG. 10F shows that, in one embodiment, heavy remineralization of the hybrid layer immediately adjacent to the adhesive layer may occur.

As discussed in more detail in the examples, in some embodiments, complete remineralization of the hybrid layer in acid-etched demineralized dentin bonded to restorative materials may occur after 3-4 months (FIG. 11). Regions of the hybrid layer less infiltrated by restorative material may be more heavily remineralized that regions of the hybrid layer in which the restorative material penetrated more fully. Both interfibrillar and intrafibrillar remineralization may occur in the hybrid layer of acid-etched demineralized dentin bonded to restorative materials, such as, for example, One-Step and Single-Bond Plus resins.

Also, and as illustrated by FIG. 12, in some embodiments, remineralization of the adhesive layer adjacent to the hybrid layer may occur after 3-4 months of incubation. For example, in one embodiment, remineralization of One-Step resin-bonded acid-etched demineralized dentin may occur in the water-filled channels close to the hybrid layer surface, as shown by FIGS. 12A and 12B, and in the water-rich zones directly beneath the restorative material, as shown by FIGS. 12C and 12D. Further more, as shown by FIGS. 12E and 12F, in some embodiments, water trees originating from the surface of the hybrid layer may be remineralized in Single-Bond Plus resin-bonded acid-etched demineralized dentin.

Figure 13A:
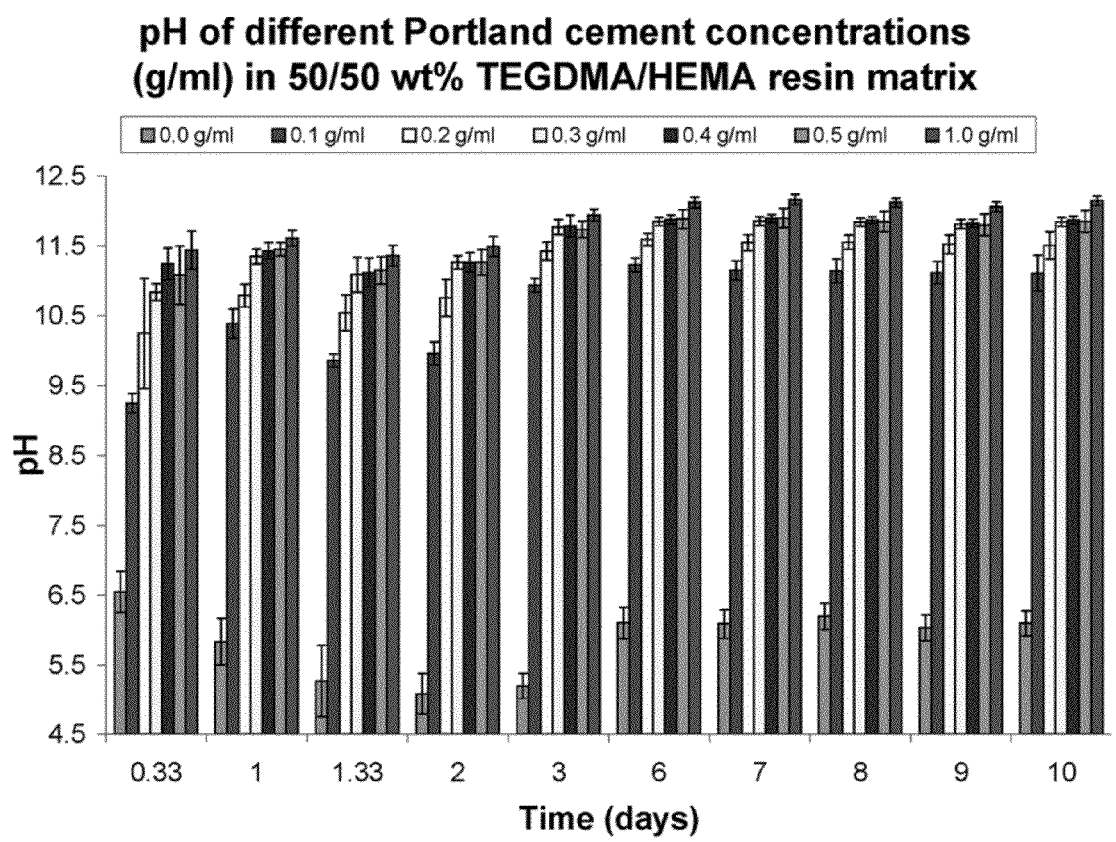
FIG. 13 shows in accordance with alternate embodiments of the present invention, remineralization of demineralized dentin using a therapeutic primer comprising 500 µg/mL PAA and 200 µg/mL PVPA in conjunction with a remineralizing restorative material comprising a resin composition containing various amounts of Portland cement powder as filler, specifically illustrating the effect on pH (Panel A), calcium ion production (Panel B) and modulus of elasticity (Panel C) of the resin-bonded dentin as a function of Portland cement added.
Figure 13B:
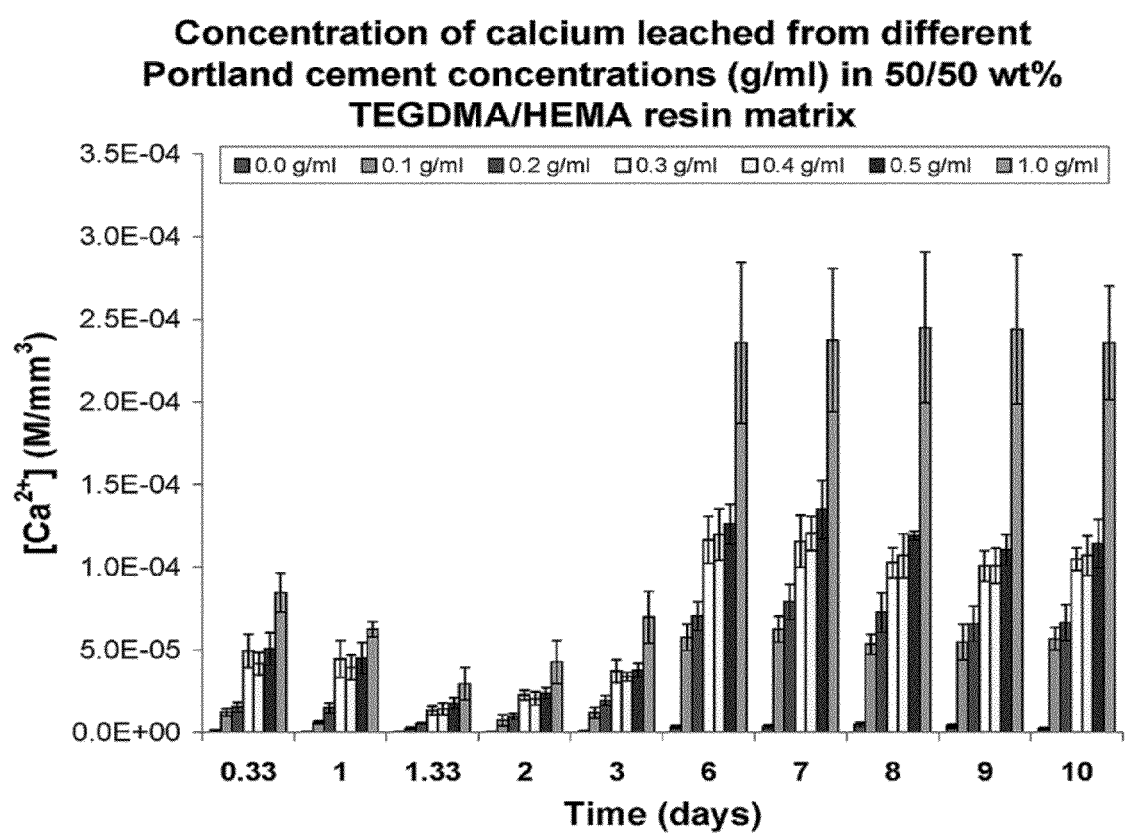
Figure 13C:
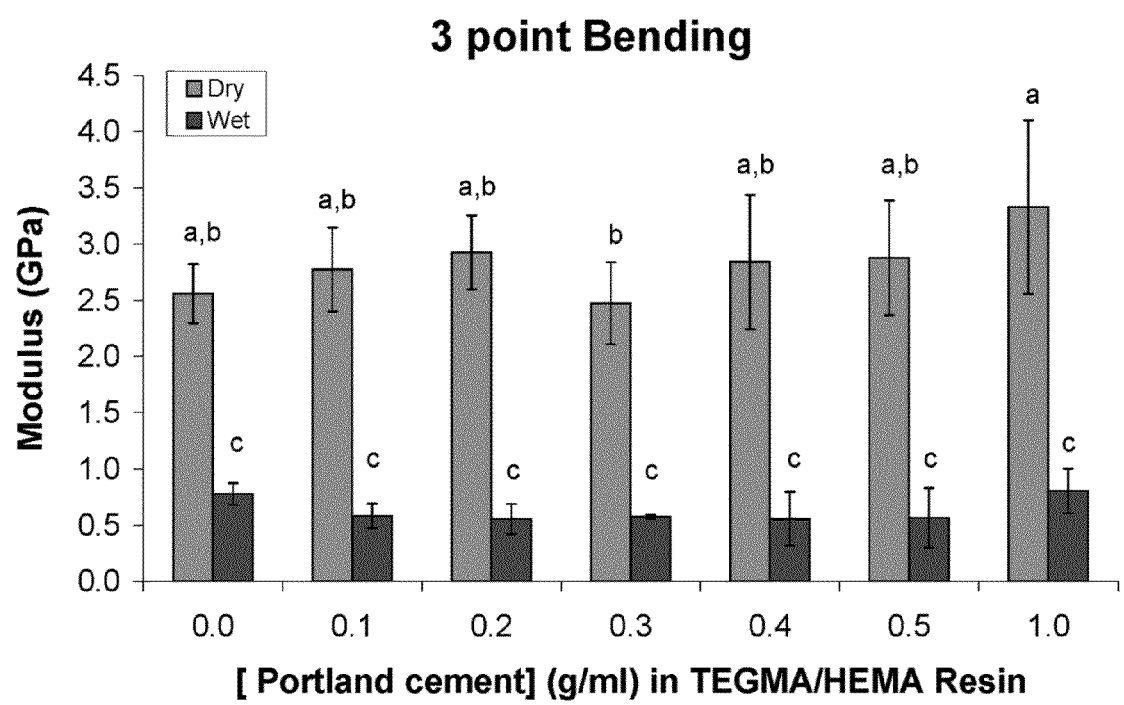

FIG. 13 shows that, in an embodiment of the present invention, a resin-based remineralizing restorative material containing a Portland cement filler, used in conjunction with a therapeutic primer comprising 500 μg/mL polyacrylic acid (PAA), 200 μg/mL of polyvinylphosphonic acid (PVPA) and 750 μg/mL of glycine or 1610 μg/mL of glutamic acid, resulted in the release of calcium ions and hydroxide ions over a period of several days. In alternate embodiments of the present invention, the Portland cement filler may be added to the remineralizing restorative material in the amount of 0.1, 0.2, 0.3, 0.4, 0.5 or 1.0 gram of set Portland cement powder/mL of resin. For example, FIG. 13A shows that, in one embodiment, the release of the hydroxyl ions resulted in an increase in the pH of the surrounding solution to about pH 10 within several hours. FIG. 13B shows, that in one embodiment, the remineralizing restorative material was also released calcium ions over the same period of time, with significant increases in calcium ion production occurring at least after 6 days. FIG. 13C shows, in another embodiment, the addition of increasing amounts of Portland cement as a filler to remineralizing restorative material did not decrease the initial modulus of elasticity of the remineralizing restorative materials.

Figure 14A:
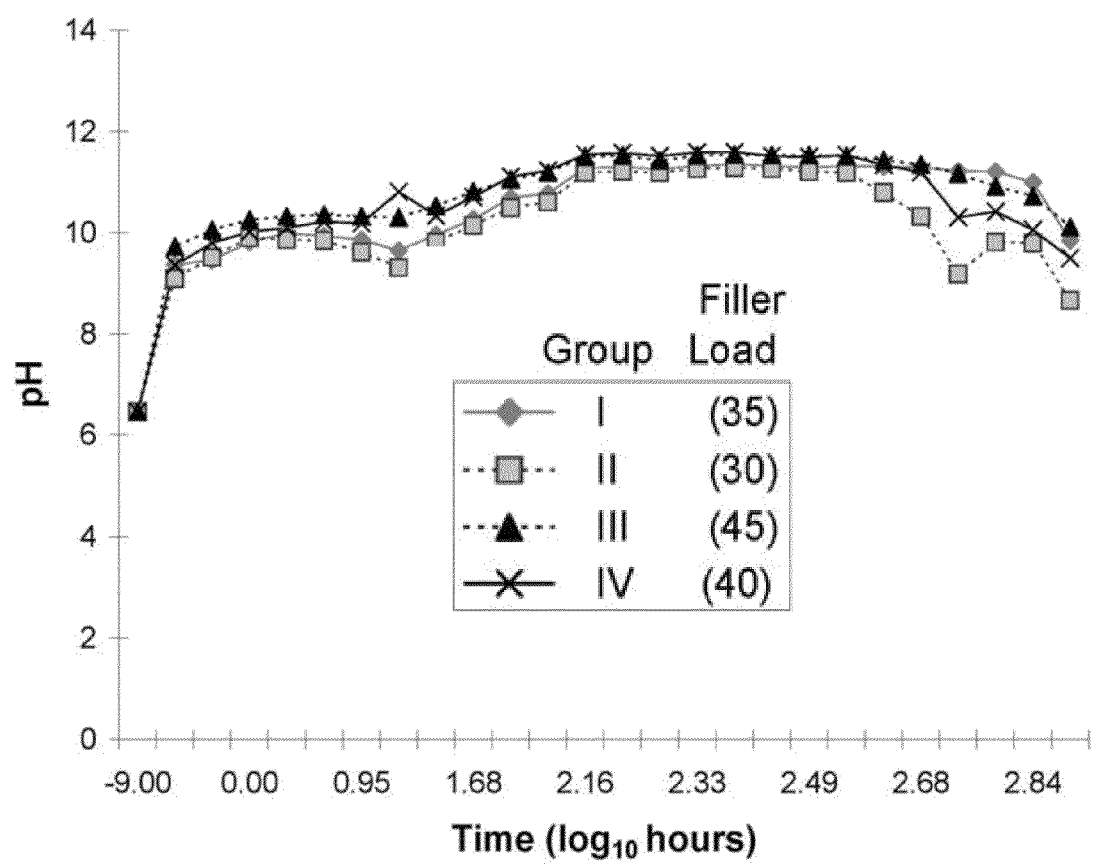
FIG. 14 shows that in accordance with alternate embodiments of the present invention, the pH (Panel A) and calcium ion production (Panel B) over time from resin-bonded dentin treated with a therapeutic primer and remineralizing restorative material as described in Example 3.
Figure 14B:
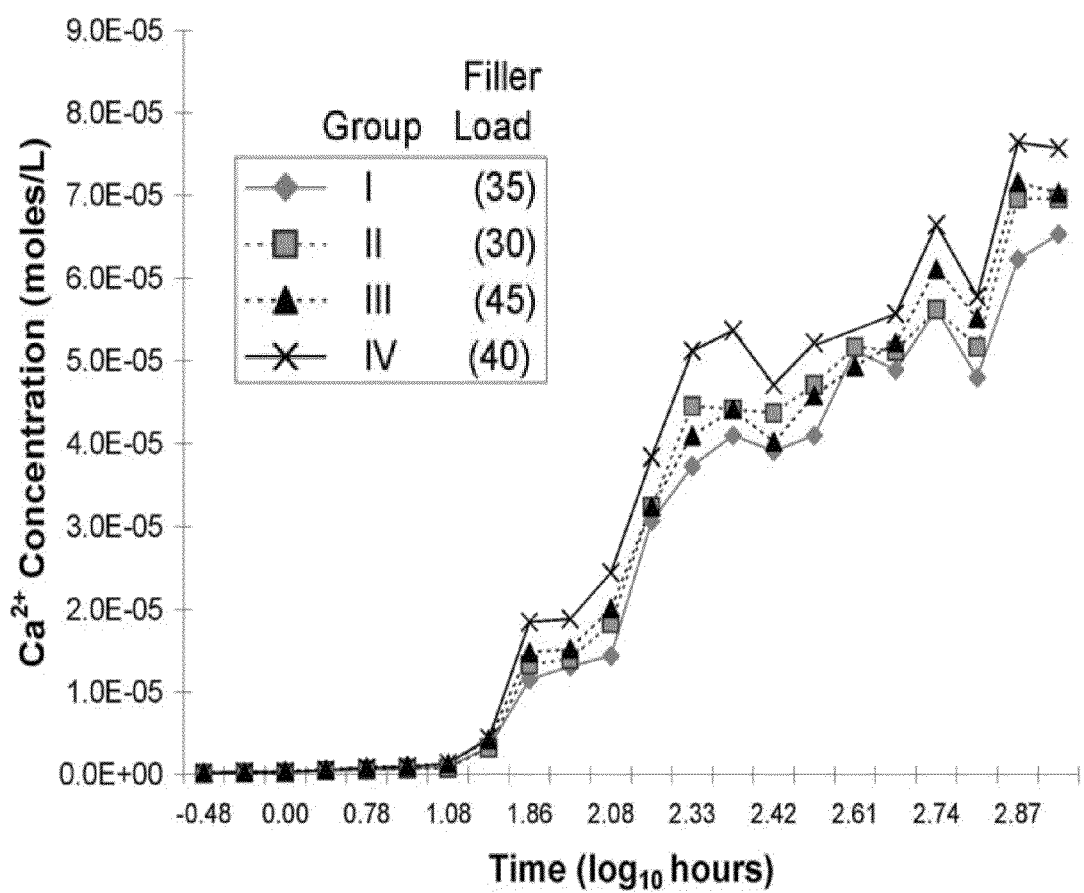

FIG. 14A shows that, in alternate embodiments, the rate of release of hydroxyl ions ($OH^-$) from four different formulations of remineralizing restorative material containing 35-45% Portland cement powder filler may cause an increase in pH from 6.5 to 10 within 1 hr and maintain that pH over a period of at least 30 days. FIG. 14B shows that, in one embodiment, calcium ions may also be released from the remineralizing restorative material over the same period of time. For example, in one embodiment, release of calcium ions may begin after 12 hours and increase continuously at least for 30 days.

FIG. 15 shows that, in some embodiments, the present invention may be used to remineralize dentin from primary teeth (i.e., from children).

Figures 16A, 16B:
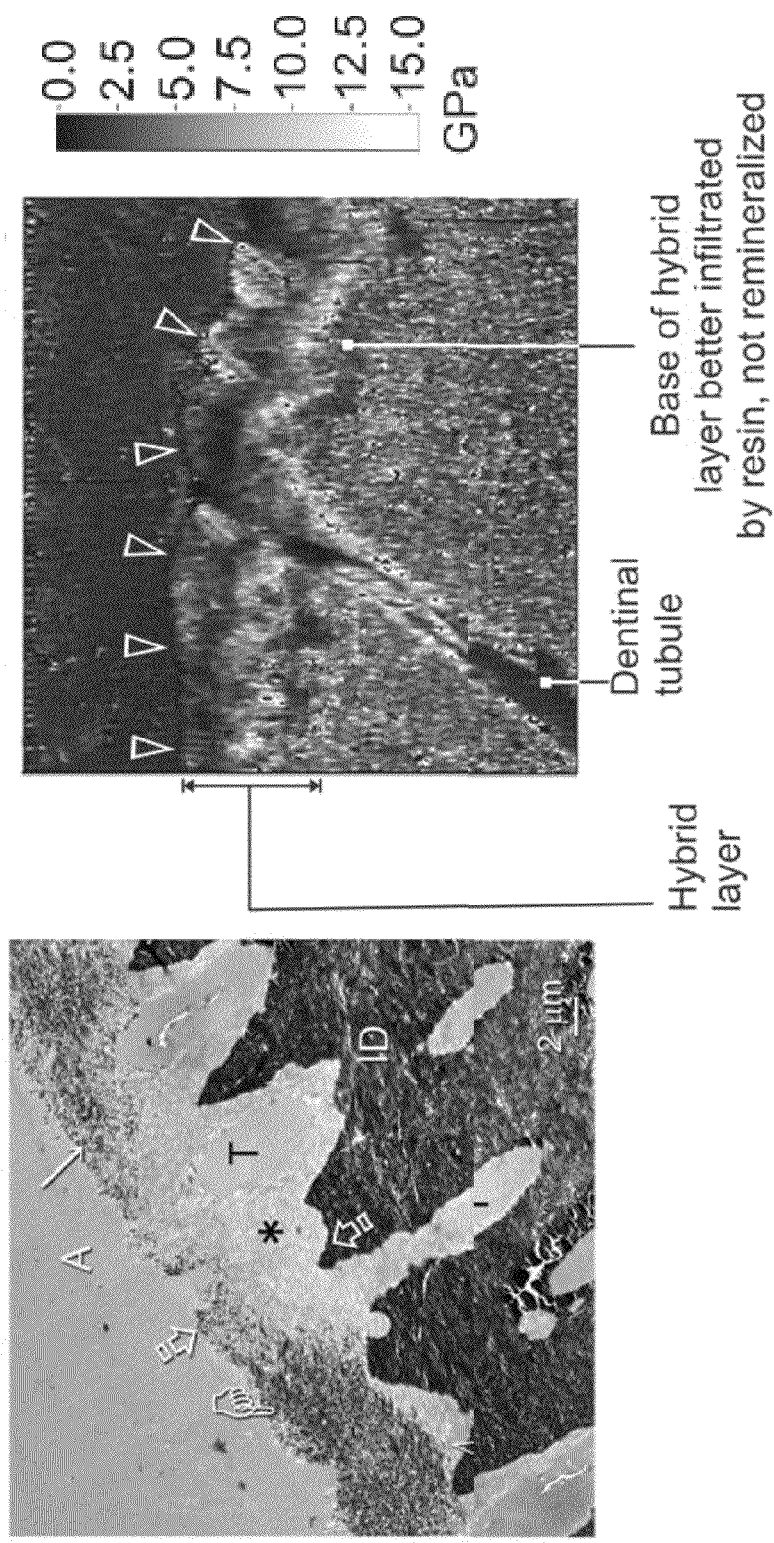
FIG. 16 shows in accordance with alternate embodiments of the present invention, the mechanical properties of remineralized resin-bonded dentin as illustrated by TEM analysis (Panel A) and dynamic mechanical testing (DMA) assaying two-dimensional mapping data of the complex modulus (Panel B), storage modulus (Panel C) and loss modulus (Panel D).
Figure 16D:
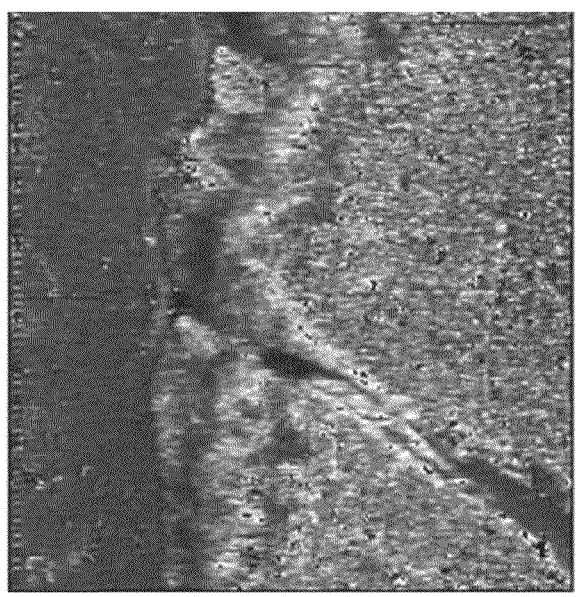
Figure 16C:
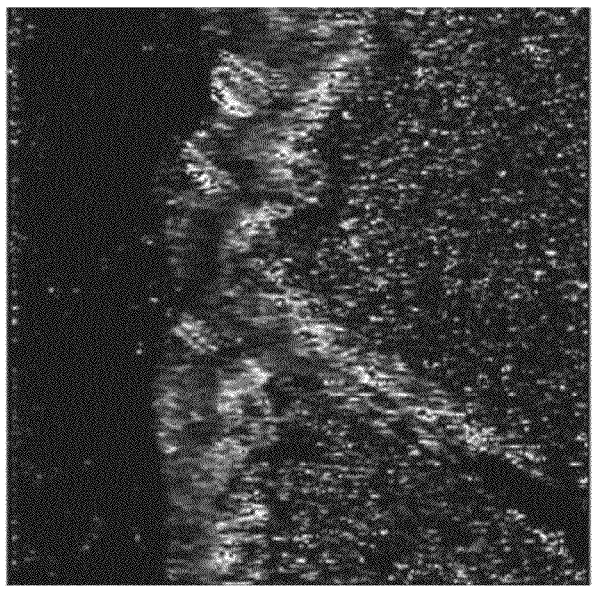
Figure 17A:
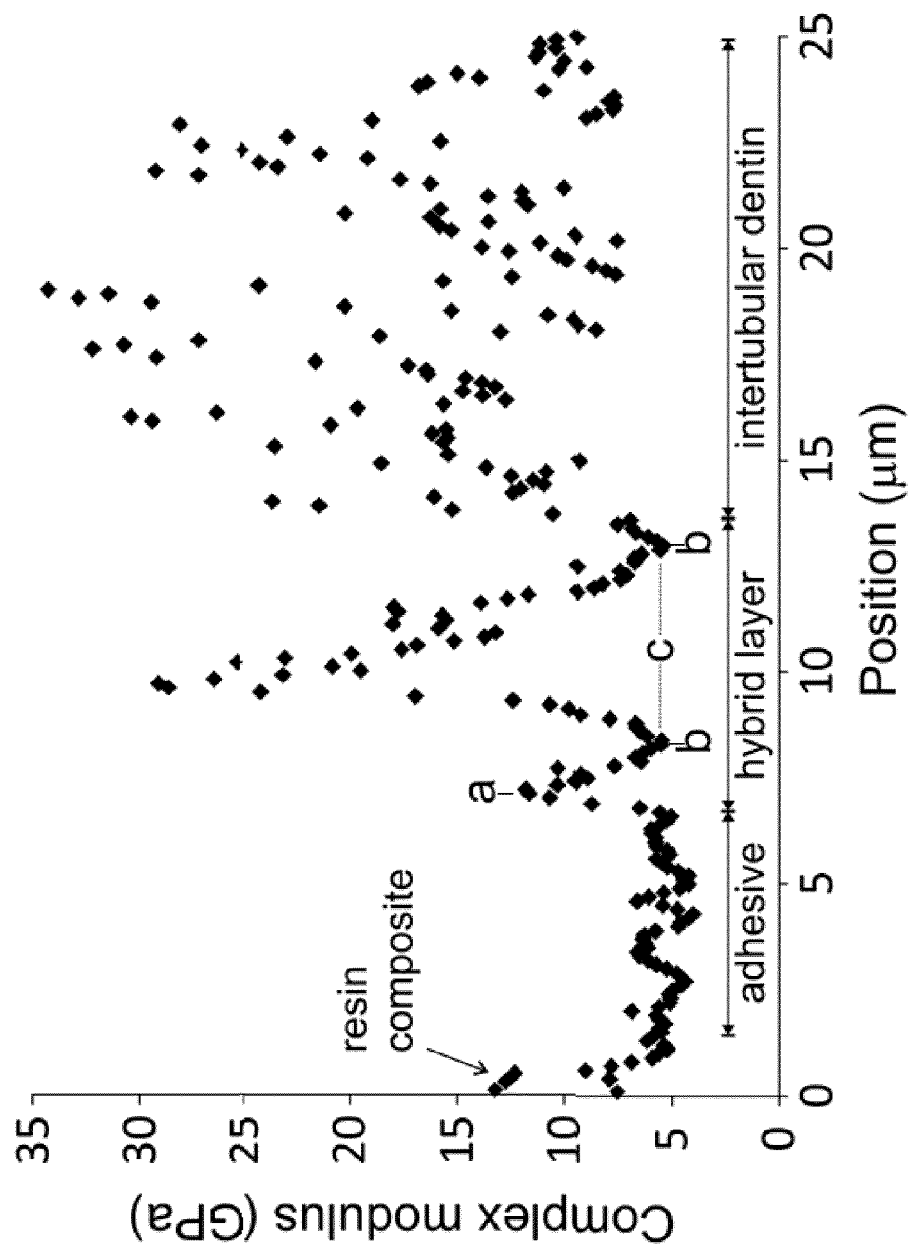
FIG. 17 shows in accordance with one embodiment of the present invention, the variation in complex modulus of a specimen as prepared in Example 7 from a single vertical line trough the resin composite, adhesive, hybrid layer and mineralized intertubular dentin.
Figure 17B:
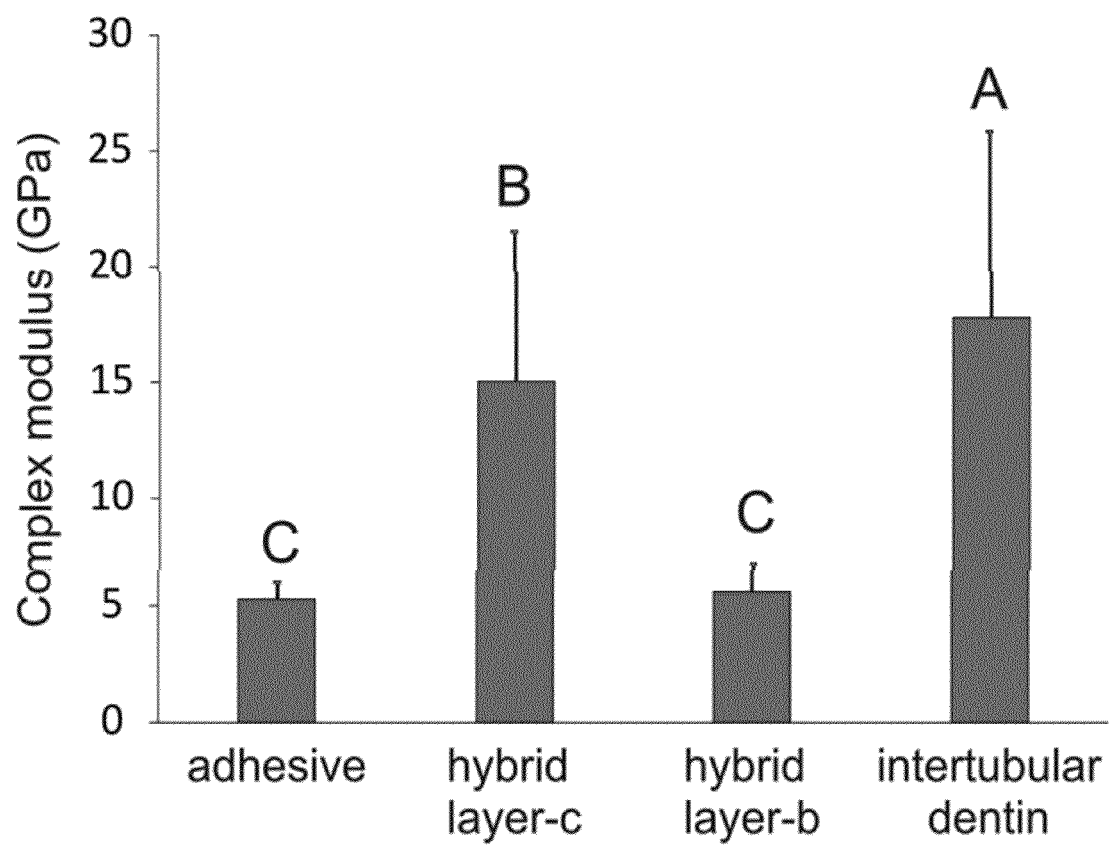

FIGS. 16 and 17 show that, in accordance with certain embodiments of the present invention, incompletely resin-infiltrated parts of the hybrid layer of dentin bonded to remineralizing restorative material exhibits a higher degree of stiffness as a result of remineralization as compared to demineralized dentin. In alternate embodiments, the stiffness of remineralized dentin may be determined by two-dimensional mapping data of the complex modulus, storage modulus and loss modulus using dynamic mechanical testing (DMA). For example, in some embodiments, the complex modulus in the more heavily remineralized regions of the hybrid layer may be 15,022±6,503 MPa, the complex modulus of the intertubular dentin may be 17,768±8,084 MPa) ($p<0.05$), and the complex modulus of the non-remineralized regions of the hybrid layer may be 5,286±727 MPa.

FIG. 18 shows that, in some embodiments of the present invention, the method of remineralizing demineralized dentin may comprise the use of a chemical phosphorylating agent such as sodium trimetaphosphate as the collagen-binding nucleation factor. In some embodiments, the sodium trimetaphosphate may be applied to demineralized dentin as a therapeutic primer prior to application of the resin-based remineralizing restorative material comprising Portland cement filler as the calcium hydroxide source. In some embodiments, the therapeutic primer may also comprise a calcium phosphate-binding apatite stabilizer such as 500 μg/mL polyacrylic acid (MW=1800 Da). In a preferred embodiment, the therapeutic primer may comprise 500 μg/mL polyacrylic acid and 2.5 sodium trimetaphosphate.

The remineralizing restorative material may be placed on top of demineralized dentin when creating a filling to repair carious dentin. The resin-based composite may comprise an inorganic mineral phase deposited within a polyacrylate-based matrix, wherein the resin-based composite serves as a slow-release device for calcium, phosphate and hydroxyl ions. In some embodiments, where the remineralizing restorative material also comprises a collagen-binding nucleation factor and a calcium phosphate-binding apatite stabilizer, these components may also be slowly released over time into the dental tissue. The resin-based composite may comprise hydrophilic methacrylates that are designed to induce water sorption.

In some embodiments, the calcium hydroxide source may comprise set Portland cement powder. In certain embodiments, the polyacrylate-based matrix swells and increases the permeability of polymers in the resin that envelop set Portland cement powder, thereby permitting the release of calcium, phosphate and, if present, collagen-binding nucleation factors and calcium phosphate-binding apatite stabilizers, for many months. For example, in some embodiments, calcium, phosphate, collagen-binding nucleation factors and calcium phosphate-binding apatite stabilizers may slowly diffuse from the overlying restorative composite into water-filled porosities within the underlying demineralized, resin-bonded dentin to induce remineralization. In certain embodiments, the calcium phosphate, collagen-binding nucleation factors and calcium phosphate-binding apatite stabilizers will diffuse out of the remineralizing restorative material into water-filled voids between the restorative material and the dentin thereby creating a supersaturated solution of these components.

In some embodiments, the inorganic mineral phase of the remineralizing restorative material may comprise calcium oxide, calcium hydroxide, calcium silicate mixtures in fine powdered form suspended in a resin matrix made up of 68 wt % bisphenol A glycidyl methacrylate (BisGMA), and 30 wt % 2-hydroxymethacrylate, and 0.25% camphorquine and 1% ethyl N,N-dimethyl-4-aminobenzoate. In an embodiments, the inclusion of 0.25% camphorquine and 1% ethyl N,N-dimethyl-4-aminobenzoate makes the matrix light-curable, for example, but not limited to, by the use of blue light. In another embodiment, the remineralizing restorative material may comprise an inorganic mineral phase of one of several calcium phosphates and an organic matrix comprising equal amounts of BisGMA and HEMA, in addition to 0.5 mol % camphoquinone, 0.5 mol % 2,2'-[dihydroxyethyl-p-toluidine (DHEPT), 0.5 mol % N-phenylglycine (NPG), 0.5 mol % dimethylaminoethyl]methacrylate (DMAEMA) and 1 wt % diphenyliodinium chloride (DPIC) to make the matrix light-curable in the presence of water (Ye et al., 2008).

In other embodiments, the collagen-binding nucleation factor may be applied directly to the dental tissue as a therapeutic primer rather than be included in the remineralizing restorative material. For example, the therapeutic primer may be retained within the collagen matrix and isolated from the oral cavity environment by the application of the remineralizing restorative material over the therapeutic primer. In certain embodiments, the therapeutic primer may also contain a calcium phosphate-binding apatite stabilizer. In other embodiments, calcium, phosphate and hydroxyle ions may diffuse from the remineralizing restorative material into the resin-infiltrated dentin collagen matrices resulting in the formation of amorphous calcium phosphate nanoprecursors that enter the demineralized collagen matrices and result in interfibrillar and intrafibrillar remineralization. In some embodiments, remineralization of demineralized dentin by the remineralizing restorative material is a self-limiting process, wherein complete remineralization of the collagen or copolymers prevents further mineralization. In other embodiments, water-filled voids that may develop following water sorption of the remineralizing restorative material may be filled with apatites, thereby displacing water that could degrade the stability of the resin-dentin bond. For example, the residual water trapped within the non-resin encapsulated demineralized collagen matrix may be replaced with new apatite crystals. In certain embodiments, remineralizing demineralized dental tissue using a remineralizing restorative material and/or a therapeutic primer may result in the production of nanometer-sized apatite crystals within the collagen matrix that restore the stiffness and strength of the demineralized dentin to levels comparable with normal dentin. In addition, remineralization of demineralized collagen matrix may fossilize the endogenous collagen-degrading enzymes (i.e., matrix metalloproteinases (MMPs)) present in the dental tissue and prevent the collagen fibrils from enzymatic degradation.

In certain embodiments, the method and systems of the present invention may require that the collagen fibrils of the demineralized dentin be structurally sound. In the caries process, superficial collagen may denatured to gelatin, which may cause a loss in gap zones within the fibrils as well as denaturation of NCPs. Such soft, bacterially-contaminated dentin may be referred to as "caries-infected" dentin and is usually treated by clinical removal. The surrounding harder, partially-demineralized dentin is called "caries-affected dentin". The collagen matrix of caries-affected dentin has been shown to have normal cross-linking and normal tensile strength (Miguez et al., *J. Dent. Res.*, 2004, 83:807-810; Nishitani et al., *J. Dent. Res.*, 2005, 84:1075-1078). In some embodiments, the method and systems of the present invention may be able to salvage failing resin-dentin bonds in the hybrid layer of resin-bonded dentin that are created by acid-etch techniques for bonding tooth-colored resin composite fillings to sound and caries-affected dentin, as well as completely- and partially-demineralized non-resin-infiltrated collagen matrices that are found in different regions of a carious dentin lesion. In other embodiments, the mechanical properties of dentin, such as Young's modulus of remineralized dentin collagen matrices, may be restored to values that approximate those of natural, non-carious intertubular dentin so that the remineralized dentin may continue to function as either load bearing or shock absorbing structures for dental restorations or prostheses.

In some embodiments, the progress of remineralization of demineralized dentin can be assessed. For example, the lack of collapse of water-saturated collagen fibrils after dehydration of the dentin can be assessed by, for example, SEM. Alternatively, decreases in water content of remineralizing dentin may be assessed by determining the infiltration of silver nitrate or water-soluble fluorescent dyes into the remineralizing dentin. Alternatively, TEM analysis may be performed.

Figure 19:
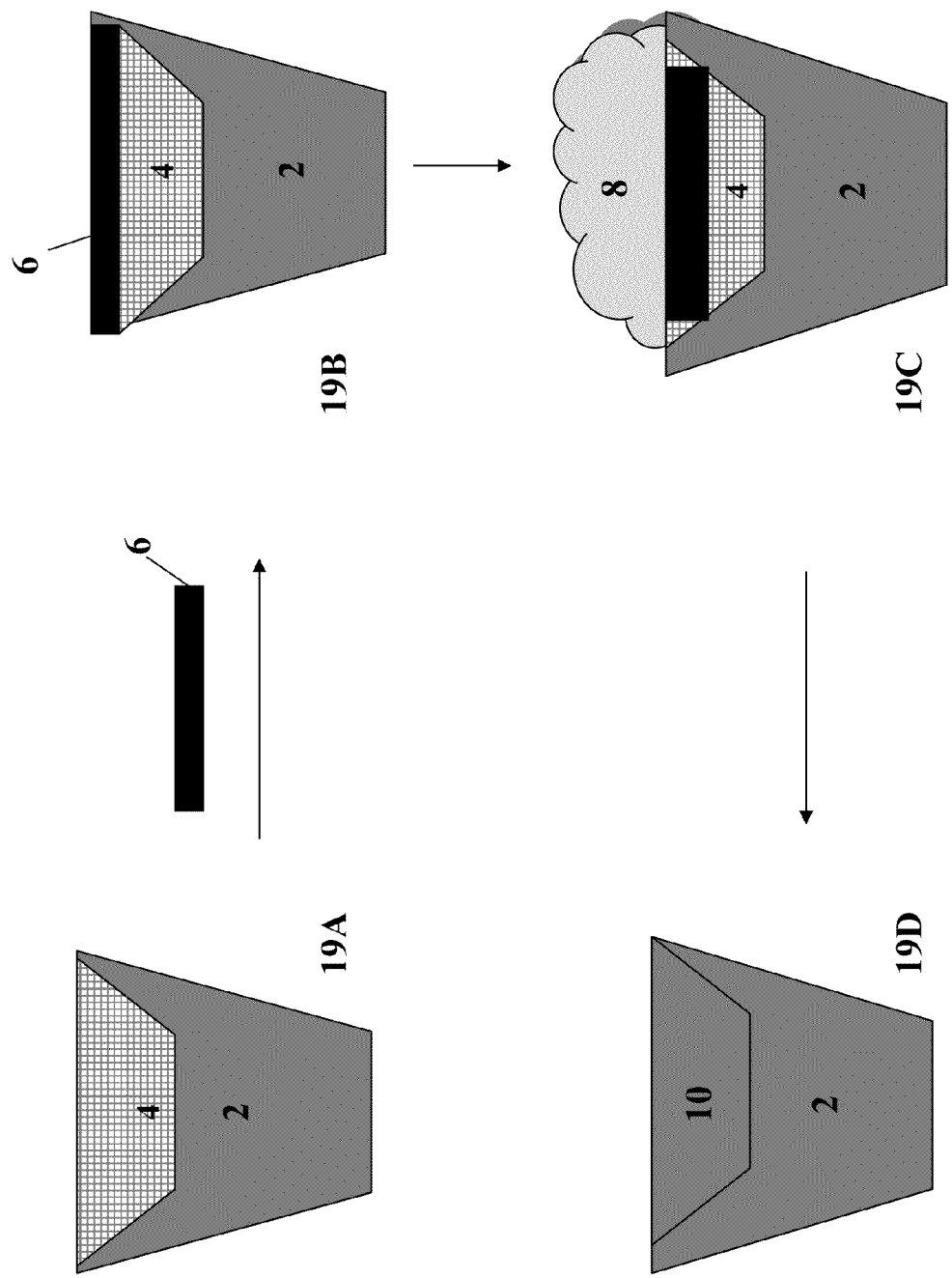
FIG. 19 shows in accordance with some embodiments of the present invention, the method of remineralized demineralized dental tissue.

Thus, as described herein, in certain embodiments, the present invention comprises methods and compositions for mineralization of dental tissue. FIG. 19 shows an illustration of the application of a remineralizing restorative material to a tooth 2 having a region that is demineralized 4. As described herein the remineralizing restorative material comprises a calcium ion source and a hydroxide ion source, wherein the calcium and hydroxide are provided at the site of mineralization at a rate suitable to promote the formation of interfibrillar and intrafibrillar apatite crystals within collagen at the site of mineralization. In the embodiment shown in FIG. 19, the site of mineralization 4 (FIG. 19A) is first exposed to at composition 6 (e.g., a primer) comprising a collagen-binding nucleation factor and a calcium phosphate-binding apatite stabilizer, wherein the collagen-binding nucleation factor promotes interaction of apatite crystals with collagen at the site of mineralization, wherein the calcium phosphate-binding apatite stabilizer maintains the apatite crystals at a size suitable to form as intrafibrillar and interfibrillar crystals at the site of mineralization (FIG. 19B). Generally, the primer may be allowed to interact with the site for several minutes. For example, the primer may be allowed to interact with the site for 1 minute to 1 hour, or 1 minute to 30 minutes, or 2 minutes to 15 minutes, or 2 minutes to 10 minutes, or 2 minutes to 5 minutes or about 3 minutes. This may allow the at least one of a collagen-binding nucleation factor or a calcium phosphate-binding apatite stabilizer to interact with (e.g., diffuse into) the collagen fibrils at the site of mineralization.

Next, and as shown in FIG. 19C, the site 4 is exposed to the second component of the remineralizing restorative material comprising a source of hydroxyl and calcium ions. As described in more detail herein, the remineralizing restorative material may comprise a resin and/or a cement. In this embodiment, the source of phosphate is included in either the primer, or the second component of the remineralizing restorative material 8. Or as noted above, the phosphate source may be provided by saliva or other body fluids, by a physiologically acceptable phosphate-containing solution (e.g., a phosphate-containing buffer or saline-like wash), or by a cement or resin that may be included as part of the remineralizing restorative material.

The tooth may then be incubated in the presence of the calcium and hydroxide source 8, the phosphate source (not shown) and the primer 6 until the demineralized site is remineralized 10 (FIG. 19D). In certain embodiments, remineralization is virtually complete (i.e., 100%) such that the strength of the remineralized tissue (e.g., dentin) 10 is about the same as a normal, healthy tooth.

Figure 20:
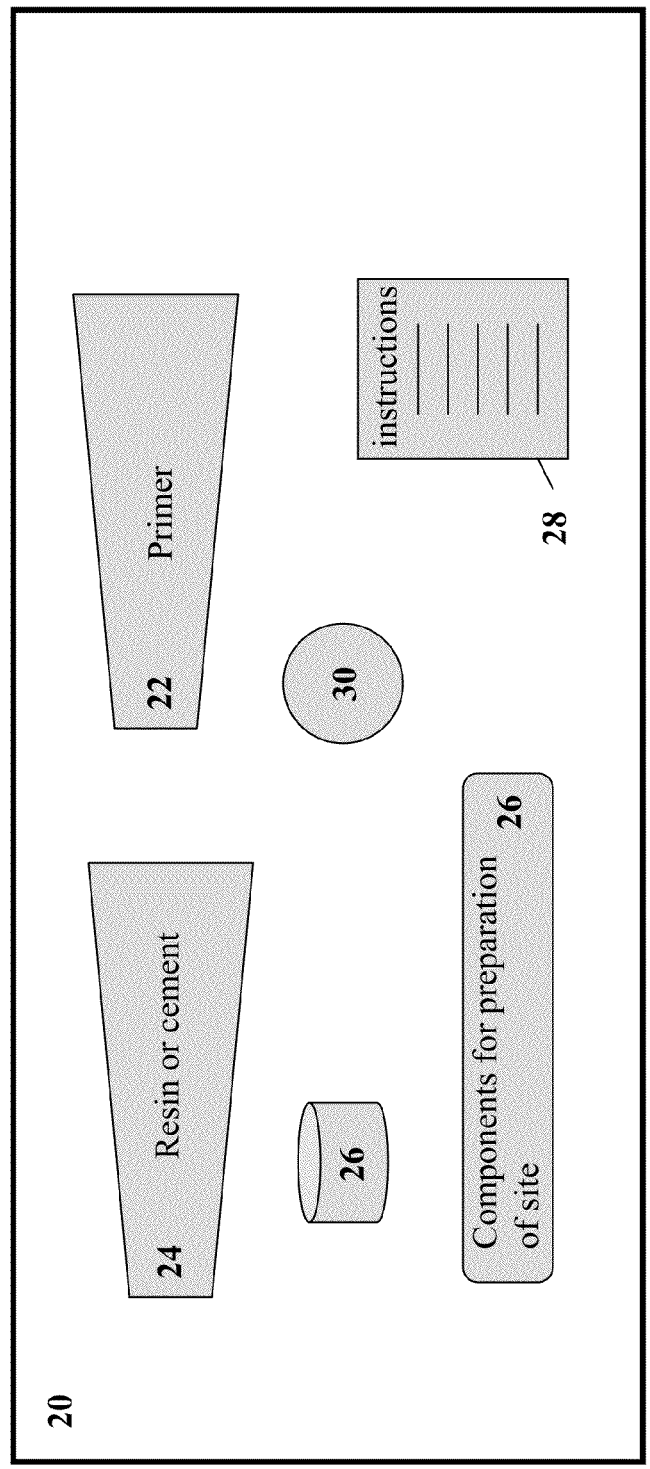
FIG. 20 shows in accordance with some embodiments of the present invention, a kit for remineralizing demineralized dental tissue.

FIG. 20 illustrates a kit of the invention. Thus, as described in more detail herein, the present invention may comprise comprises a kit 20 comprising a remineralizing restorative material. In the embodiment shown in FIG. 20, the remineralizing restorative material is provided as a first primer 22 comprising a collagen-binding nucleation factor and a calcium phosphate-binding apatite stabilizer and a second component 24 (e.g., a resin or cement) comprising a calcium source and a hydroxyl ion source. Also shown is a third component 26 comprising a phosphate source. As noted herein, in some cases the primer 22 or a cement/resin 24 may be a phosphate source. Generally, the kit components may be provided in a sealed container (e.g., tube, syringe) with an opening suitable for delivery of the remineralizing restorative composition to the site of mineralization. Also, the kit may comprise instructions for use 28. The kits may also comprise components 26 that are used in dental repair such as, but not limited to, components for preparation of the site (e.g., such as antibiotics to prevent infection), or additional components that may be added to, or used with, the remineralizing restorative composition, such as an esthetic component comprising a coloring to match the color of the tooth being treated, tools for application of the remineralizing restorative material to a tooth and/or shaping the remineralizing restorative material after application to the tooth, a cap 30 (or other covering) to temporarily cover the site of remineralization, and the like. Also, in the case where components of the remineralizing restorative material are provided as solid(s) (e.g., Portland Cement or the like), the kit may comprise sterile water and/or buffers as may be required to reconstitute any of the formulations.

The present invention may be further understood by reference to the following non-limiting examples.

EXAMPLES

Example 1

A. Materials and Methods

Preparation of Portland Cement:

Type I White Portland Cement (Lehigh Cement Company, Allentown, Pa., USA) was sieved to exclude particles that were coarser than 400 mesh (37 μm). The cement was mixed with deionized water in a water-to-powder ratio of 0.35:1 by weight, placed in flexible silicone bullet molds (Electron Microscopy Sciences, Hatfield, Pa., USA), and allowed to set at 100% relative humidity for one week before use. When hydrated, the major components of the Portland cement, tricalcium silicate and dicalcium silicate react with water to produce a calcium silicate hydrate phase and calcium hydroxide. Leaching of the calcium hydroxide occurs through water that percolates through the microporosities of the set Portland cement and provides the source of calcium and hydroxyl ions for the precipitation of calcium-deficient apatite in phosphate-containing fluid via the formation of an initial amorphous calcium phosphate phase, as previously characterized using X-ray diffraction and Fourier transform infrared spectroscopy (Tay, F. R. et al., *J. Endod.*, 2007, 33:1347-1351).

Remineralization Medium:

Glassware for solution preparation was rinsed with a solution of chromium trioxide (Chromerge Glass Cleaner, Bel-Art Products, Pequannock, N.J., USA) and sulphuric acid, three times with deionized water, followed by acetone and left to oven-dry before use. The remineralization medium was a calcium and magnesium-free phosphate-containing fluid containing 136.9 mM NaCl, 2.7 mM KCl, 8.3 mM $Na_2HPO_4$, and 1.25 mM $KH_2PO_4$ in deionized water, which was prepared and then filtered. For all experiments, a remineralization medium-cement ratio of 15 mL/g was employed so that the phosphate ions were excess (stoichiometric estimation 0.91 mg/mL) and the release of calcium ions (228.6 μg/mL, atomic absorption spectroscopy results) was the limiting parameter in the precipitation reaction.

pH and Turbidimetric Evaluation:

The effect of adding different concentrations of a low molecular weight polyacrylic acid to the remineralization medium on apatite precipitation by set (hardened) white Portland cement was examined. Five remineralization medium solutions containing 0, 100, 500, 1000 and 5000 μg/mL of polyacrylic acid (MW 1,800; Sigma-Aldrich, St. Louis, Ill., USA) were prepared. The pH of each solution was adjusted to 7.3 with Tris(hydroxymethyl)aminomethane and 1 M hydrochloric acid. For each polyacrylic acid concentration, 25 g of set Portland cement were placed in perforated plastic containers, immersed in 500 mL of the respective remineralization medium solution, and agitated with a magnetic stirrer at 37° C. for 180 hours. The pH and optical density of the solutions were measured with a pH meter (AR10, Fisher Scientific, Fair Lawn, N.J., USA) and a microplate reader (VERSAmax, Molecular Devices, Sunnyvale, Calif., USA). For the latter, 200 µL of the solutions was retrieved in triplicates into a 96-well plate at different intervals. The optical densities of the solutions were read against deionized water at 650 nm as a measure of the turbidity of the precipitate produced in the remineralization medium solution.

Morphologic Examination of Calcium Phosphate Precipitates:

Transmission electron microscopy was employed to examine the ultrastructure and crystallinity of the calcium phosphate precipitates before and after the attaining of maximal pH. Accordingly, a second batch of reactions was prepared. Aliquots (20 mL) of each of the precipitate-containing remineralization medium solution were retrieved at 2 h and 180 h. The solutions were centrifuged twice and each lot of the calcium phosphate precipitate was re-suspended in 50 mL deionized water. Two microliter volume drops of each suspension were transferred to carbon-formvar-coated copper grids (Electron Microscopy Sciences, Hatfield, Pa., USA) and allowed to air-dry. The specimens were examined using a JEM-1010 transmission electron microscope (JEOL, Tokyo, Japan) at 80 KeV.

Remineralization of Acid-Etched Dentin Disks:

Remineralization medium containing 500 µg/mL of polyacrylic acid and 200 µg/mL of PVPA (Sigma-Aldrich; MW 62000) and with the pH adjusted to 7.3 was used in the subsequent experiments. Twenty-four human third molars were collected after patients' informed consent were obtained under a protocol reviewed and approved by the Human Assurance Committee of the Medical College of Georgia. A flat coronal dentin surface was prepared perpendicular to the longitudinal axis of each tooth with a slow-speed Isomet saw (Buehler Ltd., Lake Bluff, Ill., USA) under water-cooling. A second parallel cut was made 3 mm below the cement-enamel junction. Pulpal tissues were removed from the pulp chamber. Each dentin disk was polished with 600-grit silicon carbide paper under running water. A partially demineralized dentin model was used in which the sound coronal dentin was acid-etched with a 37% phosphoric acid gel (Etch 37, Bisco Inc., Schaumburg, Ill., USA) for 15 sec, and rinsed with deionized water to create a 5 µm thick layer of mineral-free collagen matrix on the surface of the mineralized dentin base (Tay, F. R. et al., *J. Dent. Res.*, 2003, 82:537-541). This acid-etching protocol is commonly employed in clinical bonding of dentin adhesives. Although 30 min of EDTA demineralization also produces a demineralized dentin layer of similar thickness, such a layer exhibits a gradient of apatite dissolution with residual crystallites available for crystal growth (Nakabayashi N. et al., *Dent. Mater.*, 1992, 8:259-264). As such, EDTA demineralization was not a suitable protocol for the purposes of this study as it precludes the determination of whether dentin remineralization can occur by either spontaneous precipitation or by nucleation of minerals directly on the organic matrix. However, this method may be suitable for use in practice with patients where residual crystallites available for growth in the dental tissue is beneficial for biomimetic mineralization.

Twenty acid-etched dentin disks were used for the remineralization experiment. Each dentin disk was placed in a glass vial filled with 20 mL of remineralization medium containing 500 µg/mL of polyacrylic acid and 200 µg/mL of PVPA. One gram of set Portland cement was placed inside a perforated plastic microtube, inserted into the glass vial and allowed to float on top of the remineralization medium. Each glass vial was capped to prevent evaporation of the solution and stored in an incubator at 37° C. Ultrastructural examination was performed on five dentin disks after 2, 4, 6 and 8 weeks of remineralization. Two acid-etched dentin disks were used as the first negative control. Each disk was placed in a glass vial filled with 20 mL of remineralization medium without polyacrylic acid and PVPA. Set Portland cement was placed in the glass vial as previously described. The last two acid-etched dentin disks were used as the second negative control. Each disk was placed in a glass vial filled with 20 mL of remineralization medium containing 500 µg/mL of polyacrylic acid only. Set Portland cement was placed in the glass vial as previously described. Ultrastructural examination was performed on these negative control dentin disks after 8 weeks of remineralization. At the end of each designated remineralization period, each dentin disk was retrieved from the glass vial, rinsed with deionized water and ultrasonicated in 50% ethanol for 3 min before processing for ultrastructural examination.

Scanning Electron Microscopy:

A slit was made along the pulpal side (i.e., side with intact mineralized dentin) of each dentin disk using the Isomet saw under water cooling to facilitate subsequent cryofrature of the dentin disks. Each dentin disk was immersed in liquid nitrogen for 2 min and dropped into deionized water. Expansion of the ice within the water-filled slit resulted in spontaneous splitting of the dentin disk into two halves. One half of each disk was dehydrated in an ascending series of ethanol (50-100%), and immersed in hexamethyldisilasane that was allowed to evaporate slowly during the final chemical dehydration step. The specimens were sputter-coated with gold/palladium and examined along their fractured edges using a field emission-scanning electron microscope (XL-30 FEG; Philips, Eindhoven, The Netherlands) operated at 5 kV.

Transmission Electron Microscopy (TEM):

The other half of each cryofractured dentin disk was sectioned in a coronal-pulpal direction into 1-mm thick slices. The slices were fixed in Karnovsky's fixative, rinsed in cacodylate buffer, post-fixed in 1% osmium tetroxide, and further rinsed three times in cacodylate buffer. The slices then were dehydrated in an ascending series of ethanol (50-100%), immersed in propylene oxide as a transitional fluid and subsequently embedded in epoxy resin. Non-demineralized, epoxy resin-embedded, 70-90 nm thick sections were prepared with an ultramicrotome (Ultracut S, Leica, Vienna, Austria) and a diamond knife (Diatome, Hatfield, Pa., USA) and examined without further staining using a the JEM-1230 transmission electron microscope operated at 80 kV.

B. Results

The time-dependent changes in pH and optical density of the precipitate-containing remineralization medium solutions are shown in FIG. 3, Panels A and B, respectively. The pH profiles of the remineralization medium solutions were characterized by initial rapid rises to maximum pH followed by gradual declines in pH with time (FIG. 3A). Such pH changes are indicative of a two-stage reaction: initial production of amorphous calcium phosphate during the first stage, and the consumption of OH⁻ ions to form apatite during the second stage. The maximum pH attained decreased with increasing polyacrylic acid concentrations. Increase in optical densities of the remineralization medium solutions was used as an indirect measure of the amount of calcium phosphate precipitated (Bradt, J. H. et al., *Chem. Mater.*, 1999, 11:2694-2701). Optical density profiles of the remineralization medium solutions were characterized by increases in turbidity of the precipitates during the time period examined (FIG. 3B). The overall turbidity of the remineralization medium containing 100 μg/mL of polyacrylic acid was higher than that of the control that contained no polyacrylic acid. Conversely, turbidity measurements for the other three polyacrylic acid concentrations were all lower that the control, in the order 500>1000>5000 μg/mL. These results suggest that polyacrylic acid is a promoter of apatite nucleation/growth at 100 μg/mL, but an inhibitor at concentrations greater than 500 μg/mL. FIGS. 3C-F shows TEM images of calcium phosphate precipitates retrieved from the PCF solutions with different polyacrylic acid concentrations. In the absence of polyacrylic acid, TEM of the purified precipitates formed prior to attaining maximum pH (retrieved at 2 hr) revealed the presence of amorphous calcium phosphate globules (pointer; 300 nm diameter), with evidence of transformation into apatites (open arrowheads)(FIG. 3E) (Tay, F. R. et al., *J. Endod.*, 2007, 33:1347-1351). Complete transformation of the amorphous calcium phosphate into apatite crystallite clusters occurred by the end of the experimental period (180 hrs). These acicular crystallites were 200-250 nm long along their c-axes (FIG. 3E). When 100 μg/mL of polyacrylic acid was included in the PCF, smaller apatite crystallites (75-100 nm along the c-axis; between open arrowheads) were formed, which exhibited side-to-side and end-to-end alignments (FIG. 3E). At polyacrylic acid concentrations of 500-5000 μg/mL, only very small amorphous calcium phosphate nanospheres with diameter smaller than 50 nm were present (FIG. 3F; between open arrowheads).

FIG. 4 shows the results of two negative control conditions tested. In the first negative control condition, acid-etched dentin was immersed in the Portland cement-PCF system without polyacrylic acid and polyvinyl phosphonic acid (PVPA) (FIGS. 4A-D). In the second negative control condition, acid-etched dentin was immersed in the Portland cement-PBS system containing 500 μg/mL of polyacrylic acid only (i.e., no PVPA) (FIG. 4E and FIG. 4F). In the first negative control, when the phosphoric acid-etched dentin specimens were immersed in the Portland cement-remineralization medium system without polyacrylic acid or PVPA, only surface deposition of amorphous calcium phosphate-derived apatite clusters was apparent on the top of the demineralized collagen matrix (FIGS. 4A-2D). In FIG. 4A, FESEM of a cryofractured specimen showing only surface deposition of apatite clusters (open arrowhead) on the top of the demineralized collagen matrix. FIG. 4B shows a corresponding unstained TEM depicting a 5 μm thick layer of demineralized dentin (between open arrows) wherein a diffuse selected area electron diffraction pattern (SAED, inset) taken from the middle of the demineralized dentin indicates the complete absence of minerals (open arrowhead: apatite clusters). The dark clusters indicated by the white arrowheads are aggregates of large apatite crystalline clusters seen on the dentin surface as in FIG. 4A. In FIG. 4C, high magnification FESEM shows comparatively smooth, partially-collapsed collagen fibrils with the absence of banding characteristics (arrow), while FIG. 4D shows a high magnification unstained TEM of a single apatite cluster with comparatively large crystals (100-200 nm) formed around a hollow center. The latter represents the space occupied by the original amorphous calcium phosphate phase before it was converted into apatite by outward growth. In FIG. 4A and FIG. 4C, note the smooth, spaghetti-like appearance of the demineralized collagen fibrils (D) beneath the overlying clusters of very large apatite crystals, and the empty spaces between the collagen fibrils. Although apatite minerals were observed to precipitate on top of the demineralized dentin in this negative control, the apatite minerals were too large to be formed within the collagen fibrils. As such, the underlying collagen matrix remains very soft and weak and can not provide a strong foundation for dental restorations.

Figure 4A:
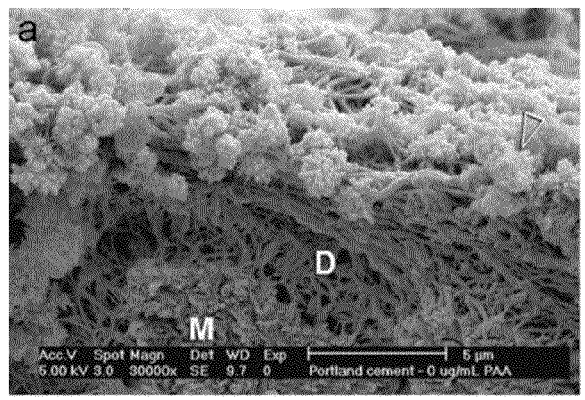
FIG. 4 shows in accordance with alternate embodiments of the present invention, two negative controls illustrating the absence of remineralization in phosphoric acid-etched dentin: PCF containing no biomimetic molecules and PCF containing only 500 µg/mL of polyacrylic acid only (i.e., no PVPA); Abbreviations: D, demineralized dentin; M, underlying unetched mineralized dentin.
Figure 4B:
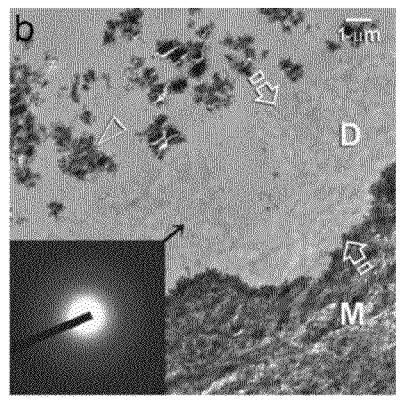
Figure 4C:
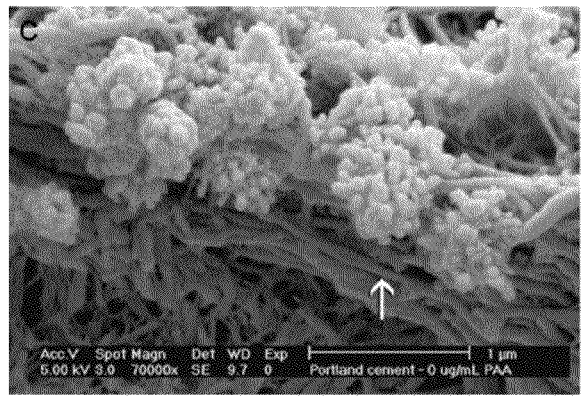
Figure 4D:
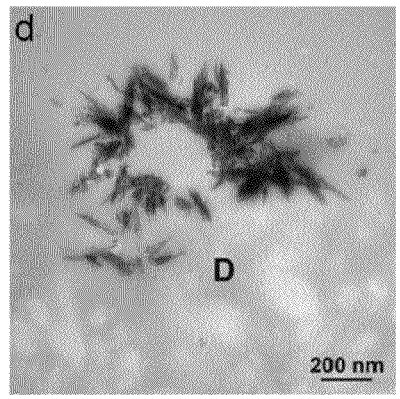
Figure 4E:
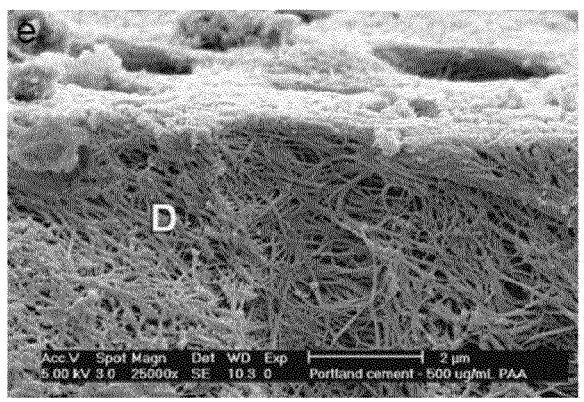
Figure 4F:
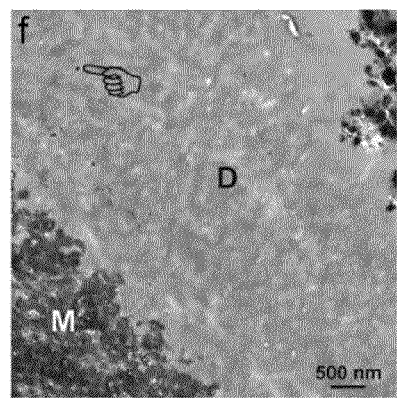
Figure 4G:
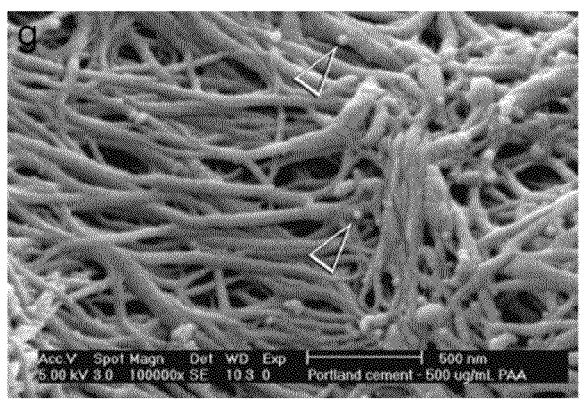
Figure 4H:
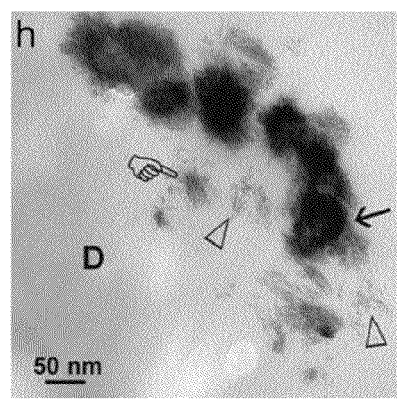
Figure 6A:
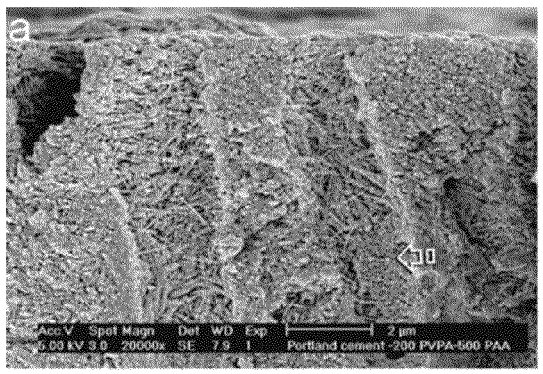
FIG. 6 shows in accordance with alternate embodiments of the present invention, continuous intrafibrillar and interfibrillar remineralization at 4 weeks after phosphoric acid-etched dentin immersion in the Portland cement-PCF system containing 500 µg/mL of polyacrylic acid and 200 µg/mL of PVPA in accordance with one embodiment of the present invention; Abbreviations: T, dentinal tubules.
Figure 6B:
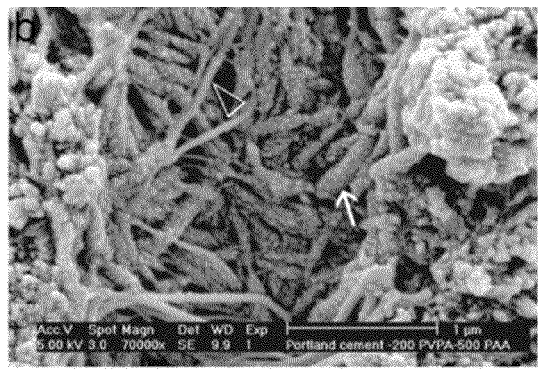
Figure 6C:
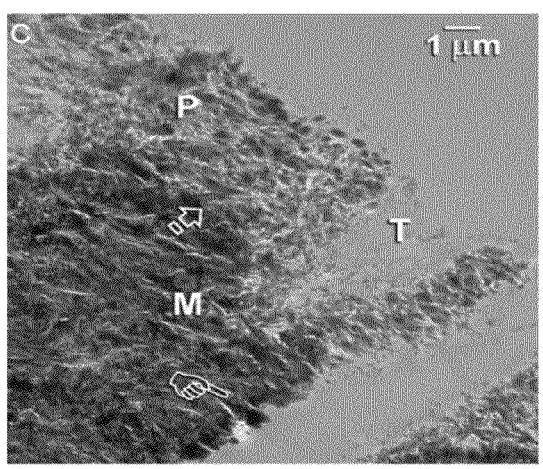
Figure 6D:
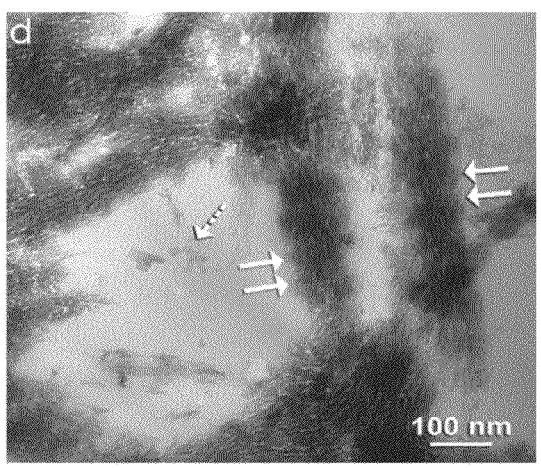
Figure 6E:
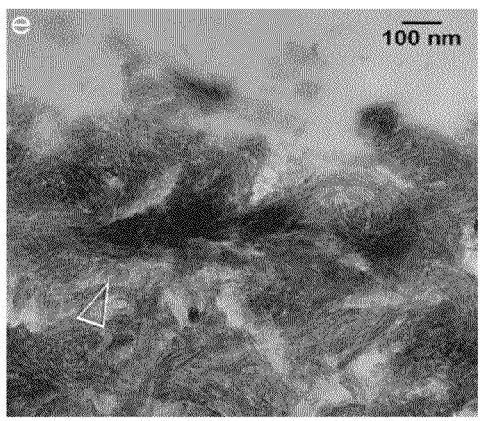

Likewise, remineralization in the second negative control was not evident when the acid-etched specimens were immersed in the remineralization system containing 500 μg/mL of polyacrylic acid only for the same time periods (FIG. 4E and FIG. 4F). FIG. 4E depicts a FESEM showing a partially collapsed collagen matrix with no evidence of remineralization. Collagen fibrils appeared shrunken as a result of chemical dehydration, with wide interfibrillar spaces. Polyacrylic acid-stabilized amorphous calcium phosphate nanospheres were occasionally seen within demineralized collagen matrix (FIG. 4F and FIG. 4G). Under high magnification, these nanospheres had been partially transformed into apatite nanocrystals. FIG. 4F depicts a corresponding unstained TEM of the demineralized dentin matrix. Electron-dense amorphous calcium phosphate nanoprecursors were predominantly seen on the dentin surface but a few nanoprecursors did infiltrate the demineralized dentin (FIG. 4F: pointer). FIG. 4G depicts a high magnification FESEM showing the nanoprecursors (open arrowheads) depicted in FIG. 4F. Each 5-10 nm long apatite nanocrystal was probably also stabilized by polyacrylic acid anions and exhibited a tendency to self-assemble (FIG. 4H). FIG. 4H shows a high magnification unstained TEM of the nanoprecursors on the dentin surface (arrow) that had been partially transformed into apatite nanocrystals (ca. 5-10 nm long; open arrows).

Initial intrafibrillar and interfibrillar remineralization appeared as early as at 2 weeks after acid-etched dentin was immersed in the Portland cement-remineralization medium system containing 500 μg/mL of polyacrylic acid and 200 μg/mL of PVPA (FIG. 5). FESEM of cryofractured dentin showed collapse (open arrow) of the surface layer of unsupported demineralized dentin matrix (D), and regions of partially remineralized dentin (P) exhibited minor shrinkage and resulted in the appearance of a step (open arrowhead) between them and the underlying intact unetched mineralized dentin (M) (FIG. 5A). These partially remineralized regions of dentin extended from the base of the 5 μm thick (between open arrows) demineralized dentin layer (D) toward the dentin surface (FIG. 5B; corresponding unstained TEM). High magnification FESEM revealed the presence of numerous amorphous calcium phosphate nanospheres (open arrowheads) along the surface of the collagen fibrils. The fibrils exhibited discontinuous regions of periodicity (pointer) that resisted dehydration shrinkage (as compared to adjacent shrunken segments of fibrils without periodicity) (FIG. 5C). A grey substance is identifiable within that zone that offers some resistance to the passage of electrons. Based on these results, the degree of partial mineralization in region P appears to be about one-tenth that of the underlying mineralized dentin which offers a great deal of resistance to the passage of electrons through these thin sections. These features are suggestive of the presence of mineral support within the collagen fibrils (intrafibrillar remineralization), which was confirmed using high magnification TEM (FIG. 5D; nanoprecursors: arrowhead; collagen fibril: between open arrowhead). In addition, in the more highly remineralized regions, nanoprecursors could be seen around banded collagen fibrils (open arrowhead), and collagen fibrils exhibited a "corn-on-the-cob" appearance (arrow) that is suggestive of interfibrillar remineralization (FIG. 5E). In FIG. 5E, the pointer indicates a single collagen fibril that has developed intrafibrillar mineral crystals that make the collagen fibril thicker than the adjacent narrower part of the same collagen fibril that has not yet formed intrafibrillar minerals. This was confirmed using TEM, which showed the presence of interfibrillar and intrafibrillar apatite nanocrystals along the periphery of the collagen fibrils (between open arrows) (FIG. 5F). Another TEM specimen with more extensive remineralization is shown in FIG. 5G where remineralization extends almost to the dentin surface (open arrowheads), with only a thin zone of demineralized dentin remaining (i.e., between open arrowheads and open arrows), although the electron density of the partially remineralized dentin matrix was still lower than that of the underlying intact, unetched mineralized dentin. Upon higher magnification, in this specimen it was determined that the intrafibrillar spaces were almost completely occupied by apatite nanocrystals (FIG. 5H).

Continuous intrafibrillar and interfibrillar remineralization that occurred after 4 weeks are illustrated in FIG. 6. It was difficult to distinguish the remineralized dentin matrix from the underlying intact mineralized dentin using FESEM, except for the absence of peritubular dentin around the orifices of the dentinal tubules (FIG. 6A). FESEM analysis indicated that the remineralized dentin attained enough support to prevent it from collapse or shrinkage during high vacuum SEM examination. Peritubular dentin (open arrow) was absent from the superficial 5 μm of the dentinal tubules. At higher magnification, it was apparent that the majority of the collagen fibrils exhibited the "corn-on-the-cob" appearance (arrow), representative of interfibrillar mineralization, while other smaller diameter fibrils were devoid of interfibrillar minerals and exhibited only faint banding characteristics (open arrowhead) (FIG. 6B). Low magnification TEM showed that the partially remineralized dentin (open arrowhead) was not as mineral-dense as the underlying intact mineralized dentin (i.e., the two were easily discernable), and dentinal tubular orifices within the partially remineralized dentin were also completely devoid of peritubular dentin (FIG. 6C). However, the partially remineralized zone (P) seems to contain about one-third of the mineral that is seen in the underlying mineralized dentin (M). A circumferential layer of more electron-dense peritubular dentin (pointer) could be seen further down the dentinal tubules (T). Upon higher magnification, intrafibrillar mineralization can be seen in the form of very fine, electron-dense strands that follow the microfibrillar subunits within the collagen fibril of the partially remineralized dentin (FIG. 6D). These fibrils were filled with apatite nanocrystals that were oriented along the longitudinal axes of the microfibrils, enabling the rope-like subfibrillar architecture of the collagen fibrils to be discerned (Bozec, L. et al., *Biophys. J.*, 2007, 92:70-75). This increases the stiffness of collagen enormously. Corrugation of these fibrils at regular intervals (ca. 70 nm) corresponded with the banding characteristics observed when similar fibrils were examined using FESEM as shown in FIG. 6C. This hint of periodicity to the intrafibrillar mineralization, as shown by the double solid arrows, suggests that, at this stage, the mineral density increases and then decreases and then increases again over 50 nm distances in the hole zones of the collagen fibrils. Note that these nanocrystals are less than 50 nm long (dotted white arrow). No interfibrillar mineral has formed yet in this region. The electron dense material beyond the tip of the white dashed arrow is thought to represent the conversion of amorphous calcium phosphate into calcium phosphate nanoparticles. Apatite platelet formation, probably via mesoscopic transformation of the nanocrystals (dashed arrow) could be seen in electron-lucent areas adjacent to the remineralized collagen fibrils. Transition from apatite nanocrystals to larger crystallites with plate-like morphology (open arrowhead) was considerably more evident within the more electron-dense regions of the partially remineralized dentin at higher magnifications (FIG. 6E).

Figure 7A:
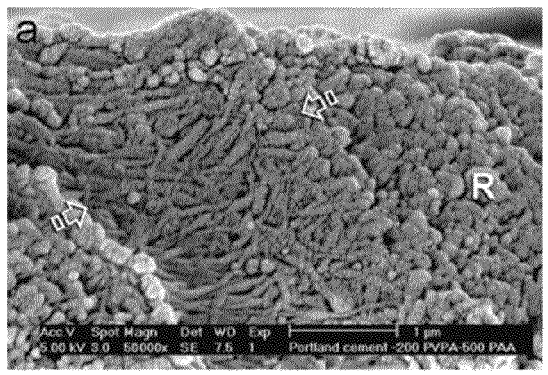
FIG. 7 shows in accordance with alternate embodiments of the present invention, complete dentin remineralized after immersion for 8 weeks in the Portland cement-PCF system containing 500 µg/mL of polyacrylic acid and 200 µg/mL of PVPA in comparison with intact mineralized dentin in accordance with one embodiment of the present invention; Abbreviations: R, remineralized collagen fibrils; M, mineralized dentin; T, dentin tubule.
Figure 7B:
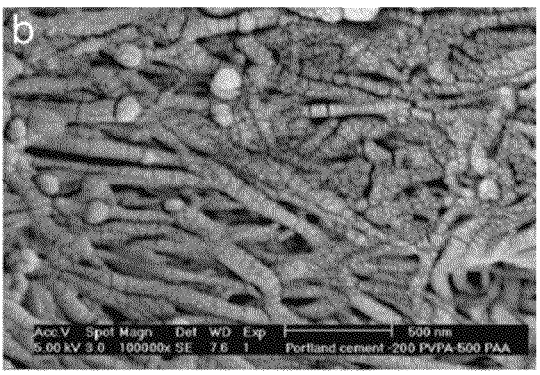
Figure 7C:
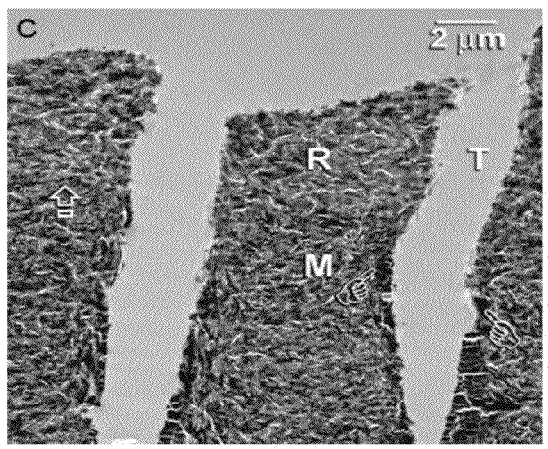
Figure 7D:
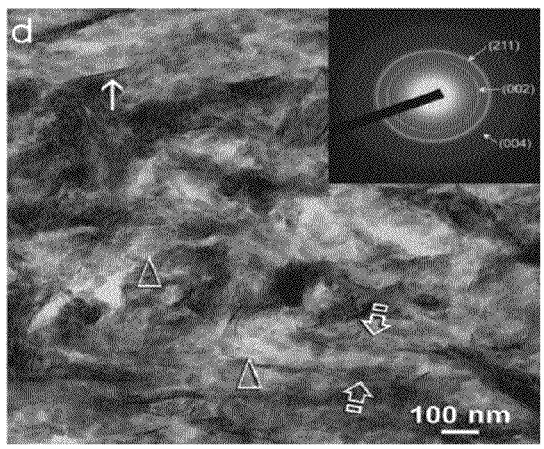
Figure 7E:
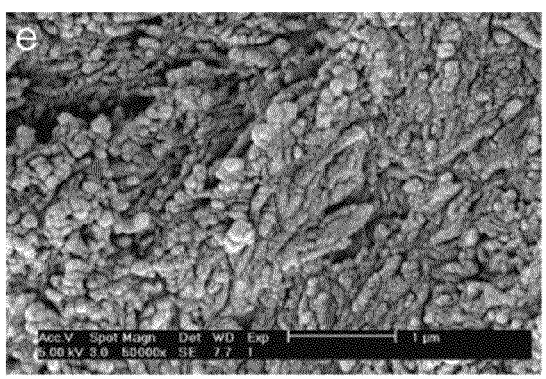
Figure 7F:
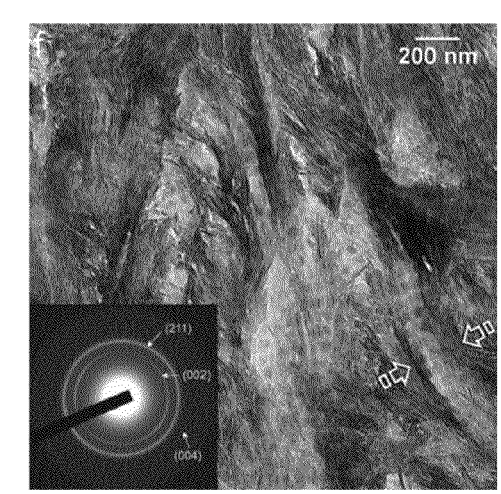

Complete remineralization of the exposed 5-6 μm thick collagen matrix (i.e., the remineralization zone on the top of the sample) was evident by FESEM examination as early as 6 weeks, but was more consistently observed at 8 weeks (FIG. 7A and FIG. 7B) (higher magnification of the 50-100 nm diameter remineralized collagen fibrils). FESEM of the cryofractured dentin surface showed completely remineralized collagen fibrils (R) and that the periphery of the dentinal tubule orifice (between open arrows) was completely devoid of peritubular dentin. A corresponding TEM image revealed the location of the original demineralization front between the zone of remineralized dentin (R) and the underlying intact mineralized dentin (M) (FIG. 7C). The original demineralization front could be vaguely discerned (arrow). Peritubular dentin could only be found (pointer) further down the dentinal tubule (T). The superficial 8-10 μm of the dentinal tubule orifice was devoid of peritubular dentin. During remineralization, no hypermineralized intratubular matrix was formed because there were no demineralized collagen fibrils to bind polyvinylphosphoric acid to form the initial nidus for remineralization of collagen fibrils doped with biomimetic polyanions to guide the location and scale of remineralization (Tay and Pashley, Biomaterials, 2008, 29:1127-1137). Corresponding high magnification TEM imaging revealed the presence of both intrafibrillar and interfibrillar apatite crystallites with the collagen fibrils (between open arrows) (FIG. 7D), although they were not as well organized as those present in intact mineralized dentin (control) ((FIG. 7E) (FESEM) and FIG. 7F (unstained TEM)). Some of the intrafibrillar crystallites were arranged into an approximately 70 nm periodic distribution of 40 nm long, non-overlapping platelets that were smaller than the adjacent 100 nm long interfibrillar apatite crystallites (arrow). FIG. 7D depicts a single collagen fibril about 100 nm wide (between white arrows) that shows intrafibrillar apatite crystallites arranged in bands that are approximately 67 nm apart. Nanometer-sized apatite crystallites have formed in the gap regions of the collagen fibrils (open arrowheads), appearing as gray bands because they are oriented sideways in these views. The dimensions of the apatite crystals formed in the gap regions are about 80 nm long and only 4 nm thick. The interfibrillar crystals (white arrow) shown in FIG. 7D, appear as black (i.e. electron-dense) needles. When these crystals were submitted to selected area electron diffraction (SAED insert, FIG. 7D), the remineralized crystallites exhibited ring patterns that are characteristics of the [002], [004] and the major [211] crystal planes characteristic of poorly crystalline apatites present in intact mineralized dentin.

C. Discussion

Careful examination of all specimens undergoing remineralization after two weeks, as shown specifically, for example, in FIG. 3, reveals that remineralization commenced from the base of the demineralized dentin layer toward the surface. These results indicate that certain substances may elute from the underlying mineralized dentin that may facilitate the remineralization process. For example, it has been shown that phosphoprotein and proteoglycans are released from dentin during the period of neutral pH that followed acid demineralization (Klont, B. et al., *J. Dent. Res.*, 1990, 69:896-900). In addition, highly alkaline solutions of both calcium hydroxide and Mineral Trioxide Aggregate were able to extract non-collagenous proteins, glycosaminoglycans and growth factors such as TGF-β1 from mineralized dentin. Hence, the term "guided tissue remineralization" is used to recognize this additional contribution from the mineralized dentin base.

As illustrated in this Example, the present invention provides the first evidence of remineralization as the growth of nanometer-sized (i.e., 70×40×4 nm crystallites) apatite crystallites initially in the hole zones of intrinsic, demineralized collagen fibrils that are continuous with underlying mineralized collagen fibrils, followed by more randomly oriented crystal growth in the 20 nm wide interfibrillar spaces. Remineralization of dentin that does not meet these parameters is not true remineralization of dentin and will not stiffen collagen to values of 15-20 GPa (Kinney et al., 2003).

Example 2

A. Materials & Methods
Dentin Bonding:

Twenty recently extracted human third molars were collected after donors' informed consents were obtained under a protocol reviewed and approved by the Human Assurance Committee of the Medical College of Georgia. A flat dentin surface was prepared perpendicular to the longitudinal axis of each tooth by means of a slow-speed Isomet diamond saw (Buehler Ltd, Lake Bluff, Ill., USA) under water-cooling to simulate tooth cavities that are prepared in human teeth clinically. The bonding surface was further polished with a 400-grit silicon carbide paper attached to create a bonding surface in mid-coronal dentin. Two simplified etch-and-rinse adhesives were used: One-Step (Bisco Inc., Schaumburg, Ill., USA), a water-free, acetone-based unfilled adhesive; and Single Bond Plus (3M ESPE, St. Paul, Minn., USA), a water-containing, ethanol-based filled adhesive. Ten teeth were randomly assigned to each adhesive. Each dentin surface to be bonded was etched with a 32% phosphoric acid gel (Uni-Etch, Bisco, Inc.) for 15 sec to create a 5- to 8-μm-thick zone of completely demineralized dentin on top of a mineralized dentin base. The etched dentin surface was thoroughly rinsed with de-ionized water, and bonded with the respective adhesive by keeping the etched dentin visibly moist during bonding. After evaporation of the adhesive solvent, each adhesive was polymerized for 20 sec with a quartz-tungsten-halogen light-curing unit with an output intensity of 600 mW/cm$^2$. This was followed by incremental placement of two 2-mm-thick layers of a resin composite that was light-cured separately for 40 sec. Each tooth was then sectioned occluso-gingivally into 1-mm-thick slabs, each containing the resin-dentin interface in the center of the slab.

Remineralization Medium:

Type I white Portland cement (major components: $3CaO.SiO_2$, $2CaO.SiO_2$, $3CaO.Al_2O_3$, and $CaSO_4.2H_2O$; Lehigh Cement Company, Allentown, Pa., USA) was mixed with de-ionized water in a water-to-powder ratio of 0.35:1, placed in flexible silicone molds, and allowed to set and age at 100% relative humidity for 1 wk before use (Tay, F. R. et al., J. Endod., 2007, 33:1347-1351).

A simulated body fluid (SBF) was prepared by dissolving 136.8 mM NaCl, 4.2 mM $NaHCO_3$, 3.0 mM KCl, 1.0 mM $K_2HPO4.3H_2O$, 1.5 mM $MgCl_2.6H_2O$, 2.5 mM $CaCl_2$, and 0.5 mM $Na_2SO_4$ in de-ionized water (Kokubo, T. et al., J. Biomed. Mater. Res., 1990, 24:721-734) and adding 3.08 mM sodium azide to prevent bacterial growth. The SBF was buffered to pH 7.4 with 0.1 M Tris Base and 0.1 M HCl and filtered. For biomimetic remineralization, 500 μg/mL of polyacrylic acid (PAA) (MW 1800; Sigma-Aldrich, St. Louis, Mo., USA) and 200 μg/mL of polyvinylphosphonic acid (PVPA) (MW 62,000; Sigma-Aldrich) (Munisamy, S. et al., J. Oral Implantol., 2008, 34:67-75; Tay, F. R. et al., Biomaterials, 2008, 29:1127-1137; Pashley, D. H. et al., J. Dent. Res., 2004, 83:216-221) were added to the SBF as biomimetic analogs of NCPs found associated with type I collagen in dental tissue. The pH of the PAA-PVPA-containing solution was adjusted to 7.4.

Biomimetic Remineralization:

Each experimental specimen slab containing the resin-dentin interface was placed on top of a set Portland cement block (ca. 1 g) inside a glass scintillation vial. The latter was filled with 15 mL of SBF containing the two biomimetic analogs. The setup for the control specimens was the same, except that the liquid medium was replaced with SBF that did not contain biomimetic analogs. Each glass vial was capped to prevent evaporation of the solution and incubated at 37° C. Experimental specimens were retrieved after 1, 2, 3, and 4 months (N=5) for ultrastructural examination of the extent of remineralization. Control specimens were examined at the baseline period (i.e., before immersion) and after 4 months of immersion in the Portland cement/SBF.

Transmission Electron Microscopy:

Following retrieval from the respective solution, the specimen slices were fixed in Karnovsky's fixative, rinsed in cacodylate buffer, post-fixed in 1% osmium tetroxide, and further processed as previously reported (Tay, F. R. et al., J. Adhes. Dent., 1999, 1:103-117). Non-demineralized, epoxy-resin-embedded, 90-nm-thick sections were prepared and examined, without further staining, by means of a JEM-1230 transmission electron microscope (JEOL, Tokyo, Japan) operated at 80 kV. For the control group, two additional specimens were immersed in 50 wt % ammoniacal silver nitrate for silver nanoleakage examination within the dentin hybrid layers, according to our previously reported protocol (Tay, F. R. et al., J. Dent. Res., 2002, 81:472-476). After reduction of the diamine silver ions into metallic silver, the specimens were processed and examined in the manner described above.

B. Results
Control Specimens:

Hybrid layers of One-Step or Single Bond Plus did not remineralize after 4 months of immersion in Portland cement/SBF without biomimetic analogs. FIG. 8A shows a transmission electron micrograph (MC) of a One-Step specimen with a 5- to 8-μm-thick hybrid layer that was completely devoid of apatite minerals. Electron diffraction of the mineralized dentin base beneath the hybrid layer revealed concentric rings (major hkl plane indices included) that are characteristic of small crystalline aggregates (FIG. 8B). The two most prominent rings (asterisks) represent the [002] plane, and the closed approximated [211], [112], [300], and [202] planes of apatite (FIG. 8B). FIG. 8E shows a Single Bond Plus specimen with a completely demineralized hybrid layer with a similar thickness range (i.e., 5-8 μm). Nanoleakage (silver uptake) could be identified from these hybrid layers after 4 mos of immersion in the control medium. FIG. 8F depicts nanoleakage in a Single Bond Plus specimen (pointer: nanoleakage within hybrid layer; open arrowheads: silver-filled water channels (i.e., water trees) within the filled adhesive layer). Large (3-4 μm diameter) silver deposits were water droplets in the adhesive layer. In addition, the One-Step adhesive exhibited a porous region in which water eluting from the dentin surface was trapped by light-curing of the adhesive (Tay, F. R. et al., Oper. Dent., 2005, 30:561-579), with severe nanoleakage beneath the resin composite. FIG. 8C shows silver permeation into water-filled interfibrillar spaces (pointer) identified from the hybrid layer of a specimen bonded with One-Step. FIG. 8D shows leaching of resinous components from a water-rich zone beneath the resin composite resulted in the manifestation of multiple isolated silver grains (open arrowhead) within the unfilled adhesive.

Figure 9A:
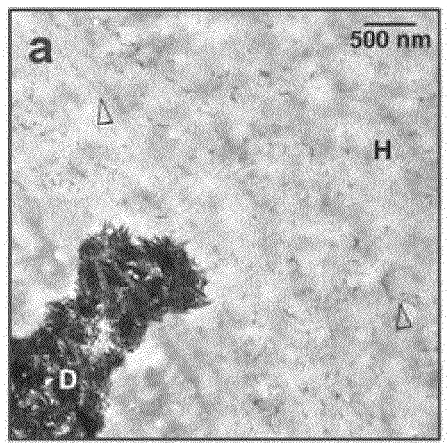
FIG. 9 shows in accordance with alternate embodiments of the present invention, experimental specimens having undergone biomimetic remineralization for 1-2 mos exhibit two subtle stages of remineralization within hybrid layers: the initial stage of amorphous nanoprecursor coalescence (Panels A-C) and the subsequent initiation of interfibrillar remineralization (Panels D-F) in accordance with alternate embodiments of the present invention; Abbreviations: C, composite; A, unfilled adhesive; FA, filled adhesive; H, hybrid layer; D, mineralized dentin.
Figure 9B:
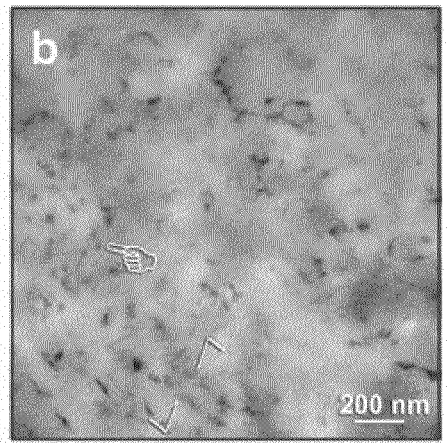
Figure 9C:
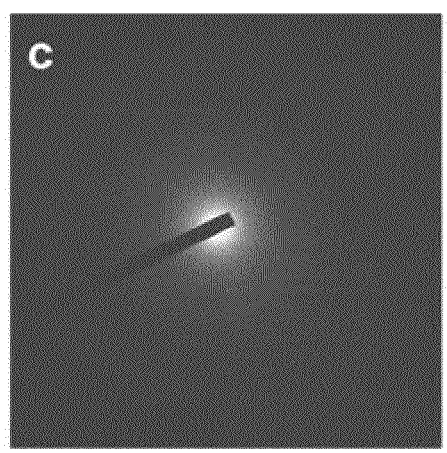
Figure 9D:
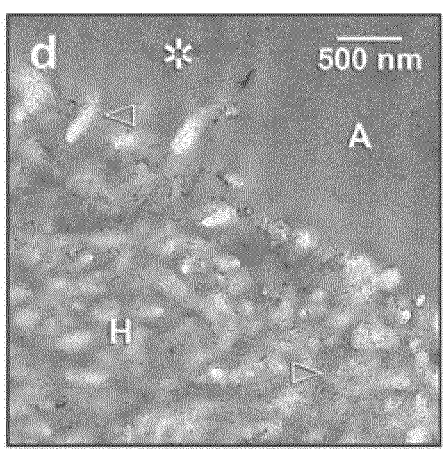

Experimental Specimens:

Progressive remineralization of the resin-dentin interfaces was identified for both adhesives. The first ultrastructural changes that occurred at 1 mo were subtle and not discernible below 5000× magnification. A One-Step specimen retrieved after 1 mo of biomimetic remineralization showed unusual electron densities (i.e., amorphous electron-dense structures (open arrowheads)) along the interfibrillar spaces of the hybrid layer (FIG. 9A). A higher-magnification view (FIG. 9B) revealed electron-dense, amorphous structures (arrowheads) that likely represent coalesced fluidic amorphous calcium phosphate nanoprecursors that had penetrated the incompletely infiltrated regions of the hybrid layer. Selected Area Electron Diffraction (SAED) of these amorphous structures resulted in a broad, diffuse pattern without concentric rings (FIG. 9C), indicating their non-crystalline status. A One-Step specimen, taken 2 mos after remineralization, showed the presence of very fine needle-shaped nanocrystals (open arrowheads) within interfibrillar spaces of the hybrid layer (FIG. 9D). These nanocrystals are smaller than the apatites that are found in natural mineralized dentin. Fine mineral deposits could also be identified within the adhesive layer (asterisk).

Figure 9E:
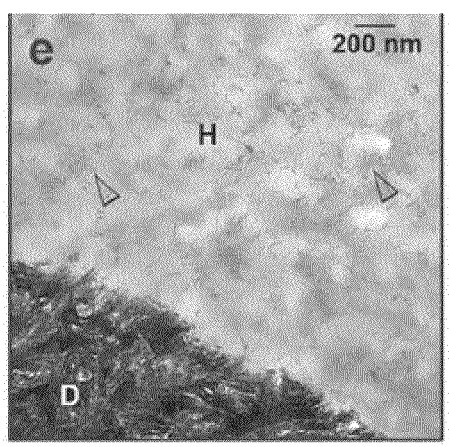
Figure 9F:
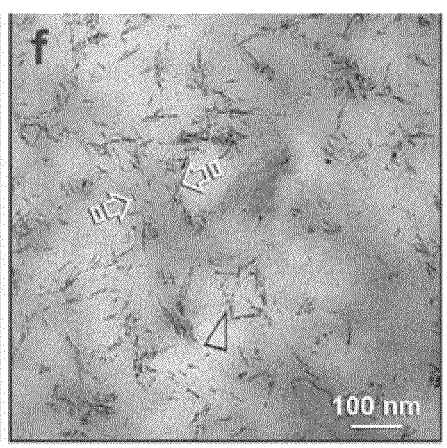

Analysis of a Single Bond Plus specimen, taken 2 mos after remineralization, also showed evidence of initial interfibrillar remineralization (open arrowheads) at the base of the hybrid layer (FIG. 9E). Higher magnification view of this specimen showed crystallites with the interfibrillar spaces of a collagen fibril (between open arrows). Needle-shaped crystallites (ca. 20 nm long) appeared to have been produced by the fusion of nanocrystals (open arrowhead). Thus, though initially these nanocrystals were much finer than the apatite platelets from the underlying mineralized dentin base (FIG. 9E), they appeared to have undergone mesoscopic assembly (Niederberger, M. et al., *Phys. Chem. Chem. Phys.*, 2006, 8:3271-3287; Xu, A-W. et al., *J. Mater. Chem.*, 2007, 17:415-449) and transformation into larger needle-shaped crystallites within the interfibrillar spaces (FIG. 9F).

Figure 10A:
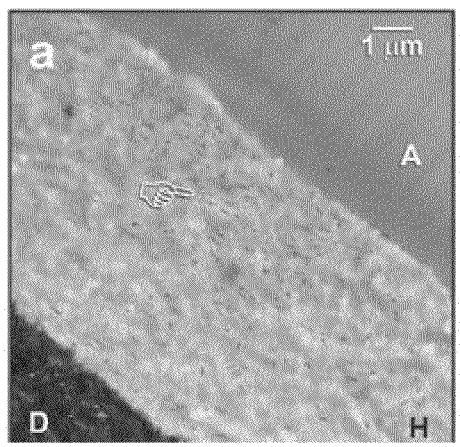
FIG. 10 shows in accordance with alternate embodiments of the present invention, transmission electron micrograph examples of intrafibrillar remineralization in resin-dentin interfaces after 2-3 mos of biomimetic remineralization in accordance with one embodiment of the present invention; Abbreviations: C, composite; A, unfilled adhesive; FA, filled adhesive; H, hybrid layer; D, mineralized dentin.
Figure 10B:
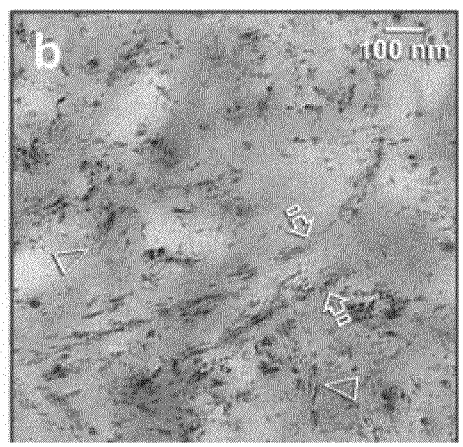
Figure 10C:
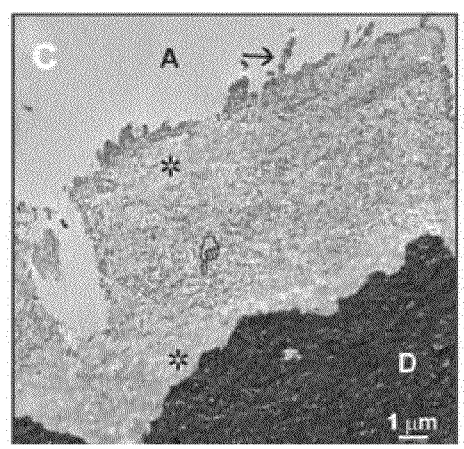
Figure 10D:
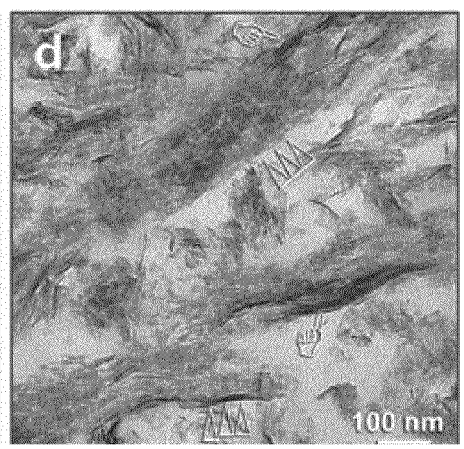
Figure 10E:
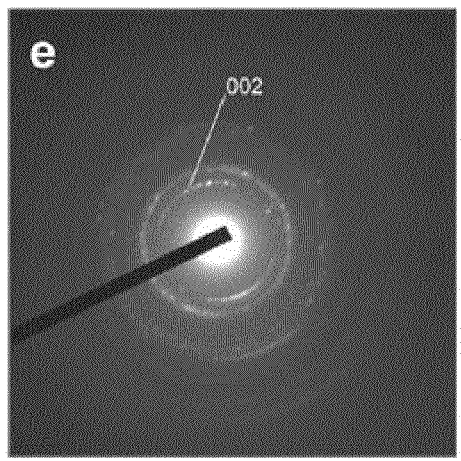
Figure 10F:
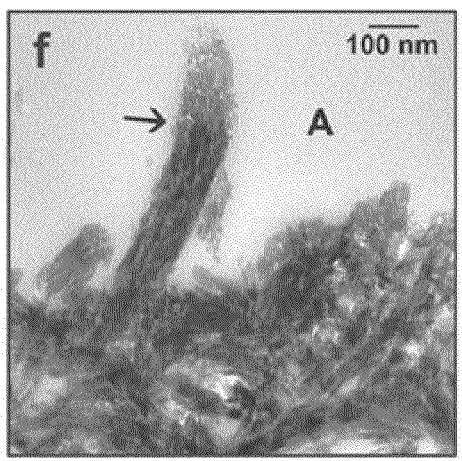

Intrafibrillar remineralization could be identified at lower magnifications after 2-3 mos of remineralization. FIG. 10A depicts a One-Step specimen taken after 2 mos, with remineralization (pointer) observable at low magnification. The earliest evidence of intrafibrillar remineralization could be seen at higher magnification, depicted as an ordered alignment of nanocrystals (open arrowheads) within the collagen fibril (FIG. 10B). These intrafibrillar nanocrystals co-exist with adjacent interfibrillar nanocrystals (FIG. 10B), both of which appeared to be much smaller than the intrafibrillar and interfibrillar apatite platelets seen in mineralized intertubular dentin. A more advanced stage of intrafibrillar remineralization (after 3 mos) in a One-Step specimen is depicted in FIG. 10C. Remineralized regions within the hybrid layers could be readily discerned from those non-remineralized, better-resin-infiltrated regions, with remineralization occurring in the middle of the hybrid layer and along the surface collagen fibrils (arrow). Regions that were not remineralized (asterisks) were probably better infiltrated with adhesive resin. FIG. 10D depicts a high-magnification view of the region depicted by the "pointer" in FIG. 10C, illustrating a more advanced stage of intrafibrillar remineralization. Likely as a result of mesoscopic transformation of the original nanocrystals, crystallite platelets (ca. 20 nm long) were observed stacked in a repeating and orderly sequence (triple open arrowheads) within the collagen fibrils (ca. 100 nm in diameter). The crystallographic c-axes of these electron-dense platelets were well aligned with the longitudinal axis of the collagen fibrils. Larger needle-shaped crystallites (ca. 50 nm) could be seen (pointers) along the periphery of the fibrils (i.e., interfibrillar remineralization). FIG. 10E depicts the arc-shaped diffraction patterns ascribed to the [002] plane of apatite suggest that the c-axes of the platelets have a preferential orientation (i.e., because the crystallographic c-axes of these electron-dense platelets were well aligned with the longitudinal axis of the collagen fibrils, they produced arc-shaped SAED patterns (see Mishima, H. et al., *J. Dent. Res.*, 1986, 65:932-934; Müller, F. A. et al., *J. Crystal Growth*, 2007, 304:464-471) along the [002] plane of apatite). A high magnification view of FIG. 10C shows that, along the surface of the hybrid layer, heavily remineralized, shag-carpet-appearing collagen fibrils extend into the adhesive layer (FIG. 10F).

Figure 11A:
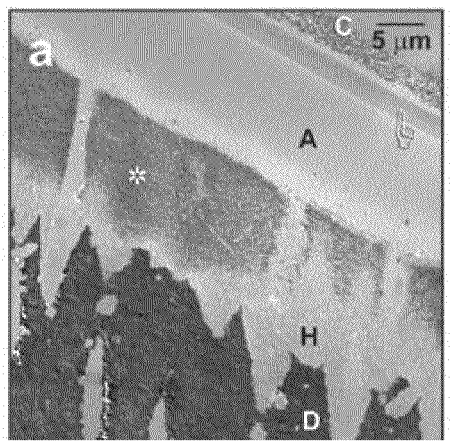
FIG. 11 shows in accordance with alternate embodiments of the present invention, transmission electron micrographs depicting the extent of remineralization in resin-dentin interfaces after 3-4 mos of biomimetic remineralization in accordance with one embodiment of the present invention; Abbreviations: C, composite; A, unfilled adhesive; FA, filled adhesive; H, hybrid layer; D, mineralized dentin.
Figure 11B:
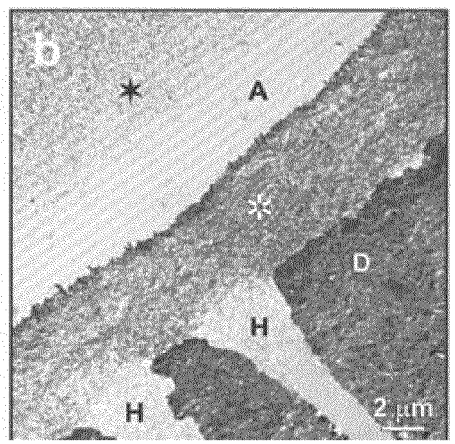
Figure 11C:
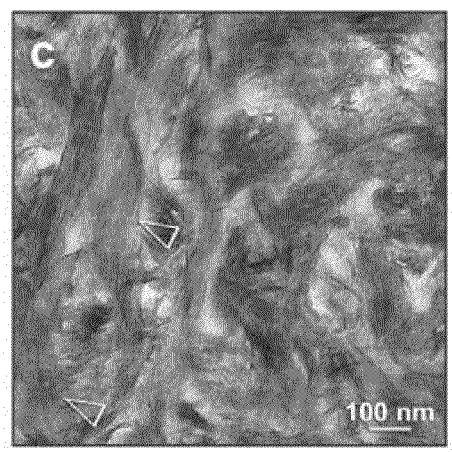
Figure 11D:
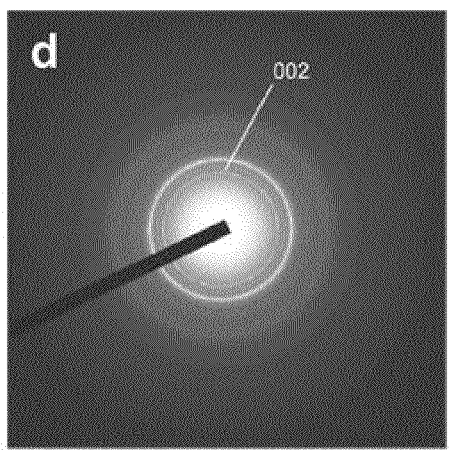
Figure 11E:
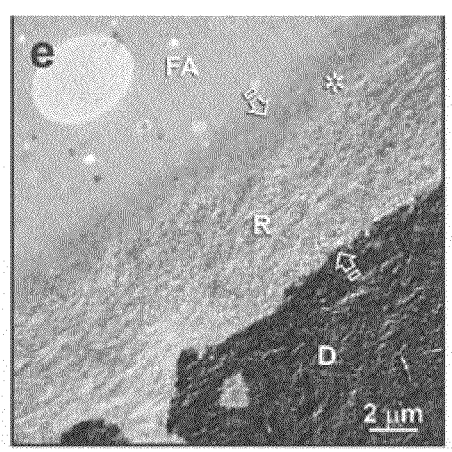
Figure 11F:
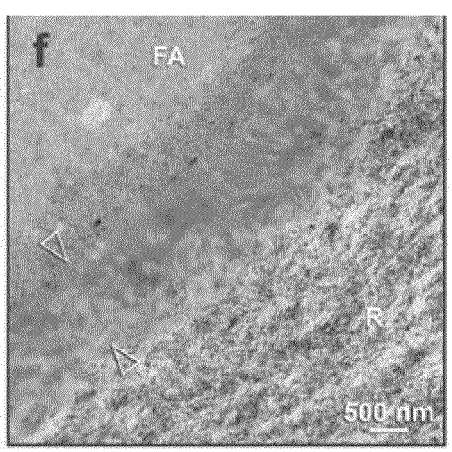

The extent of remineralization within the hybrid layers appeared to be complete after 4 mos. Resin-dentin interfaces created with One-Step adhesive were retrieved after 3 and 4 mos of remineralization, respectively (FIG. 11A and FIG. 11B). Extensive remineralization had occurred in the top and middle parts of the hybrid layers (FIG. 11A: electron-dense band (pointer) beneath the composite; FIG. 11B: adhesive layer (star)). The bases of the hybrid layers did not remineralize, suggesting that these regions are better resin-infiltrated. Although intrafibrillar remineralization could still be recognized by the banded appearance in some collagen fibrils (open arrowheads), it was largely masked by more extensive interfibrillar mineral deposits (FIG. 11C). These heavily remineralized regions revealed SAED ring patterns that were devoid of arc-shaped patterns in the [002] plane (FIG. 11D), suggesting a more random crystallite arrangement contributed by the more extensive interfibrillar remineralization (diffraction rings were present that are ascribed to the major [002] and [211] planes of apatites). For Single Bond Plus, remineralization occurred within the middle and base of the hybrid layer (R) (FIG. 11E). The surface 1-2 μm of the hybrid layer appeared to be better infiltrated by the filled adhesive and was not remineralized (FIG. 11F). At high magnification, the absence of remineralization (between open arrowheads) from the surface of the hybrid layer was clear.

Figure 12A:
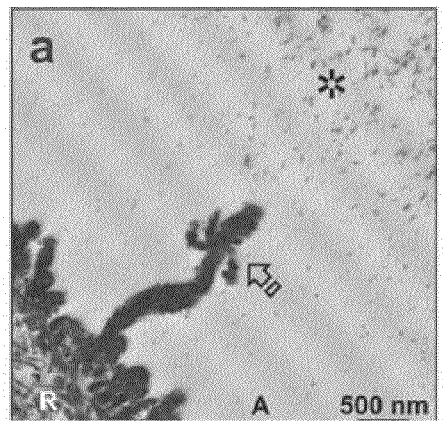
FIG. 12 shows in accordance with alternate embodiments of the present invention, that during the process of biomimetic remineralization, intra-resin apatite depositions are created within the porous adhesive resin layers; Abbreviations: C, composite; A, unfilled adhesive; FA, filled adhesive; H, hybrid layer; D, mineralized dentin; P, polyalkenoic acid copolymer; R, remineralized hybrid layer.
Figure 12B:
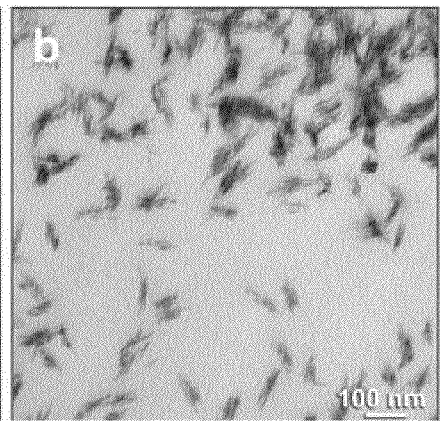
Figure 12C:
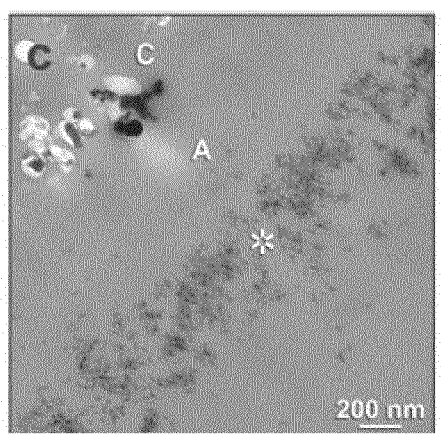
Figure 12D:
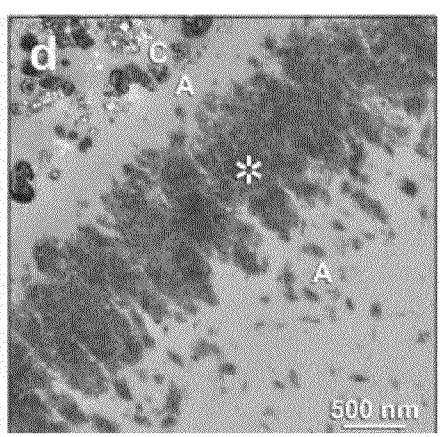
Figure 12E:
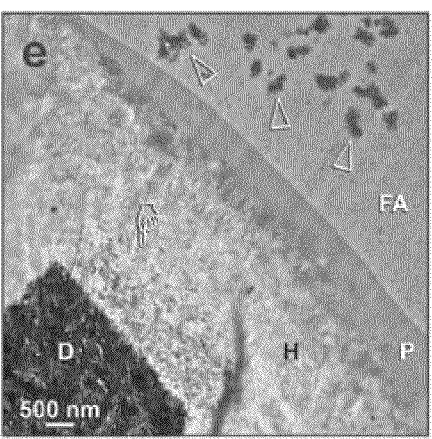
Figure 12F:
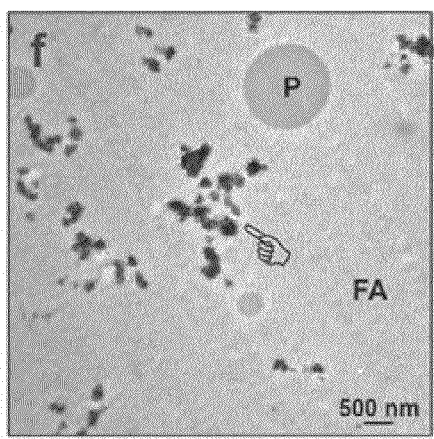

During the process of remineralization, apatite crystallites were deposited within the porous adhesive layers (i.e., intra-resin apatite depositions). For One-Step, the two predominant sites of deposition were the water-rich channels (water trees) close to the dentin surface (FIG. 12A and FIG. 12B) and the water-rich zone directly beneath the resin composite (FIG. 12C and FIG. 12D). FIG. 12A depicts a One-Step specimen after 3 mos of remineralization, showing a highly remineralized hybrid layer surface (R), a large remineralized water tree (arrow) that was filled with apatite platelets, and a region farther away that contained innumerable apatite clusters (asterisk). At a high magnification, each of the apatite clusters depicted in FIG. 12A consisted of apatite platelets that were arranged into bundles (FIG. 12B). FIG. 12C shows a One-Step specimen after 2 mos of remineralization, wherein a zone of crystallites (asterisk) could be seen in the adhesive layer beneath the resin composite. Another One-Step specimen after 4 mos of remineralization is shown in FIG. 12D, with a denser layer of crystallite deposits (asterisk) at almost the same site as the specimen in the previous FIG. 11F. Intra-resin apatite deposition in Single-Bond Plus was difficult to discern, since nanofillers were present in this filled adhesive. Nevertheless, water trees that originated from the surface of the hybrid layer were filled with minerals after remineralization (FIG. 12E and FIG. 12F). FIG. 12E shows a Single-Bond Plus specimen retrieved after 2 mos, with partial remineralization along the base of the hybrid layer (pointer). Water trees on top of the hybrid layer were filled with electron-dense minerals (open arrowheads). FIG. 12F shows that these mineral-containing water trees (pointer) extended through the entire adhesive layer.

Example 3

The effect on calcium hydroxide production, and thus pH, of different amounts of calcium hydroxide source in remineralizing restorative material was assayed. The calcium hydroxide source assayed was set Portland cement. The Portland cement was included as an inorganic filler in the form of Portland cement powder in the remineralization restorative material as indicated below. The Portland cement powder was made from Portland cement that had set for one week in 100% relative humidity at 37° C. The Portland cement powder was prepared by freezing blocks of set Portland cement in liquid nitrogen and reducing it to powder in a mixer mill (Model MM301, Retsch, Newtown, Pa., USA) for 10 min at 30 Hz. The fractured frozen Portland cement powder is then sieved from multiple screens to obtain powder between 10-20 tm. This fine powder is kept dry and frozen until use.

Demineralized dentin samples were prepared by etching flat coronal dentin surfaces with 37% phosphoric acid for 60 sec.

In this embodiment, a therapeutic primer containing 500 μg/mL polyacrylic acid (PAA), 200 μg/mL of polyvinylphosphonic acid (PVPA) and 750 μg/mL of glycine or 1610 μg/mL of glutamic acid was applied topically to demineralized dentin. The therapeutic primer was applied with a microbrush for 3 min to allow time for inward diffusion of its reagents. The therapeutic primer was in the form of a water-soluble gel (e.g., hydroxypropyl methylcellulose, polyvinyl alcohol). The viscosity of the primer prevents the subsequently applied "remineralizing restorative material" from actually entering the dentin.

After topical application of the therapeutic primer to the demineralized dentin, the therapeutic primer was overlaid with a 1 mm thick layer of remineralizing resin and light-cured for 40 sec. The remineralizing restorative material is a composite containing a resin matrix formulation comprising TEGDMA 48.5%, HEMA 50%, camphorquionone (CQ) 0.5 wt %, 1% ethyl-N,N-dimethyl-4-aminobenzoate (EDAMB) and 10-50 wt % set Portland cement (PC) as inorganic filler (e.g., 0.1 g PC/1 mL resin to 0.5 g PC/1 mL resin). Just prior to application to the demineralized dentin, the remineralizing restorative material is agitated to insure a uniform suspension of the Portland cement powder in the resin composite. The camphorquinone is a commonly used photoinitiator in dental resins that absorbs blue light and decomposes to free radicals thereby initiating the polymerization of resin monomers containing double bonds and convert these monomers into polymers After applying and curing the remineralizing resin, it was overlaid with a hybrid resin composite that protects the remineralizing restorative material and provides esthetic appeal and wear resistance.

Slabs of 1 mm thick slices of restorative material-bonded dentin (12×3×1 mm; 36 mm$^3$) were individually placed in 2 mL of distilled water in sealed glass vials at 37'C. The calcium and hydroxyl ion concentrations produced by different concentrations of Portland cement in the remineralizing restorative material, as reflected by pH of the distilled water in the glass vials, were measured over time using ion-specific electrodes. The results are shown in FIGS. 13A-C.

FIG. 13A shows the mean pH of 1 mL of distilled water containing one beam of remineralizing restorative material wherein the remineralizing restorative material contained 0, 0.1, 0.2, 0.3, 0.4, 0.5 or 1.0 gram of set Portland cement powder/mL of resin. In the absence of Portland cement powder, the pH of the water was about 6.0 after 24 hrs of incubation. In remineralizing restorative material containing 0.1 g/ml of Portland cement powder as filler, the pH rose to about 10. The pH of the sample water increased to above 11 as the amount of Portland cement powder in the remineralizing restorative material increased. FIG. 13B shows that calcium ions were released from the remineralizing restorative material as well. The calcium concentration present in the deionized water in which the dentin-bonded restorative material was immersed was measured using a calcium ion-specific electrode connected to a millivolt recorder. Note that more calcium ions were released when the remineralizing restorative material contained more Portland cement as filler.

FIG. 13C shows the initial modulus of elasticity of the remineralizing restorative materials as a function of the percent added Portland cement powder as filler. Adding Portland cement powder filler did not decrease the stiffness of the resin. There were no significant differences in the initial stiffness of the remineralizing restorative materials as a function of filler content. After 10 days in water, the modulus of elasticity of the remineralizing restorative material-filled beams fell to values less than 1 GPa. This drop of modulus of elasticity is universal to polymerized hydrophilic resin blends employed for dental use after water sorption (Ito et al., *Biomaterials*, 2005, 26:6449-6459).

Example 4

Demineralized dentin disks were prepared and topically treated with the therapeutic primer as described in Example 3. The demineralized dentin disks were then treated with remineralizing restorative materials comprising a light-curable resin and an inorganic phase. The resin was a liquid comprising 70% BisGMA, 28.5% HEMA, containing 1% EDBA and 0.5 wt % amphorquinone (CQ). The liquid resin was mixed at a 50-60 wt % with the inorganic phase comprising 5-10 wt % of silanized nanosilica (OX-50, Bisco Inc., Schaumberg, Ill., USA) and 30-45 wt % set Portland cement powder (Table I). The remineralizing restorative material (resin comonomers and set Portland cement powder) was placed within a circular Teflon mold to create a circular disk of the restorative material. After light polymerization, the hardened material was removed from the Teflon mold, resulting in a circular disk. FIG. 14A shows the rate of release of hydroxyl$^-$ ions from polymerized disks of this material, as reflected by the pH, over a 30 day period. FIG. 14B shows the rate of release of calcium from the same dentin disk samples over 32 days.

FIG. 14A shows the rate of release of hydroxyl ions (OH$^-$) from four different formulations remineralizing restorative material (Table 1) containing 35-45% Portland cement powder filler. Demineralized dentin disks to which these remineralization restorative materials were applied were placed in individual bottles containing 15 ml of distilled water. The pH of the solution was measured from 0-720 hrs (i.e., 30 days). Note that within 1 hr all four specimen groups reflected an increase in pH from 6.5 to 10, which further increased to 11.5 by 144 hrs.

TABLE I

Composition of remineralizing restorative materials.

| Group | PC (wt %) | OX-50 (wt %) | Resin comonomer (wt %) |
|---|---|---|---|
| I | 35 | 5 | 60 |
| II | 30 | 10 | 60 |
| III | 45 | 5 | 50 |
| IV | 40 | 10 | 50 |

PC: set Portland cement power (over 1 week aged)
OX-50: silanized nanosilica fillers (Bisco, Inc., Schaumberg, IL) (OX50 is a non-calcium releasing silica siller that is used as a rhelogy modifier.)
Resin comonomer: 70% BisGMA, 28.75% HEMA, 1% EDMAB, 0.25% CQ (Resin comonomer mixture is a resin blend that lacks fillers.)

FIG. 14B shows the cumulative release of calcium ions from these same disks. There was a 12 hour delay in the release of calcium compared to OH⁻ (see FIG. 14A). After 12 hrs, the calcium ion release increased over time for more than 30 days with no evidence of reaching a plateau. Release of calcium ions over a long period of time is a desirable characteristic of the present invention because remineralization of dentin requires many months.

When slabs of the resin composite were subjected to 3-point flexure assays to measure their modulus of elasticity, they gave a Young's modulus of 3.30±0.25 GPa dry and 1.76±0.25 GPa after immersion in water for 3 days (not shown).

Example 5

According to the National Institute of Dental and Craniofacial Research Strategic Plan (2001), dental caries begins early in life: 18% of preschoolers in the U.S. have already experienced tooth decay and by age 6-8, more than half have experienced this disease—making it 5-8 times more common than asthma. Failure of dental restorations is thus a major concern in pediatric dental practices (Soncini, J. A., et al., *J. Am. Dent. Assoc.*, 2007, 138:763-772). As such, it is appropriate to show that imperfect hybrid layers created in primary teeth can be remineralized as well as permanent teeth.

Example 5 illustrates remineralization of dentin from primary teeth that had been bonded with Adper Prompt (3M ESPE, St. Paul, Minn., USA), a self-etching adhesive. A dentin adhesive is a blend of hydrophilic resin monomers and catalyst dissolved in a solvent, usually ethanol or acetone to produce a low viscosity solution for coupling restorative materials to enamel and/or dentin. Similar to Example 2, 1 mm thick slices of Adper Prompt-bonded dentin were laid on top of a Portland cement-based remineralizing restorative material, which was immersed in the biomimetic remineralization medium described in Example 2, comprising 500 µg/ml of polyacrylic acid and 200 µg/ml of polyvinylphosphonic acid. The resin-bonded assembly was left in place for up to 6 months. Some of the retrieved specimens were soaked in a 0.1% Rhodamine B fluorescent dye and examined using confocal laser scanning microscopy (CLSM). Other specimens were prepared for TEM examination.

FIG. 15A and FIG. 15B show complementary CLSM and TEM images, respectively, of a control specimen that had not been subjected to biomimetic remineralization. In these images, "A" represents the adhesive layer, "D" represents the mineralized dentin base and the region demarcated by the opposing white open arrows represents the completely demineralized hybrid layer. In FIG. 15A, the fully mineralized dentin base took up minimal fluorescent dye, indicating that there were minimal water-filled voids within the mineralized intertubular dentin. The adhesive layer took up a variable extent of fluorescent dye, indicating that water is present within the polymerized adhesive resin matrix. However, the entire hybrid layer was heavily filled with the fluorescent dye, indicating that the interior of the demineralized collagen fibrils within the hybrid layer was filled with water that was not replaced by the adhesive resin. The complementary TEM image in FIG. 15B revealed a 6-7 µm thick hybrid layer that was completely demineralized. A dentinal tubule (T) could also be identified. As FIG. 15 illustrates a control specimen, there was no remineralization of the hybrid layer. The hybrid layer appears gray as it allows the passage of electrons through the section. Conversely, the underlying heavily mineralized dentin base appeared dark as the heavily mineralized collagen matrix blocked the passage of electrons through those regions of the TEM section.

FIG. 15C represents the CLSM image of a fluorescent dye-impregnated specimen that had undergone biomimetic remineralization for 6 months. In this specimen, there was quenching of the fluorescence along the surface of the hybrid layer (white pointer), indicating that the water within the collagen fibrils were replaced deposition of apatite crystals (i.e., remineralization of the dentin collagen matrix). Fluorescence was still evident in most of the base of the hybrid layer. The adhesive layer and the resin tags within the dentinal tubules also became highly fluorescent due to uptake of water by the very hydrophilic resin polymer matrix. The complementary TEM image in FIG. 11C shows that the top part of the hybrid layer was remineralized (asterisk) and became almost as dark as the underlying mineralized dentin base "D".

Figure 15E:
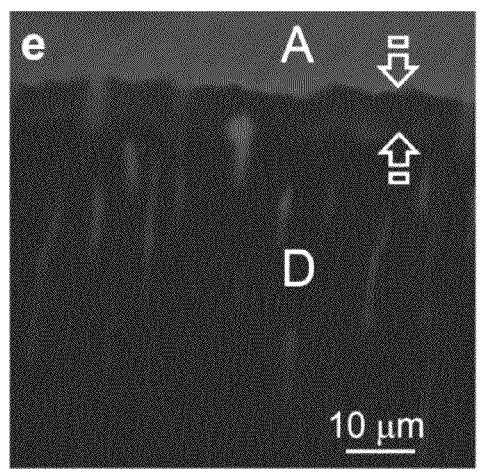
FIG. 15 shows in accordance with alternate embodiments of the present invention, remineralization of resin-bonded primary tooth dentin by the deposition of apatite crystals within hybrid layer water-filled voids between the remineralizing restorative material and the dentin tissue.
Figure 15F:
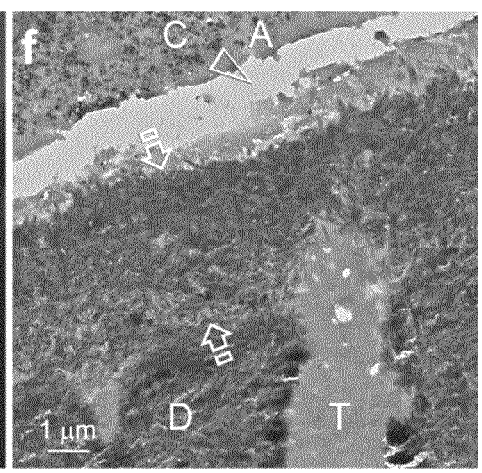

FIG. 15E shows the CLSM image of another hybrid layer after 6 months of biomimetic remineralization. In this specimen, fluorescence in the hybrid layer was markedly quenched, where as the adhesive layer and resin tags remained highly fluorescent. The complementary TEM image in FIG. 15F shows that the entire hybrid layer was remineralized, although there were still electron-lucent (gray) spaces at the base of the hybrid layer that still permitted the passage of electrons. These spaces were probably better infiltrated by the adhesive resin. These gray-appearing spaces account for the very pale fluorescence observed along the base of the hybrid layer in FIG. 15E.

Example 6

Example 6 illustrates the effect of remineralization according to the present invention on the stiffness of the hybrid layer of resin-bonded dentin. As the depth of the remineralizing matrix is often only 4-6 µm deep and appears random in the hybrid layer depending on the initial quality of resin infiltration, the use of nanoindentation techniques to follow the increase in matrix stiffness is not practical. This is illustrated in the TEM image in FIG. 16A. The specimen in this image was bonded with One-Step and had been subjected to remineralization using the biomimetic analog-containing medium described in the previous examples. One can see that remineralization was non-uniform within the hybrid layer (between white open arrows). There are regions that are heavily remineralized (white pointer), regions that are less heavily remineralized (white arrow) and regions that are not mineralized (asterisk). In addition, the base of the hybrid layer, which was usually better resin-infiltrated, was also not remineralized (white open arrowhead). The labels "A" represents the adhesive, "ID" represents the intertubular dentin and "T"s represent dentinal tubules.

It can be anticipated that making a vertical line of nanoindentations across the hybrid layer every 1 µm can only result in the generation of a few stiffness values, which does not reflect the regional stiffness variation within the hybrid layer. Also, standard analysis methods of quasi-static nanoindentation load/displacement data assume purely elastic/plastic material behavior, particularly during the loading and unloading portions of the test. This assumption ignores viscoelastic effects that exist throughout the entirety of the indentation test. The most commonly accepted quasi-static analysis measures stiffness by calculating the slope of the initial portion of the unloading curve. This analysis assumes that all recovery observed during the unloading is elastic recovery, which is true for most ceramics and metals. However, most polymers show strongly viscoelastic behavior, which implies a time-dependant recovery. Therefore the unloading portion of the load/displacement data is a convolution of elastic and viscoelastic recovery, rendering it nearly impossible to calculate a true modulus.

Dynamic mechanical testing (DMA) techniques were developed primarily in response to the insufficiencies in the legitimacy of quasi-static testing for materials that display significant time-dependant deformation and recovery. For viscoelastic materials, it is very difficult to obtain meaningful and accurate data using quasi-static testing due to the large effect that the choice of the loading function and the type of tip utilized will have on the measured properties due to creep and strain rate effects. Additionally, in the case of viscoelastic materials, it is desirable to have the capability of characterizing both components of the complex modulus, the storage and the loss modulus. Characterization of the viscoelastic properties of polymers requires quantifying a complex modulus, which is ignored by quasi-static testing, as discussed previously. The complex modulus is comprised of two moduli, a storage modulus and a loss modulus, which are each representative of two different components of the materials behavior. The storage modulus relates to the stiffness of the material, or the in phase response of the material to the applied force. This modulus relates the elastic recovery of the sample, which is the amount of energy recovered from the sample subsequent to a loading cycle. The storage modulus is proportional to the ratio of the applied force amplitude to the displacement amplitude that is in phase with the applied force. The loss modulus relates to the damping behavior of the material and is observed by the time lag between the maximum force and the maximum displacement. This damping is the amount of energy put into the sample during the indentation that is dissipated by various processes that facilitate energetic losses, primarily heat generation.

Thus, FIG. 16B, FIG. 16C and FIG. 16D represent two-dimensional mapping data of the complex modulus, storage modulus and loss modulus of a biomimetically remineralized specimen, respectively, that is similar to that depicted in FIG. 16A. The DMA testing was performed using a scanning nanoindentor (TriboIndenter, Hysitron, Inc., Minneapolis, Minn., USA) equipped with a dynamic testing module to superimpose a small sinusoidal load on the quasi static load during nanoindentation testing. The nanoindentation transducer is connected to a Berkovich (three-sided pyramid) diamond indentation tip and a scanning probe microscope, enabling mapping of the surface features of the specimen during testing. FIG. 16B and FIG. 16C show that, similar to the TEM image in FIG. 16A, the stiffness within the remineralized hybrid layer was non-uniform. In some parts of the remineralized hybrid layer, the complex and the storage moduli of the hybrid layer approximated that of the underlying mineralized dentin base. In other non-remineralized regions of the hybrid layer, both the complex and loss moduli in those regions were considerably lower, approximating those values derived from the dentin adhesive. Also, FIG. 16D shows that, because the hybrid layer contains resin materials which are viscoelastic in nature, the loss modulus of the hybrid layer was considerably higher than that of the underlying mineralized dentin.

FIG. 17A shows the variation in complex modulus of the above specimen from one representative vertical line through the resin composite, adhesive, hybrid layer and mineralized intertubular dentin, spanning a length of 25 microns. The "a" label represents a sparsely remineralized region within the hybrid layer. The "b" labels represent regions within the hybrid layer that are not remineralized, including the base of the hybrid layer. The "c" label represents variation in the complex modulus of a heavily remineralized region of the hybrid layer. One can see that the complex modulus of the remineralized hybrid layer approximates those values obtained from the intertubular dentin. Statistical analysis of 500 data points derived from 5 similar remineralized specimens showed that the complex modulus in the more heavily remineralized "c" region of the hybrid layers (15,022±6,503 MPa) were significantly less than but close to the complex modulus of the intertubular dentin (17,768±8,084 MPa) ($p<0.05$). The diminished complex modulus is due to the presence of resins from the dentin adhesive within the hybrid layer. The complex modulus of the non-remineralized "b" regions of the hybrid layer (5,286±727 MPa) was significantly less than the more heavily remineralized "c" regions, which was not significantly different from that exhibited by the slightly dehydrated adhesive (5,069±833 MPa). The slight dehydration also accounts for the increase in stiffness of the adhesive.

Thus, the incompletely resin-infiltrated parts of the hybrid layer of resin-bonded dentin exhibits a higher degree of stiffness as a result of remineralization as compared to demineralized dentin. However, the hybrid layer displays non-homogenous areas of stiffness. The underlying mineralized dentin base exhibits the highest degree of stiffness but this stiffness is also not uniform.

Example 7

Example 7 illustrates an embodiment of the present invention wherein the collagen-binding nucleation factor is a chemical phosphorylating agent. The chemical phosphorylating agent in this example comprises sodium trimetaphosphate. Further, in this embodiment, the sodium trimetaphosphate is applied to demineralized dentin in the form of a therapeutic primer. Human dentin was sectioned with a water-cooled diamond cutting machine to create a flat bonding surface that was devoid of enamel.

In this embodiment, a therapeutic primer comprising 2.5% sodium trimetaphosphate in deionized was applied directly to acid-etched dentin for 5 min as a therapeutic primer. After treating the dentin tissue sample with the therapeutic primer, the dentin tissue sample was overlaid and bonded with One-Step adhesive (Bisco Inc.). The resin-bonded dentin tissue samples were then placed on top of a Portland cement-containing remineralizing restorative material containing Portland cement powder as a filler (as described in Example 4) to simulate the application of the remineralizing restorative material to the demineralized dentin. The assembly was then immersed in the remineralizing medium described in Example 2 which comprises 500 µg/mL polyacrylic acid (MW=1800 Da) as the calcium phosphate-binding apatite stabilizer Sodium trimetaphosphate functions as a chemical phosphorylating agent at pH>9.0. In this example, the therapeutic primer was not adjusted to pH>9.0. Rather, the diffusion of hydroxyl ions from the Portland cement-containing remineralizing restorative material into the One-Step resin-bonded dentin was relied upon to raise the pH.

FIG. 18 illustrates the extent of remineralization of resin-bonded dentin resulting from the above described experiments. Abbreviations include: T: dentinal tubule; D: mineralized dentin.

Figure 18A:
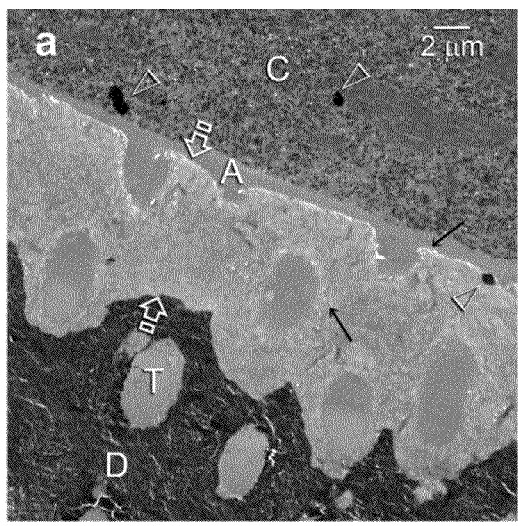
FIG. 18 shows in accordance with one embodiment of the present invention, remineralization of demineralized dentin using a therapeutic primer comprising 2.5% sodium trimetaphosphate as a collagen-binding nucleation factor in conjunction with a remineralizing restorative material. Abbreviations: A, adhesive; T, dentinal tubule; D, mineralized dentin.

FIG. 18A represents the TEM image of a representative sodium trimetaphosphate pre-treated control specimen (i.e., no additional biomimetic analog supplement in the remineralization medium) that was retrieved after the 2 months. No remineralization could be identified within the 5 µm thick hybrid layer (between white open arrows). Only 0.3-0.5 µm diameter electron-dense clusters (white open arrowheads) were seen within the resin composite layer (C) adjacent to the unfilled dentin adhesive (A), and along the dentin surface.

Figure 18B:
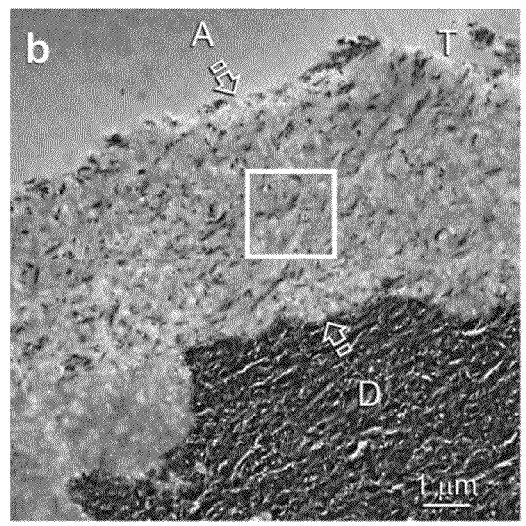

FIG. 18B illustrates the bottom-up remineralization process in a sodium trimetaphosphate-treated specimen that had been remineralized for 2 months using a biomimetic remineralization medium containing 500 µg/ml polyacrylic acid. Electron-dense collagen fibrils (i.e., representative of intrafibrillar remineralization) could be observed within the hybrid layer (between open white arrows). Only partial remineralization could be seen within this zone, probably in spaces that were not completely filled with the dentin adhesive resin.

Figure 18C:
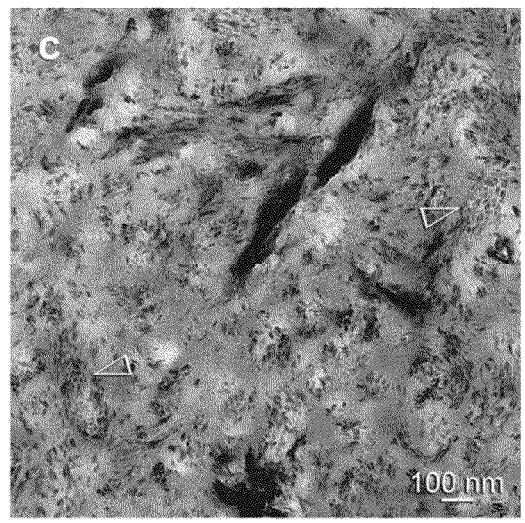
Figure 18D:
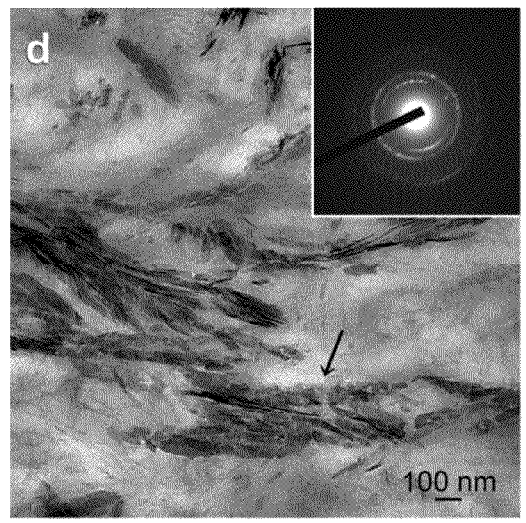

FIG. 18C represents a higher magnification of the square area shown in FIG. 18B. Non-overlapping intrafibrillar platelets could be identified within the collagen fibrils (between white open arrowheads). FIG. 18D shows in detail some of the more heavily remineralized collagen fibrils shown in FIG. 18C. Overlapping crystallite platelets could be seen within the collagen fibrils (arrow). Selected area electron diffraction (SAED; inset) of those crystallites revealed lattice spacings that were characteristic of apatite.

The examples of the present invention thus demonstrate that mineralized dentin collagen within teeth may be prepared under conditions where the biological activity of odontoblasts or other pulpal cells cannot exert mineralizing activity. For example, in some embodiments, in caries-affected dentin where the dentinal tubules have been occluded by mineral crystals, the overlying partially to fully demineralized dentin may be mineralized if the dentin is treated with a calcium phosphate-binding apatite stabilizer and a collagen-binding nucleation factor and a remineralizing restorative material that seals the dentin surface away from the contaminating action of septic whole saliva in the oral environment and slowly releases calcium ions and hydroxyl ions that cause remineralization of the dentin matrix collagen in situ.

The present invention has been described generally and with an emphasis on particular embodiments. It should be apparent to those of ordinary skill in the art that modifications can be made to the above disclosure and still fit within the scope and spirit of the invention. It is intended, contemplated, and therefore within the scope of the invention to combine any of the plurality of different elements in each of the embodiments in the above disclosure with any other embodiment. Moreover, when a range is disclosed, any number that falls within the range is a contemplated endpoint, even if that number is not explicitly disclosed. Also, although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Where methods and steps described above indicate certain events occurring in certain order, those of ordinary skill in the art will recognize that the ordering of certain steps may be modified and that such modification are in accordance with the variations of the invention. Furthermore, certain steps may be performed concurrently in a parallel process when possible, as well as performed sequentially as described above. Therefore, the above description should not be taken as limiting the scope of the invention but rather the invention should be defined by the below claims. Moreover, the list of any references mentioned in the disclosure are herein incorporated by reference in their entirety.

That which is claimed is:

1. A remineralizing restorative composition for producing a mineralized dental tissue, the remineralizing restorative composition comprising:
   a calcium ion source and a hydroxide ion source, wherein the calcium ion source and the hydroxide ion source is a cement;
   a calcium phosphate-binding apatite stabilizer and a collagen-binding nucleation factor as a single biomimetic entity wherein the single biomimetic entity comprises poly(acrylic acid-co-vinyl phosphonic acid), poly(aspartic acid-co-vinyl phosphonic acid), poly(methacrylic acid-co-vinyl phosphonic acid), poly(acrylic acid-co-vinyl aminomethylene phosphonic acid), poly[acrylic acid-co-bis(2-chloroethyl)vinylphosphonate], poly[acrylic acid-co-1-hydroxyethylidene-1,1-diphosphonic acid] or poly[aspartic acid-co-bis(2-chloroethyl) vinylphosphonate;
   a phosphate ion source; and
   wherein the calcium ions are released over time for at least 30 days.

2. The composition of claim 1, wherein the remineralizing restorative material comprises a resin.

3. The composition of claim 1, formulated as a gel or paste.

4. A kit comprising:
   a remineralizing restorative composition for producing a mineralized dental tissue comprising: (a) a calcium ion source and a hydroxide ion source, wherein the calcium ion source and the hydroxide ion source is a cement; (b) a phosphate ion source; and (c) a calcium phosphate-binding apatite stabilizer and a collagen-binding nucleation factor as a single biomimetic entity wherein the single biomimetic entity comprises poly(acrylic acid-co-vinyl phosphonic acid), poly(aspartic acid-co-vinyl phosphonic acid), poly(methacrylic acid-co-vinyl phosphonic acid), poly(acrylic acid-co-vinyl aminomethylene phosphonic acid), poly[acrylic acid-co-bis(2-chloroethyl)vinylphosphonate], poly[acrylic acid-co-1-hydroxyethylidene-1,1-diphosphonic acid] or poly[aspartic acid-co-bis(2-chloroethyl) vinylphosphonate; wherein the remineralizing restorative composition is provided in a sealed container with an opening suitable for delivery of the remineralizing restorative composition to the site of mineralization, wherein the calcium ions are released over time for at least 30 days; and
   instructions for use.

5. The kit of claim 4, wherein the remineralizing restorative material comprises a resin.

* * * * *